US009375703B2

(12) United States Patent
Harlin et al.

(10) Patent No.: US 9,375,703 B2
(45) Date of Patent: Jun. 28, 2016

(54) ALGAL THERMOPLASTICS, THERMOSETS, PAPER, ADSORBANTS AND ABSORBANTS

(71) Applicant: Solazyme, Inc., South San Francisco, CA (US)

(72) Inventors: Ali Harlin, Espoo (FI); Anna-stiina Jääskeläinen, Espoo (FI); Jani Kiuru, Espoo (FI); Christiane Laine, Espoo (FI); Tiina Liitiä, Espoo (FI); Kalle Nättinen, Espoo (FI); Jaakko Pere, Espoo (FI); Sonia Sousa, South San Francisco, CA (US); John Piechocki, South San Francisco, CA (US); Adrienne McKee, South San Francisco, CA (US); Jeffrey J. Cernohous, Hudson, WI (US); Adam R. Pawloski, Lake Elmo, MN (US)

(73) Assignee: Solazyme, Inc., South San Francisco, CA (US)

( * ) Notice: Subject to any disclaimer, the term of this patent is extended or adjusted under 35 U.S.C. 154(b) by 333 days.

(21) Appl. No.: 13/725,518

(22) Filed: Dec. 21, 2012

(65) Prior Publication Data

US 2013/0236937 A1    Sep. 12, 2013

Related U.S. Application Data

(60) Provisional application No. 61/579,961, filed on Dec. 23, 2011, provisional application No. 61/615,832, filed on Mar. 26, 2012, provisional application No. 61/636,356, filed on Mar. 27, 2012, provisional application No. 61/671,066, filed on Jul. 12, 2012, provisional application No. 61/691,210, filed on Aug. 20, 2012, provisional application No. 61/701,530, filed on Sep. 14, 2012, provisional application No. 61/728,807, filed on Nov. 21, 2012.

(51) Int. Cl.

| C08K 11/00 | (2006.01) |
|---|---|
| B01J 20/26 | (2006.01) |
| B01J 20/30 | (2006.01) |
| C12N 1/12 | (2006.01) |
| C08L 101/16 | (2006.01) |
| C12P 7/64 | (2006.01) |
| D21H 13/10 | (2006.01) |
| D21H 11/12 | (2006.01) |
| D21H 17/02 | (2006.01) |
| D21H 17/21 | (2006.01) |
| B01J 20/24 | (2006.01) |
| B01J 20/28 | (2006.01) |

(52) U.S. Cl.
CPC ............ *B01J 20/3078* (2013.01); *B01J 20/24* (2013.01); *B01J 20/26* (2013.01); *B01J 20/265* (2013.01); *B01J 20/28033* (2013.01); *C08K 11/00* (2013.01); *C08L 101/16* (2013.01); *C12N 1/12* (2013.01); *C12P 7/6445* (2013.01); *C12P 7/6463* (2013.01); *D21H 11/12* (2013.01); *D21H 13/10* (2013.01); *D21H 17/02* (2013.01); *D21H 17/21* (2013.01); *B01J 2220/4843* (2013.01)

(58) Field of Classification Search
CPC ........ B01J 20/3078; B01J 20/26; C08K 11/00
USPC .......................... 435/134; 524/310, 313, 599
See application file for complete search history.

(56) References Cited

U.S. PATENT DOCUMENTS

| 2,639,239 A | 5/1953 | Elliott |
|---|---|---|
| 3,345,358 A | 10/1967 | Adam |
| 3,723,413 A | 3/1973 | Chatterjee et al. |
| 3,795,670 A | 3/1974 | Mark et al. |
| 4,000,127 A | 12/1976 | Cornelissens et al. |
| 4,689,408 A | 8/1987 | Gelman et al. |
| 5,288,318 A | 2/1994 | Mayer et al. |
| 5,352,709 A | 10/1994 | Tarrant et al. |
| 5,367,003 A | 11/1994 | Petcavich |
| 5,607,551 A | 3/1997 | Farrington, Jr. et al. |
| 5,654,103 A | 8/1997 | Troadec |

(Continued)

FOREIGN PATENT DOCUMENTS

| WO | WO2008/151149 | 12/2008 |
|---|---|---|
| WO | WO2009/126843 | 10/2009 |

(Continued)

OTHER PUBLICATIONS

PCT International Search Report and Written Opinion dated Mar. 20, 2013 issued in PCT/US2012/071462.
PCT International Preliminary Report on Patentability dated Jun. 24, 2014 issued in PCT/US2012/071462.

(Continued)

*Primary Examiner* — Robert Harlan
(74) *Attorney, Agent, or Firm* — Weaver Austin Villeneuve & Sampson LLP

(57) ABSTRACT

Provided are biomass-based materials and valuable uses of microalgal biomass including: (i) acetylation of microalgal biomass to produce a material useful in the production of thermoplastics; (ii) use of triglyceride containing microalgal biomass for production of thermoplastics; (iii) combination of microalgal biomass and at least one type of plant polymer to produce a material useful in the production of thermoplastics; (iv) anionization of microalgal biomass to form a water absorbant material; (v) cationization of microalgal biomass, and optional flocculation, to form a water absorbant material; (vi) crosslinking of anionized microalgal biomass; (vii) carbonization of microalgal biomass; and (viii) use of microalgal biomass in the making of paper.

17 Claims, 6 Drawing Sheets

(56) References Cited

U.S. PATENT DOCUMENTS

| | | | |
|---|---|---|---|
| 5,779,960 | A | 7/1998 | Berlowitz-Tarrant et al. |
| 5,910,545 | A | 6/1999 | Tsai et al. |
| 5,939,467 | A | 8/1999 | Wnuk et al. |
| 6,027,611 | A | 2/2000 | McFarland et al. |
| 6,177,193 | B1 | 1/2001 | Tsai et al. |
| 6,323,307 | B1 | 11/2001 | Bigg et al. |
| 6,765,042 | B1 | 7/2004 | Thornton et al. |
| 7,393,590 | B2 | 7/2008 | Scheer et al. |
| 7,485,719 | B2 | 2/2009 | Abe et al. |
| 7,608,649 | B2 | 10/2009 | Sun et al. |
| 7,662,953 | B2 | 2/2010 | Valta et al. |
| 7,682,821 | B2 | 3/2010 | Woods et al. |
| 7,927,532 | B2 | 4/2011 | Scheer et al. |
| 7,932,378 | B2 | 4/2011 | Mikkonen et al. |
| 8,119,583 | B2 | 2/2012 | Day et al. |
| 8,222,232 | B2 * | 7/2012 | Anderson et al. ............... 514/62 |
| 8,278,261 | B2 | 10/2012 | Day et al. |
| 8,450,083 | B2 | 5/2013 | Day et al. |
| 8,524,811 | B2 | 9/2013 | Shi et al. |
| 2010/0272940 | A1 | 10/2010 | Shi et al. |
| 2011/0303375 | A1 | 12/2011 | Shannon et al. |
| 2012/0130099 | A1 | 5/2012 | Wittenberg et al. |
| 2013/0153828 | A1 * | 6/2013 | Kaneiwa ............... D21H 17/02 252/478 |
| 2013/0295268 | A1 | 11/2013 | Day et al. |
| 2013/0296591 | A1 | 11/2013 | Day et al. |
| 2014/0275355 | A1 | 9/2014 | Cernohous et al. |

FOREIGN PATENT DOCUMENTS

| | | | |
|---|---|---|---|
| WO | WO2010/063032 | 6/2010 | |
| WO | WO2010/120939 | 10/2010 | |
| WO | WO2010/125490 | 11/2010 | |
| WO | WO 2010/125490 A2 * | 11/2010 | ............ C08K 11/00 |
| WO | WO2010/138620 | 12/2010 | |
| WO | WO2011/150411 | 12/2011 | |
| WO | WO2013/096891 | 6/2013 | |

OTHER PUBLICATIONS

Chiellini, et al. (2008) "Biodegradable Thermoplastic Composites Based on Polyvinyl Alcohol and Algae," *Biomacromolecules* 9:1007-1013.

Fowler, et al. (2006) "Biocomposites: technology, environmental credentials and market forces," *Journal of the Science of Food and Agriculture* 86(12):1781-1789.

Lee, et al. (2008) "Red algae fibre/poly(butylene succinate) biocomposites: The effect of fibre content on their mechanical and thermal properties," *Composites Science and Technology* 68:1266-1272.

Libra, et al. (2011) "Hydrothermal carbonization of biomass residuals: a comparative review of the chemistry, processes and applications of wet and dry pyrolysis," *Biofuels* 2(1): 89-124.

Otsuki, et al. (2004) "Synthesis and Tensile Properties of a Novel Composite of *Chlorella* and Polyethylene," *Journal of Applied Polymer Science* 92:812-816.

Plastic News (Aug. 9, 2012) "Georgia company commercializing algae-based 'green' plastics" 5 Pages; Retrieved from the Internet: URL: http://www.plasticsnews.com/article/20120809/NEWS/308099983.

Zhang, et al. (2000) "An exploratory research of PVC-Chlorella composite material (PCCM) as effective utilization of Chlorella biologically fixing $CO_2$," *Journal of Materials Science* 35:2603-2609.

Zhang, et al. (2000) "Synthesis and characterization of a novel blend of polypropylene with *Chlorella*," *Journal of Material Chemistry* 10:2666-2672.

US Office Action, dated Apr. 1, 2015, issued in U.S. Appl. No. 14/213,950.

Chinese First Office Action dated Jul. 28, 2015 issued in CN 201280069855.9.

Caliendo, Heather (Aug. 27, 2013) "Is algae plastic the next big thing in packaging?" *Plastics Today.com*, [retrieved from the Internet at http://www.plasticstoday.com/article/Is-algae-plastic-the-next-big-thing-in-packaging0827. . . On Dec. 1, 2015], 2pp.

* cited by examiner

ALGAL THERMOPLASTICS, THERMOSETS, PAPER, ADSORBANTS AND ABSORBANTS

CROSS-REFERENCE TO RELATED APPLICATIONS

This application claims the benefit under 35 U.S.C. 119(e) of U.S. Provisional Patent Application No. 61/579,961, filed Dec. 23, 2011, U.S. Provisional Patent Application No. 61/615,832, filed Mar. 26, 2012, U.S. Provisional Patent Application No. 61/616,356, filed Mar. 27, 2012, U.S. Provisional Patent Application No. 61/671,066, filed Jul. 12, 2012, U.S. Provisional Patent Application No. 61/691,210, filed Aug. 20, 2012, U.S. Provisional Patent Application No. 61/701,530, filed Sep. 14, 2012, and U.S. Provisional Patent Application No. 61/728,807, filed Nov. 21, 2012. Each of these applications is incorporated herein by reference in its entirety for all purposes.

TECHNICAL FIELD

The present invention relates to materials produced using biomass that include cell wall remains of heterotrophically cultivated single cells. In particular, the biomass can be used to produce products including plastic, paper, adsorbent, or absorbant materials.

BACKGROUND

Algae, and especially microalgae (single celled algae) have been the subject of recent interest in terms of the production of lipids and fatty acids for use in fuels, chemicals, soaps, and foods. As disclosed in WO2008/151149 and WO2010/063032, certain species of microalgae can be cultured on a fixed carbon source (e.g., glucose, sucrose, glycerol or hydrolyzed cellulosic material) without the use of sunlight to produce high yields of lipid as measured as a percentage of dry cell weight. Some species of miroalgae are obligate heterotrophs; they lack the ability to use sunlight and so must grow on a fixed carbon source (i.e., not carbon dioxide). The aforementioned patent applications also teach that microalgae can be genetically engineered to allow growth on sucrose and to alter the chain length and saturation profiles of the fatty acids produced by the microalgae. Thus, the microalgae can be used as a biocatalyst to upconvert sugar into more valuable products. Other technologies use autotrophic algae, bacteria, yeast or cyanobacteria to produce oil from sugar.

SUMMARY

In one aspect, the invention provides thermoplastic compositions or thermoset compositions. In some embodiments, the thermoplastic compositions or thermoset compositions comprise one or more of a covalently modified microbial biomass from an oleaginous microbe and a non-covalently modified biomass from a heterotrophically cultivated microbe, wherein the microbial biomass optionally comprises from 0.25% to 90% triglyceride by dry cell weight. In some embodiments, the microalgal biomass comprises from 0.25% to 20% triglyceride by dry cell weight. In some embodiments, the fatty acid profile of the triglyceride comprises at least 60% C18:1; at least 50% combined total amount of C10, C12, and C14; or at least 70% combined total amount of C16:0 and C18:1. The thermoplastic composition may optionally further comprise one or more plant polymers. Suitable plant polymers include, e.g., switchgrass, rice straw, sugar beet pulp, corn starch, potato starch, cassava starch, sugar cane bagasse, soybean hulls, dry rosemary, cellulose, corn stover, dilapidated cake from soybean, canola, cottonseed, sunflower, jatropha seeds, paper pulp, and waste paper. In various embodiments, the microbe is an oleaginous microbe. In some embodiments, the microbe has been lysed. In some embodiments, the biomass is microalgal biomass. In some embodiments, the microalgal biomass is derived from cells having a mean diameter of between 1 micron and 50 microns. In various embodiments, the microalgal biomass comprises one or more plant polymers. In some embodiments, the covalently modified microalgal biomass has been covalently modified with a hydrophobic group, a hydrophilic group, an anionic group or a cationic group. In some embodiments, the covalently modified microalgal biomass is microalgal biomass that has been modified by one or more reactions selected from the group consisting of acylation, hydroxylation, epoxidation, isocyanization, and silylation. In a particular embodiment, the acylation reaction is acetylation. In some embodiments, polysaccharide of the microalgal biomass is covalently modified. In some embodiment, the covalently modified algal biomass is characterized by a degree of substitution ("DS") value in the range of 0.25 to 3. In some embodiments, the microalgal biomass is unbleached. In various embodiments, the microalgal biomass comprises less than 5000 ppm color generating compounds (e.g., chlorophyll). In various embodiments, the microalgal biomass comprises less than 3000 ppm chlorophyll. In some embodiments, the biomass is of microalgae that are heterotrophs, and optionally obligate heterotrophs. In some embodiments, the microalgae are of the class Trebouxiophyceae. In some embodiments, the microalgae are of the genus *Chlorella* or the genus *Prototheca*. In a particular embodiment, the microalgae are *Prototheca moriformis*. In some embodiments, the thermoplastic composition further comprises a plasticizer. Suitable plasticizers include, e.g., glycerol, sorbitol, triacetin, triethyl citrate, acetyl triethyl citrate, tributyl cirtate, acetyl tributyl citrate, trioctyl citrate, acetyl trioctyl citrate, trihexyl citrate, butyryl trihexyl citrate, trimethyl citrate, alkyl sulphonic acid phenyl ester, and 1,2-cyclohexane dicarboxylic acid diisononyl ester. In some embodiments, the composition further comprises a surfactant. Suitable surfactants include, e.g., glyceryl monostearate, ethoxylated dimethylsiloxane, polyoxyethylene, propylene oxide, an organic sulfate, an organic sulfonate, an alkyl polyglycoside, and a polyolefin glycol. In various embodiments, the microbial biomass is a fraction that is insoluble in an aqueous solvent, said insoluble fraction produced by removing components soluble in an aqueous solvent from microbial biomass. In various embodiments, the microbial biomass is insoluble in an aqueous solvent. In various embodiments, the composition has been formed through extruding, molding, blowing, coating, or calendering. In various embodiments, the composition is a film.

In a further aspect, the invention provides blended compositions. In various embodiments, the blended compositions comprise a thermoplastic composition as described above and herein, and a second thermoplastic composition. In some embodiments, the second thermoplastic composition is present in the range of 5 to 95% by mass. Suitable second thermoplastic compositions include, e.g., polylactic acid, polycaprolactone, polyesteramide, polyhydroxybutyrate, polyhydroxybutyrate-co-valerate, polyhydroxyalkanoate, polyethylene, polypropylene, polyethylene terephthalate, and polycarbonate. In some embodiments, the second thermoplastic composition is a derivative of polyethylene. In some embodiments, the second thermoplastic composition is a derivative of polypropylene. In some embodiments, the second thermoplastic composition is of biological origin. In some embodiments, the thermoplastic composition has one or more of the following characteristics:
 (a) a Young's modulus of 300-3000 MPa;
 (b) a tensile strength of 5-70 MPa;
 (c) a tensile strength at maximum load of 5-50 MPa; and/or
 (d) an ultimate elongation of 1-400%.

In a related aspect, the invention provides absorbent compositions. In various embodiments, the absorbent compositions comprise thermoplastic compositions or thermoset compositions as described above and herein. In various embodiments, the absorbent compositions comprise microbial biomass from a microbe covalently modified with a hydrophilic moiety. In some embodiments, the absorbent composition is cross-linked. In various embodiments, the microbe is an oleaginous microbe. In some embodiments, the microbe has been lysed. In some embodiments, the microbe is a microalga. In some embodiments, the microalga cell has a mean diameter of between approximately 1 micron and approximately 50 microns. In various embodiments, the hydrophilic moiety is anionic, cationic, zwitterionic, or neutral. In some embodiments, the anionic moiety is a carboxylate, a sulfate, a sulfonate, or a phosphate. In some embodiments, the cationic moiety is an amine or a substituted amine. In some embodiments, the neutral moiety is an hydroxyl or acyl. In a particular embodiment, the anionic group is a carboxylate group, and the covalently modified biomass is formed by modifying the biomass with a carboxymethyl group. In some embodiments, the modified biomass is characterized by a degree of substitution ("DS") value of 0.25 to 3. In some embodiments, the covalently modified biomass comprises polysaccharide. In some embodiments, the absorbent compositions further comprise a cross-linking agent. Suitable cross-linking agents include, e.g., aldehydes, C2-C8 dialdehydes, C2-C9 polycarboxylic acids, epichlorhydrin, divinyl sulphone, ethylenediamine, cystamine dihydrochloride, acrylic acid, sorbitan monolaurate, polyethylene glycol, sodium zirconium lactate, sodium borate, genipin, and sodium stearate. In a particular embodiment, the dialdehyde is glyoxal. In various embodiments, the absorbent composition is included in a structural material. In some embodiments, the fatty acid composition of the microbial biomass comprises at least 60% C18:1; at least 50% combined total amount of C10, C12, and C14; or at least 70% combined total amount of C16:0 and C18:1. In some embodiments, the microbial biomass is a biomass fraction that is insoluble in an aqueous solvent, said insoluble fraction produced by removing components soluble in an aqueous solvent from microbial biomass. In some embodiments, the microbial biomass is insoluble in an aqueous solvent. In various embodiments, the composition absorbs at least 5 times its weight in liquid. In some embodiments, the composition absorbs at least 5 times its weight in liquid after immersion in liquid for 4 hrs. In various embodiments, the composition absorbs at least 10 times its weight in liquid. In some embodiments, the composition absorbs at least 10 times its weight in liquid after immersion in liquid for 4 hrs. In various embodiments, the composition absorbs at least 20 times its weight in liquid. In some embodiments, the composition absorbs at least 20 times its weight in liquid after immersion in liquid for 4 hrs. In various embodiments, the composition absorbs at least 50 times its weight in liquid. In some embodiments, the composition absorbs at least 50 times its weight in liquid after immersion in liquid for 4 hrs. In various embodiments, the composition absorbs at least 100 times its weight in liquid. In some embodiments, the composition absorbs at least 100 times its weight in liquid after immersion in liquid for 4 hrs.

In various embodiments, the liquid is water, saline, oil, urine, or blood. In some embodiments, the biomass is of microalgae that are heterotrophs, and optionally obligate heterotrophs. In some embodiments, the microalgae are of the class Trebouxiophyceae. In some embodiments, the microalgae are of the genus *Chlorella* or the genus *Prototheca*. In a particular embodiment, the microalgae are *Prototheca moriformis*. In various embodiments, the absorbent composition further comprises a plant polymer. Suitable plant polymers include, e.g., switchgrass, rice straw, sugar beet pulp, sugar cane bagasse, soybean hulls, corn starch, potato starch, cassava starch, dry rosemary, cellulose, corn stover, dilapidated cake from soybean, canola, cottonseed, sunflower, jatropha seeds, paper pulp, and waste paper. In some embodiments, the composition further comprises a second absorbent composition. Suitable second absorbent compositions include, e.g., polyacrylate, polyacrylamide, polyvinyl alcohol, starch, starch-g-polyacrylonitrile, cellulose, carboxymethyl cellulose, and hydroxyethyl cellulose.

In another aspect, the invention provides methods of making an adsorbent material, wherein the method comprises the steps of: a) preparing biomass from a microbe; and b) hydrothermally carbonizing the biomass, thereby making the adsorbent material. In various embodiments, the microbe is an oleaginous microbe. In some embodiments, the microbe has been lysed. In some embodiments, the microbe is microalga. In some embodiments, the microalgal biomass is prepared from microalgal cells having a mean diameter between approximately 1 micron and approximately 50 microns. In some embodiments, the biomass is of microalgae that are heterotrophs, and optionally obligate heterotrophs. In some embodiments, the microalgae are of the class Trebouxiophyceae. In some embodiments, the microalgae are of the genus *Chlorella* or the genus *Prototheca*. In some embodiments, the microalgae are *Prototheca moriformis*. In some embodiments, microalgal biomass is carbonized in the presence of an acidic catalyst. In various embodiments, the amount of acidic catalyst is in the range of 0.01 grams to 0.6 grams per gram of microalgal biomass. In various embodiments, the microalgal biomass is hydrothermally carbonized by heating to between about 180° C. to 350° C. in the presence of water from 60 minutes to 180 minutes. In some embodiments, the fatty acid composition of the biomass comprises at least 60% C18:1; at least 50% combined total amount of C10, C12, and C14; or at least 70% combined total amount of C16:0 and C18:1. In some embodiments, the biomass is a biomass fraction that is insoluble in an aqueous solvent, said insoluble fraction produced by removing components soluble in an aqueous solvent from oleaginous microbial biomass. In some embodiments, the adsorbent material further comprises a plant polymer. Suitable plant polymers include, e.g., switchgrass, rice straw, sugar beet pulp, sugar cane bagasse, soybean hulls, dry rosemary, corn starch, potato starch, cassava starch, cellulose, corn stover, dilapidated cake from soybean, canola, cottonseed, sunflower, jatropha seeds, paper pulp, and waste paper. In some embodiments, the methods further comprise the step of recovering and optionally using one or more nutrient from the biomass. Suitable nutrients include, e.g., phosphorus, nitrogen, and potassium. In various embodiments using is recycling the one or more nutrient to support the cultivation of additional microbial cells or using the one or more nutrient as a fertilizer to support plant growth.

In a related aspect, the invention provides paper products. In various embodiments, the paper products comprise thermoplastic compositions or thermoset compositions as described above and herein. In various embodiments, the paper products comprise 0.1% to 50% biomass from heterotrophically cultivated microbes. In some embodiments, the microbe is an oleaginous microbe. In some embodiments, the microbe has been lysed. In some embodiments, the microbe is a microalga. In some embodiments, the microalgal biomass is derived from microalgal cells having a mean diameter between approximately 1 micron and approximately 50 microns. In some embodiments, the biomass is of microalgae that are obligate heterotrophs. In some embodiments, the microalgae are of the class Trebouxiophyceae. In some embodiments, the microalgae are of the genus *Chlorella* or the genus *Prototheca*. In a particular embodiment, the microalgae are *Prototheca moriformis*. In some embodiments, the biomass is a biomass fraction that is insoluble in an aqueous solvent, said insoluble fraction produced by removing components soluble in an aqueous solvent from microalgal biomass. In some embodiments, the biomass is insoluble in an aqueous solvent. In various embodiments, the biomass is a biomass fraction that is insoluble in an aqueous solvent, said insoluble fraction produced by removing components soluble in an aqueous solvent from oleaginous microbial biomass. In some embodiments, triglyceride has been removed from the microalgal cells. For example, in various embodiments, the amount of triglyceride removed from the cells is more than 10% of the dry weight of the microalgal cells. In some embodiments, one or more cationic retention aids have been added to the biomass. Suitable cationic retention aids include, e.g., polydiallyldimethylammonium chlorides, branched polyacrylamides, polyamines having a molar mass of more than 50,000, modified polyamines grafted with ethylenimine, crosslinked polyetheramides, polyvinylimidazoles, polyvinylpyrrolidines, polyvinylimidazolines, polyvinyltetrahydropyrines, poly(dialkylaminoalkylvinylethers), poly(diakylaminoalkyl(meth)acrylates) in protonated or quaternized form, polyamidoamines obtained from a dicarboxylic acid, polyalkylenepolymines grafted with ethylenimine and crosslinked with polyethylene glycol dichlorohydrin ether, polyamidoamines reacted with epichlorohydrin to give water-soluble condensates, cationic starches, alum, polyaluminum chloride, and combinations thereof. In various embodiments, the paper products further comprise a flocculating agent. In various embodiments, the fatty acid composition of biomass comprises at least 60% C18:1; at least 50% combined total amount of C10, C12, and C14; or at least 70% combined total amount of C16:0 and C18:1. In various embodiments, one or more additional papermaking fiber has been added to the biomass. Suitable papermaking fibers include, e.g., cotton, straw, flax, jute hemp, bagasse, eucalyptus, maple, birch, aspen, pine, bamboo, rayon, polyester, fibers from recycled paper products and mixtures thereof. In some embodiments, the paper product further comprises a plant polymer. Suitable plant polymers include, e.g., switchgrass, rice straw, sugar beet pulp, sugar cane bagasse, soybean hulls, dry rosemary, corn starch, potato starch, cassava starch, cellulose, corn stover, dilapidated cake from soybean, canola, cottonseed, sunflower, jatropha seeds, paper pulp, and waste paper.

In another aspect, the invention provides methods of making a thermoplastic composition or a thermoset composition. In some embodiments, methods comprise the steps of: a) providing biomass from heterotrophically cultivated microbes; b) acylating the polysaccharides within the biomass, wherein the acylating is optionally acetylating; c) adding one or more of a plasticizer, an additional polymer, a filler, or a cross-linking agent. In various embodiments, the methods further comprise the step d) adding one or more plant polymers. Suitable plant polymers include, e.g., switchgrass, rice straw, sugar beet pulp, sugar cane bagasse, soybean hulls, dry rosemary, corn starch, potato starch, cassava starch, cellulose, corn stover, dilapidated cake from soybean, canola, cottonseed, sunflower, jatropha seeds, paper pulp, and waste paper. In some embodiments, the microbe is an oleaginous microbe. In some embodiments, the microbe has been lysed. In some embodiments, the acylating comprises acetylating using acetic anhydride or acetyl chloride as an acetylating agent. In some embodiments, the additional polymer is biodegradable. In some embodiments, the microbe is a microalga. In some embodiments, microalgal biomass is derived from microalgal cells having a mean diameter between approximately 1 micron and approximately 50 microns. In some embodiments, the biomass is of microalgae that are heterotrophs, and optionally obligate heterotrophs. In some embodiments, the microalgae are of the class Trebouxiophyceae. In some embodiments, the microalgae are of the genus *Chlorella* or the genus *Prototheca*. In a particular embodiment, the microalgae are *Prototheca moriformis*. In some embodiment, triglyceride has been removed from the microalgal cells, and wherein the amount of triglyceride removed from the microalgal cells is more than 10% of the dry weight of the microalgal cells. In some embodiments, the fatty acid composition of the biomass comprises at least 60% C18:1; at least 50% combined total amount of C10, C12, and C14; or at least 70% combined total amount of C16:0 and C18:1. Suitable plasticizers include, e.g., one or more of: glycerol, sorbitol, triacetin, triethyl citrate, acetyl triethyl citrate, tributyl cirtate, acetyl tributyl citrate, trioctyl citrate, acetyl trioctyl citrate, trihexyl citrate, butyryl trihexyl citrate, trimethyl citrate, alkyl sulphonic acid phenyl ester, and 1,2-cyclohexane dicarboxylic acid diisononyl ester. Suitable additional polymers include, e.g., of one or more of: polylactic acid, polycaprolactone, polyesteramide, polyhydroxybutyrate, polyhydroxybutyrate-co-valerate, polyhydroxyalkanoate, polyethylene, polypropylene, polyethylene terephthalate, and polycarbonate. In some embodiments, the biomass is insoluble in an aqueous solvent, said insoluble fraction produced by removing components soluble in an aqueous solvent from oleaginous microbial biomass. In some embodiments, the biomass is a biomass fraction that is insoluble in an aqueous solvent. In some embodiments, the methods further comprise the step of forming the thermoplastic through one or more steps selected from extruding, molding, blowing, coating, and calendering.

In one embodiment, a thermoset composition of the invention is made by covalently modifying biomass with a phenolic moiety, an isocyanate moiety, an epoxide moiety, or an imide moiety. Phenolized biomass can be prepared by reacting the biomass with a phenol containing reactant in the presence an acidic catalyst, for example, sulfuric acid. The phenolization reaction is typically carried out at temperatures of 50° C. to 200° C. One exemplary phenol containing reactant is benzyl alcohol. Biomass can be covalently modified with isocyanate moieties by reacting the biomass with a compound that contains one or more isocyanate moieties. The reaction is typically carried out at temperatures of 50° C. to 200° C. Exemplary compounds that contain one or more isocyanate moieties include methylene diphenyl diisocyanate (MDI), toluene diisocyanate (TDI), (HDI), isophorone diisocyanate (IPDI), and methyl isocyanate (MIC). The covalently modified isocyanate biomass is then reacted with a polyol to form the thermoset composition. Biomass can be covalently modified to comprise epoxides by reacting the biomass with peroxide containing reactants. The peroxide containing biomass is then subsequently cured to form the thermoset composition. Covalently modified biomass that contains imides can be prepared by reacting the biomass with for example, N,N- dimethylacetamide (DMAc) or N-methylpyrrolidinone (NMP), pyromellitic dianhydride (PMDA), and/or 4-4'oxydianiline.

In certain embodiments, a further aspect of the invention includes a process for producing triglyceride that entails (a) heterotrophically cultivating microalgal cells in a culture medium including crop-derived sugar so as to produce triglyceride inside the cells; (b) removing the triglyceride from the cells to produce an oil and a residual biomass; (c) hydrothermally carbonizing a water soluble fraction and/or water insoluble fraction of the biomass to produce a carbonized product and a nutrient-rich aqueous solution; and (d) repeating the process with recycling of the nutrients of the nutrient-rich aqueous solution to step (a) to support the cultivation of additional microalgal cells or using the nutrients of the nutrient-rich aqueous solution in the growing of crops. In particular embodiments, the microalgal cells have a mean diameter between approximately 1 micron and approximately 50 microns. In some embodiments, the microalgal cells are obligate heterotrophs. In certain embodiments, removed triglyceride accounts for more than 10% of the dry weight of the microalgal cells. In certain embodiments, the biomass is carbonized in the presence of an acidic catalyst. For example, the biomass can be hydrothermally carbonized by heating it in the presence of water to between about 180-350° C. for between 60 to 180 minutes. In such embodiments, the amount of acidic catalyst can be in the range of 0.01 grams to 0.6 grams per gram of biomass. Suitable acidic catalysts include, e.g., citric acid and acrylic acid. In certain embodiments, the fatty acid composition of the biomass includes at least 60% C18:1; at least 50% combined total amount of C10, C12, and C14; or at least 70% combined total amount of C16:0 and C18:1.

In certain embodiments, provided is a composition comprising a blend of a moldable polymer, a microalgal biomass, and optionally a lipid selected from a triacylglyceride, a fatty acid, a fatty acid salt, a fatty acid ester, and one or more combinations thereof, wherein the microalgal biomass is optionally covalently modified and is obtained from a heterotrophic oleaginous microalgae. In certain embodiments, provided is a composition comprising a blend of a moldable polymer, a microalgal biomass, and optionally a lipid selected from a triacylglyceride, a fatty acid, a fatty acid salt, a fatty acid ester, and one or more combinations thereof, wherein the microalgal biomass is optionally covalently modified and is obtained from a heterotrophic oleaginous microalgae that is an obligate heterotroph.

In certain embodiments, provided is a film comprising a composition provided herein.

In certain embodiments, provided is an injection molded article comprising a composition provided herein.

In one embodiment, the compositions provided herein do not contain a plant polymer.

These and other aspects and embodiments are further described in the drawings and detailed descriptions below.

BRIEF DESCRIPTION OF THE DRAWINGS

The foregoing features of the invention will be more readily understood by reference to the following detailed description, taken with reference to the accompanying drawing, in which.

DETAILED DESCRIPTION

Definitions

Figure 1:
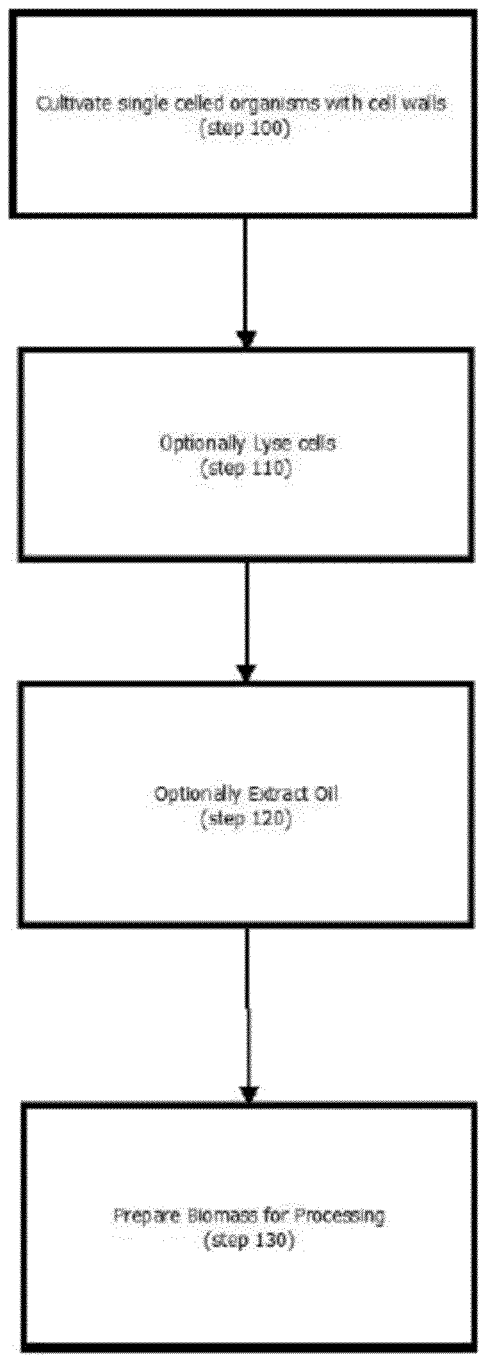
FIG. 1 shows a flow diagram depicting a method for preprocessing biomass in connection with some embodiments of the present invention.

"About" refers to the stated value ±10%.

"Acylation" refers to a reaction between a reactant having a hydroxy group and a reactant having activated carbonyl group to produce an ester linkage. Activated carbonyl groups include anhydrides, esters, acids, and acyl groups having a leaving group such as a halide attached to the carbonyl carbon. "Acetylation" refers to an ester producing reaction where one of the reactants has an acetyl ($CH_3C{=}O{-}$) group.

"Biomass" is material produced by growth and/or propagation of cells including whole cells, whole cell debris, cell wall material, polysaccharides, triglycerides, proteins, and other intracellular or extracellular components. "Residual biomass" refers to biomass that remains after cells are processed, such as when oil is extracted. In certain embodiments, the biomass comprises 65-50%, 50-30%, 40-20%, 30-10%, 20-10%, and 10-5% of the compositions provided herein.

"Oleaginous microbial biomass" shall mean biomass derived from oleaginous microbes.

An "oleaginous" cell is a cell capable of producing at least 20% lipid by dry cell weight, either in its wild-type form or upon recombinant or classical strain improvement. An "oleaginous microbe" or "oleaginous microorganism" is a microbe, including a microalga, that is oleaginous. In some embodiments, the cell produces at least 50%, at least 60%, at least 70%, at least 80%, or at least and 90% triglyceride by dry cell weight.

The term "bulk properties" in connection with the compositions provided herein refers to any measurable property of the composition, including those properties that are dependent on the size of the composition. Bulk properties include physical, mechanical, thermal, optical, barrier, and related performance properties of the composition. Specific properties include but are not limited to density, impact resistance, tensile strength, flexural strength, seal strength, glass transition temperature, melting point, melt flow index, porosity, thickness, color, brightness, opacity, light scattering, light absorption, roughness, water vapor transition rate, and water absorption. Bulk properties can be tested using conventional methods, such as those published by ASTM (American Society for Testing and Materials) International, TAPPI Standards, Scandinavian Pulp, Paper and Board Testing Committee (SCAN-C) and International Organization for Standardization (ISO). In some embodiments, the bulk properties of the composition differ in comparison to the bulk properties of the moldable polymer alone by 25% or less. In some embodiments, one of the bulk properties is increased by 10% or less. In other embodiments, one of the bulk properties is decreased by 10% or less.

The term "moldable polymer" refers to moldable synthetic or semi-synthetic polymers for use in plastics. The moldable polymers may be amorphous or semicrystalline, and include thermoplastic and thermosetting polymers. In some embodiments, the moldable polymer is also a biodegradable polymer.

In connection with a biomass derived material, "thermoplastic" shall mean a material or composition that is thermoplastic or is thermoplastic-like in that, in the presence of a plasticizer, elevated temperatures, and/or shearing, it melts and fluidizes, enabling its use in preparing articles traditionally made with thermoplastics. In one embodiment, microbial biomass is subjected to elevated temperatures and shearing in the presence of a plasticizer (e.g. a known thermoplastic) to form thermoplastics or blends thereof. In the softened state, the thermoplastic material can be formed into a finished product. Often, the thermoplastic material is first made into pellets, blocks or other convenient size; the pellets or blocks are re-softened, typically by heating, and shaped into a finished product.

"Thermoset" shall mean a material or composition that cures or hardens into a desired shape by the application of heat, radiation (e.g., ultraviolet light, laser radiation, etc.) or other energy sources to the material, or by a chemical reaction. Prior to curing, thermoset materials are malleable and can be molded into a desired form. Once cured, the thermoset material cannot be softened and remolded to a different form. The curing process transforms the material by a cross-linking process.

"Colored molecules" or "color generating impurities" as used herein refer to any compound that imparts a color to the extracted oil. "Colored molecules" or "color generating impurities" include for example, chlorophyll a, chlorophyll b, lycopenes, tocopherols, campesterols, tocotrienols, and carotenoids, such as beta carotene, luteins, zeaxanthin, astaxanthin. These molecules are preferably present in the microbial biomass or the extracted oil at a concentration of no more than 500 ppm, no more than 250 ppm, no more than 100 ppm, no more than 75 ppm, or no more than 25 ppm. In other embodiments, the amount of chlorophyll that is present in the microbial biomass or the extracted oil is less than 500 mg/kg, less than 100 mg/kg, less than 10 mg/kg, less than 1 mg·kg, less than 0.5 mg/kg, less than 0.1 mg/kg, less than 0.05 mg/kg, or less than 0.01 mg/kg.

"Cultivated", and variants thereof such as "cultured" and "fermented", refer to the intentional fostering of growth (increases in cell size, cellular contents, and/or cellular activity) and/or propagation (increases in cell numbers) of one or more cells by use of selected and/or controlled conditions. The combination of both growth and propagation is termed "proliferation." Examples of selected and/or controlled conditions include the use of a defined medium (with known characteristics such as pH, ionic strength, and carbon source), specified temperature, oxygen tension, carbon dioxide levels, and growth in a bioreactor. "Cultivated" does not refer to the growth or propagation of microorganisms in nature or otherwise without human intervention; for example, natural growth of an organism that ultimately becomes fossilized to produce geological crude oil is not cultivation. In some embodiments, microbes such as microalgae are cultivated on sugar from corn, sorghum, sugar cane, sugar beet, or molasses. In other embodiments the microbes are cultivated on sucrose.

"Covalently modified" shall mean microbial biomass wherein the polysaccharides, the proteins, or the triacylglycerols within the microbial biomass have been covalently modified with a hydrophobic group, a hydrophilic group, an anionic group or a cationic group prior to the formation of the thermoplastic material. During the thermoplastic forming process, components of the microbial biomass, for example, polysaccharides, proteins, and/or triacylglycerols, may be further covalently modified by exposure of the microbial biomass to heat, shearing and plasticizer.

"Lipid" refers to fatty acids and their derivatives, including free fatty acids and their salts, as well as fatty acid esters. Fatty acid esters include fatty acid alkyl esters and triacylglycerides. Fatty acid salts include sodium, potassium, magnesium, and calcium salts. Fatty acids can be referred to by shorthand notation "carbon number:number of double bonds". Thus C18:1 refers to an 18 carbon fatty acid chain having one double bond. In certain embodiments, the lipids provided herein comprise 15%, 10%, 5%, or 2% or less of the plastic and film compositions provided herein. In other embodiments the lipid is a calcium salt. In still other embodiments the lipid has at least 60% C18:1; or at least 50% combined total amount of C10, C12, and C14; or at least 70% combined total amount of C16:0 and C18:1.

"Fatty acid profile" refers to the distribution of fatty acids in a cell or oil derived from a cell in terms of chain length and/or saturation pattern. In this context the saturation pattern can comprise a measure of saturated versus unsaturated acid or a more detailed analysis of the distribution of the positions of double bonds in the various fatty acids of a cell. Unless specified otherwise, the fatty acid profile is expressed as a weight percent of the total fatty acid content.

"Lysis" is the breakage of the plasma membrane and optionally the cell wall of a biological organism sufficient to release at least some intracellular content, often by mechanical, chemical, viral or osmotic mechanisms that compromise its integrity. "Lysing" is the process of lysis.

"Microalgae" is a microbial organism that contains a chloroplast or plastid, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, *Volvox*, which is a simple multicellular photosynthetic microbe of two distinct cell types. Microalgae include cells such as *Chlorella, Dunaliella*, and *Prototheca*. Microalgae also include other microbial photosynthetic organisms that exhibit cell-cell adhesion, such as *Agmenellum, Anabaena*, and *Pyrobotrys*. Microalgae also include obligate heterotrophic microorganisms that have lost the ability to perform photosynthesis, such as certain dinoflagellate algae species and species of the genus *Prototheca*. In some embodiments the microalgae is a *Parachlorella, Prototheca, Chlorella* or strains having at least 85% nucleotide sequence identity in 23S rRNA sequences to a *Parachlorella, Prototheca*, or *Chlorella* strain. Certain nucleic acid sequences are disclosed in WO2009/126843 which is incorporated herein by reference in its entirety. Such sequences in WO2009/126843 include SEQ ID NOs:3-29.

The term "sugar" in connection with algal feedstock refers to carbohydrates that are derived from natural sources or that are synthetically or semi-synthetically prepared. Sugar can be derived from natural sources such as through extraction (e.g. sugarcane or sugar beet) or by further chemical, enzymatic processing (e.g. sugar from corn), and/or by depolymerization of cellulosic materials.

The present invention is based on the realization that biomass, particularly residual biomass that remains after cell lysis, especially of microalgae cultured heterotrophically, is a valuable product, the utilization of which confers substantial overall economic advantage to using the cells as production organisms for making fatty acids or other high value products. Indeed, the economic advantage gained may outweigh the expense associated with the lysis of the cell walls. Judicious use of the residual biomass may compensate for loss of efficiency in the process resulting from conversion of sugar and cell-energy to cell wall synthesis rather than toward production of the desired product. Embodiments of the invention also allow for recovery and potential recycling of valuable nutrients used in the culture of the microalgae, including phosphorous, potassium, and nitrogen. The materials so formed may have the added advantage of being biodegradable.

Furthermore, by using single-celled oleaginous microbial biomass, such as microalgal biomass, particles, comprising polysaccharides and/or proteins, having a size distribution that is believed to be unobtainable or difficult to obtain from multicellular sources of biomass (e.g., higher plants or multicellular algae) is obtained. For example, cells of oil-bearing Prototheca moriformis may have a tight size distribution around about 10 micron diameter. Cells of the microalgal biomass typically have a mean diameter between approximately 1 micron and approximately 50 microns. In certain cases the mean diameter ranges between approximately 2 microns and 40 microns, 3 microns and 30 microns, 4 microns and 20 microns or 5 microns and 15 microns.

After lysis and extraction of the oil, the residual biomass including the cell wall material may have a similarly tight size distribution. The size of the particles obtained, their distribution, the amount of residual oil remaining after oil extraction, and/or the protein or saccharide composition of biomass may confer previously unknown advantages to the products or process described herein. By contrast, the processing of fibers produced by higher plants may not afford the same particle size distribution. In one embodiment, the oleaginous microbial biomass, prior to lysis and extraction of the triacylglycerides, have a similar tight size distribution.

In one embodiment, the specific gravity of a thermoplastic or thermoset composition does not increase or does not significantly increase upon blending a polymer with single-celled oleaginous microbial biomass, such as microalgal biomass. Low or no increases in specific gravity is a desirable benefit when blending polymers with biomass for specific applications requiring light weight components. In some embodiments, the specific gravity of a thermoplastic or thermoset composition increases by less than 10%, less than 5%, less than 2%, or less than 1% when as much as 5%, 10%, 15%, 20%, 25%, 30%, 35%, or 40% by weight of a thermoplastic polymer is replaced with single-celled oleaginous microbial biomass, such as microalgal biomass, to form a thermoplastic or thermoset blend.

In particular, the following methods for treating biomass to increase its value are disclosed below: (i) acetylation of microalgal biomass to produce a material useful in the production of thermoplastics; (ii) use of triglyceride containing microalgal biomass for production of thermoplastics; (iii) combination of microalgal biomass and at least one type of plant polymer to produce a material useful in the production of thermoplastics; (iv) anionization of microalgal biomass to form a water absorbant material; (v) cationization of microalgal biomass, and optional flocculation, to form a water absorbant material; (vi) crosslinking of anionized microalgal biomass; (vii) carbonization of microalgal biomass; and (viii) use of microalgal biomass in the making of paper.

In addition, products produced by these processes and uses thereof are disclosed.

Production of Biomass.

For all of the embodiments presented herein, the cells may be grown heterotrophically as disclosed in (step 100). Although the cells may be individual plant cells (i.e., cells grown in culture), microbial cells are preferred. Microalgae may be grown heterotrophically as described in WO2008/151149 and WO2010/063032. The microalgae can also be an obligate heterotroph.

In various embodiments of the invention, the biomass is prepared by fermentation of a microbe selected from the group consisting of microalgae, oleaginous bacteria, oleaginous yeast, and fungi. In various embodiments, the microalgae is a species of a genus selected from Chlorella, Parachlorella, or Prototheca, or is one of the other species in Table 1. In various embodiments, the oleaginous bacteria is a species of the genus Rhodococcus. In various embodiments, the oleaginous yeast is Rhodosporidium toruloides or another species listed in Table 2. In various embodiments, the fungus is a species listed in Table 3.

In various embodiments, the microalgae are of the genera Chlorella and Prototheca, including Chlorella protothecoides and Prototheca moriformis, which are capable of accumulating substantial amounts of triglyceride (e.g., 50 to 85% by dry cell weight). In an embodiment of the present invention, the microorganism is of the genus Chlorella, preferably, Chlorella protothecoides, Chlorella ellipsoidea, Chlorella minutissima, or Chlorella emersonii. Chlorella is a genus of single-celled green algae, belonging to the phylum Chlorophyta. It is spherical in shape, about 2 to 10 µm in diameter, and is without flagella. Some species of Chlorella are naturally heterotrophic. In an embodiment of the present invention, the microorganism is of the genus Prototheca, which are obligate heterotrophs.

TABLE 1

Microalgae.

Achnanthes orientalis, Agmenellum, Amphiprora hyaline, Amphora coffeiformis, Amphora coffeiformis linea, Amphora coffeiformis punctata, Amphora coffeiformis taylori, Amphora coffeiformis tenuis, Amphora delicatissima, Amphora delicatissima capitata, Amphora sp., Anabaena, Ankistrodesmus, Ankistrodesmus falcatus, Boekelovia hooglandii, Borodinella sp., Botryococcus braunii, Botryococcus sudeticus, Bracteoccocus aerius, Bracteococcus sp., Bracteacoccus grandis, Bracteacoccus cinnabarinas, Bracteococcus minor, Bracteococcus medionucleatus, Carteria, Chaetoceros gracilis, Chaetoceros muelleri, Chaetoceros muelleri subsalsum, Chaetoceros sp., Chlorella anitrata, Chlorella Antarctica, Chlorella aureoviridis, Chlorella candida, Chlorella capsulate, Chlorella desiccate, Chlorella ellipsoidea, Chlorella emersonii, Chlorella fusca, Chlorella fusca var. vacuolata, Chlorella glucotropha, Chlorella infusionum, Chlorella infusionum var. actophila, Chlorella infusionum var. auxenophila, Chlorella kessleri, Chlorella lobophora (strain SAG 37.88), Chlorella luteoviridis, Chlorella luteoviridis var. aureoviridis, Chlorella luteoviridis var. lutescens, Chlorella miniata, Chlorella cf. minutissima, Chlorella minutissima, TABLE 1-continued Microalgae.

*Chlorella mutabilis, Chlorella nocturna, Chlorella ovalis, Chlorella parva, Chlorella photophila, Chlorella pringsheimii, Chlorella protothecoides* (including any of UTEX strains 1806, 411, 264, 256, 255, 250, 249, 31, 29, 25), *Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* f. *tertia, Chlorella vulgaris* var. *autotrophica, Chlorella vulgaris* var. *viridis, Chlorella vulgaris* var. *vulgaris, Chlorella vulgaris* var. *vulgaris* f. *tertia, Chlorella vulgaris* var. *vulgaris* f. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena, Franceia* sp., *Fragilaria crotonensis, Fragilaria* sp., *Gleocapsa* sp., *Gloeothamnion* sp., *Hymenomonas* sp., *Isochrysis* aff. *galbana, Isochrysis galbana, Lepocinclis, Micractinium, Micractinium* (UTEX LB 2614), *Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Neochloris oleabundans, Nephrochloris* sp., *Nephroselmis* sp., *Nitschia communis, Nitzschia alexandrina, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella beijerinckii, Parachlorella kessleri, Pascheria acidophila, Pavlova* sp., *Phagus, Phormidium, Platymonas* sp., *Pleurochrysis carterae, Pleurochrysis dentate, Pleurochrysis* sp., *Prototheca stagnora, Prototheca portoricensis, Prototheca moriformis, Prototheca wickerhamii, Prototheca zopfii, Pseudochlorella aquatica, Pyramimonas* sp., *Pyrobotrys, Sarcinoid chrysophyte, Scenedesmus armatus, Scenedesmus rubescens, Schizochytrium, Spirogyra, Spirulina platensis, Stichococcus* sp., *Synechococcus* sp., *Tetraedron, Tetraselmis* sp., *Tetraselmis suecica, Thalassiosira weissflogii,* and *Viridiella fridericiana.*

TABLE 2

Oleaginous Yeast.

*Candida apicola, Candida* sp., *Cryptococcus curvatus, Cryptococcus terricolus, Debaromyces hansenii, Endomycopsis vernalis, Geotrichum carabidarum, Geotrichum cucujoidarum, Geotrichum histeridarum, Geotrichum silvicola, Geotrichum vulgare, Hyphopichia burtonii, Lipomyces lipofer, Lypomyces orentalis, Lipomyces starkeyi, Lipomyces tetrasporous, Pichia mexicana, Rodosporidium sphaerocarpum, Rhodosporidium toruloides Rhodotorula aurantiaca, Rhodotorula dairenensis, Rhodotorula diffluens, Rhodotorula glutinus, Rhodotorula glutinis* var. *glutinis, Rhodotorula gracilis, Rhodotorula graminis Rhodotorula minuta, Rhodotorula mucilaginosa, Rhodotorula mucilaginosa* var. *mucilaginosa, Rhodotorula terpenoidalis, Rhodotorula toruloides, Sporobolomyces alborubescens, Starmerella bombicola, Torulaspora delbruekii, Torulaspora pretoriensis, Trichosporon behrend, Trichosporon brassicae, Trichosporon domesticum, Trichosporon laibachii, Trichosporon loubieri, Trichosporon loubieri* var. *loubieri, Trichosporon montevideense, Trichosporon pullulans, Trichosporon* sp., *Wickerhamyces Canadensis, Yarrowia lipolytica,* and *Zygoascus meyerae.*

TABLE 3

Oleaginous Fungi.

*Mortierella, Mortierrla vinacea, Mortierella alpine, Pythium debaryanum, Mucor circinelloides, Aspergillus ochraceus, Aspergillus terreus, Pennicillium iilacinum, Hensenulo, Chaetomium, Cladosporium, Malbranchea, Rhizopus,* and *Pythium.*

The microalgae may be genetically engineered by introducing an exogenous gene so as to allow the cells utilize an alternate sugar and/or to alter the chain length and saturation profiles of the fatty acids produced by the microalgal cells. For example the cells may use sucrose (e.g., from sugar cane, beets or palm) by recombinant introduction of an exogenous secreted sucrose invertase gene, chain length distribution may be altered through the introduction of an exogenous acyl-ACP thioesterase and/or reduction of endogenous acyl-ACP thioesterase activity (e.g., knockout or knockdown), and saturation profile may be altered through the introduction of an exogenous fatty acid desaturase and/or reduction of endogenous desaturase activity (e.g., knockout or knockdown).

In some embodiments, color-generating compounds (e.g., carotenoids) are present in the microbial biomass at a concentration of no more than 6000 ppm, no more than 5000 ppm, no more than 4000 ppm, no more than 3000 ppm, no more than 2000 ppm, no more than 1000 ppm, 500 ppm, no more than 250 ppm, no more than 100 ppm, no more than 75 ppm, or no more than 25 ppm. Color-generating compounds include carotenoids such as lutein, beta carotene, zeaxanthin, astaxanthin and chlorophyll. In other embodiments, the amount of chlorophyll that is present in the microbial biomass is less than 3500 ppm, less than 3000 ppm, less than 2500 ppm, less than 2000 ppm, less than 1500 ppm, less than 1000 ppm, less than 500 ppm, less than 400 ppm, less than 300 ppm, less than 200 ppm, less than 100 ppm, less than 50 ppm, less than 25 ppm, less than 10 ppm, less than 5 ppm, less than 1 ppm. The amount of chlorophyll that is present in the microbial biomass can range from, e.g., 0.1 ppm to 3000 ppm; this range can be bounded by any of the values in the previous sentence.

Optionally, by using biomass produced from heterotrophically cultivated cells, the resulting compositions may have less color, especially green color, due to lack of chlorophyll. As a result, reduced bleaching or use of lesser amounts of colorants may be required to achieve an article with an acceptable color. Color characteristics may be analyzed by quantification of color according to methods utilizing a three-component theory of color vision. In colorimetry, these components are referred to as X-Y-Z coordinates. Alternatively or in addition, color characteristics may be quantified through the use of spectrophotometry or other methods known in the art.

When processed into compositions such as thermoplastics, thermosets, absorbents, adsorbents, or paper, algal biomass derived from microalgae or microalgae cultivated photosynthetically, such as in ponds, swamps, waste water treatment facilities, or photobioreactors impart a visually unappealing green color to the composition and/or have an unpleasant fishy or seaweed odor. In specific embodiments, the oleaginous microorganism can be cultivated heterotrophically, in the dark. The cells of the microorganism can have less than 2.5% DHA (docosahexaenoic acid); less than 3000 ppm chlorophyll; less than 5000 ppm of color generating compounds; and/or be lacking in an unpleasant odor.

Extraction of Triglycerides.

After growing the cells, triglycerides may be extracted (step 110). Methods for oil extraction, pressing, and cell lysis are given in WO2008/151149, WO2010/063032, WO2010/120939, and WO2010/138620. Oil may be extracted (step 120) by one or more of mechanical pressing, solvent (e.g., hexane) extraction, sonication, or other suitable method. Mechanical pressing methods may optionally include addition of press aid. For example, WO2010/120939 teaches a device and method for pressing of oil from microalgae using a press-aid (also referred to therein as a "bulking agent"). The addition of fibrous pressing aids such as soybean hulls helps extract lipid. Step 120 is optional, in that some of the methods disclosed herein are applicable to whole cells or cells that have low amounts of triglyceride. However, in a preferred embodiment, triglyceride is produced and recovered, followed by utilization of the residual biomass. Where the triglyceride is produced and recovered, typically more than 5% of the dry cell weight is recovered as triglyceride. In certain cases, more than 10%, 15%, 20%, 25%, 30%, 35%, 40%, 45%, 50%, 55%, 60%, 65%, 70%, 75%, 80%, 85%, 90%, 95%, 98% of the dry cell weight may be recovered as triglyceride.

The addition of a press aid or bulking agent may be advantageous in some embodiments of the invention. When there is high oil content and low fiber in the biomass, feeding the biomass through a press can result in an emulsion. This results in low oil yields, because the oil is trapped within the solids. One way in accordance with the methods of the invention to improve the yield in such instances is to add polysaccharide to the biomass in the form of a bulking agent, also known as a "press aid" or "pressing aid". Bulking agents are typically high fiber plant polymer additives that work by adjusting the total fiber content of the microbial biomass to an optimal range. Microbial biomass such as microalgae and the like typically have very little crude fiber content. The addition of high fiber plant polymer additives (in the form of a press aid) may help adjust the total fiber content of the microbial biomass to an optimal range for oil extraction using an expeller press to prepare biomass for a particular application. Optimal fiber content for a typical oil seed may range from 10-20%. In accordance with the methods of the present invention, it may be helpful to adjust the fiber content of the microbial biomass for optimal oil extraction or for a particular application. The range for fiber content in the biomass may be the same or a similar range as the optimal fiber content for a typical oil seed, although the optimal fiber content for each microbial biomass may be lower or higher than the optimal fiber content of a typical oil seed. Suitable pressing aids include, but are not limited to, corn starch, potato starch, cassava starch, switchgrass, rice straw, rice hulls, sugar beet pulp, sugar cane bagasse, soybean hulls, dry rosemary, cellulose, corn stover, dilapidated (either pressed or solvent extracted) cake from soybean, canola, cottonseed, sunflower, jatropha seeds, paper pulp, waste paper and the like. In some embodiments, the spent microbial biomass of reduced lipid content from a previous press is used as a bulking agent. Thus, bulking agents, when incorporated into a biomass, change the physiochemical properties of the biomass so as to facilitate more uniform application of pressure to cells in the biomass.

Biomass Processing

In some embodiments, it may be desirable to further process the biomass following oil extraction (step 130). For example, the biomass may be optionally milled to further reduce particle size of the biomass. The milling step may be achieved through jet milling, hammer milling, bead milling, pearl milling, or another other form of pulverization. In some embodiments, the milled biomass has a particle size of from 0.1 to 300 microns. In some embodiments, the milled biomass has a particle size of from 0.1 to 10 microns, 1 to 8 microns, 2 to 7 microns, or 3 to 6 microns. In some embodiments, the milled biomass has a particle size of less than 10, 9, 8, 7, 6, 5, 4, 3, 2, or 1 micron. In some embodiments the milled biomass has an average particle size about 5 microns. In some embodiments the milled biomass has a particle size of from 10 to 100 microns, 100 to 200 microns, 200 to 300 microns, 300 to 400 microns or 400 to 500 microns. In some embodiments the milled biomass has a particle size of from 10 to 30 microns, 30 to 50 microns, 50 to 70 microns, 70 to 90 microns, 90 to 110 microns, 110 to 150 microns, 150 to 300 microns, or 400 to 500 microns. In some embodiments the biomass has an average particle size of greater than 50, 75, 100, 115, 125, 150, 175, 200, 225, or 250 microns (micrometer).

Biomass may be fractionated to enrich in polysaccharides or to recover proteins, nutrients or other valuable components. Fractionation may comprise washing with a solvent, especially a polar solvent such as water, ethanol or other alcohol, or mixture thereof, and centrifugation or filtration to separate soluble from insoluble fractions. Processing steps may optionally include drying or concentration to obtain biomass for use in one or more embodiments of the present invention. The drying step may be achieved through drum drying, spray drying, freeze drying, oven drying, vacuum drying, tray drying, box drying, or through another method to dry the material. Optionally, the biomass may be further milled to reduce particle size after drying or concentration.

Chemical Modification of Biomass

In an embodiment of the present invention, the microbial biomass is chemically modified through one or more chemical reactions. The modification may be a covalent modification. For example, microbial biomass can be modified through oxidation, ethylation, esterification, halogenation, amination, or carbamoylation. Ethylation reactions may be through alkylation, alkylation with alkyl and aralkyl halides and sulfates, or alkylation with alkylene oxides. Esterification may include nitration, phosphorylation and other reactions leading to phosphorus-containing biomass, sulfation, sulfonation, boration, silylation, acylation, and xanthantion. Non-limiting examples of acylation may include acetylation. Carbamoylation may be through isocyanization. Oxidation may be through epoxidation. Biomass may be chemically altered with hydrophilic moieties. The hydrophilic moieties may be anionic, cationic, zwitterionic, or neutral in charge. Anionic moieties may include carboxylates, sulfates, sulfonates, and phosphates. Cationic moieties may include amines or substituted amines. Neutral moieties may include hydroxyl or alkyl or aryl groups. In various embodiments, the microbial biomass is modified by one or more reactions selected from the group consisting of acylation, hydroxylation, epoxidation, isocyanization, and silylation.

Hydrophobic Esterification

In an embodiment of the present invention, the biomass is modified by the addition of hydrophobic moieties. For example, biomass polymers can be modified to contain hydrophobic groups by reaction with activated carbonyl-bearing molecules having both carboxylic acid groups and hydrophobic moieties. The reactive molecules may be of the form of structure 1: $R_1(C=O)R_2$ (compound 1), where $R_1$ is a leaving group and $R_2$ is a hydrophobic moiety. Nucleophilic groups of the biomass will covalently bond to the carbonyl carbon of 1. The nucleophilic groups can be hydroxyl and/or amine groups of polysaccharides, exopolysaccharides, proteins, or other biopolymers in the biomass; as a result, the biomass will be modified with the hydrophobic moieties via esterification and/or amidation reactions. Compound 1 can be an acid halide such as acetyl chloride, or an anhydride, such as acetic anhydride. Although, in part due to cost, acetylation is one embodiment (i.e., $R_2$=methyl), biomass polymers can be covalently modified to contain longer chain acid groups where $R_2$ is a 2 to 20 carbon alkyl group, preferable of 2 to 5 carbons. Structure 1 can also be an activated C8 to C20 saturated or unsaturated fatty acid, such as those produced biologically (including by the cells that produced the biomass, and further including fatty acids having tailored chain length and/or saturation profiles due to genetic engineering of the biomass).

As a result of the hydrophobic modification, the biomass polymers become more resistant to solvation by water. As described below, esterified biomass, and acetylated microalgal biomass in particular has been found to possess useful thermoplastic properties and may be advantageously incorporated into useful objects including packing materials, bottles and containers, films, bags, coatings, and tableware, including biodegradable or compostable objects. Due to the hydrophobic modification, the polymers can be internally plasticized; i.e., less external plasticizer is needed for use in a thermoplastic material.

An illustrative procedure for acetylation of the biomass is adapted from the recipe for producing starch triacetate given in U.S. Pat. No. 3,795,670. Microalgal biomass is suspended in a solution of acetic acid and one to eight equivalents of acetic anhydride. Aqueous sodium hydroxide is added as a catalyst. The mixture is heated for about one to ten hours at 130-140° C. Acetylated biomass is purified from the mixture by cooling and pouring the cooled reaction mixture into water to separate a precipitate, which is further washed with water until the wash water achieves neutral and then dried. The resulting degree of acetylation may be in the range of 1.0 to 3.0, 1.5 to 3.0, or 1.6 to 2.5, or 0.25 to 3.0 as measured by DS value (the "degree of substitution", measured as the ratio of spectroscopic peak intensity for the functional groups vs. unmodified backbone signals), or in the range of 15% to 100% or 20% to 80% as measured by cleavage and quantification of the acetyl groups.

In an embodiment, the biomass used can be purified to remove soluble components and enrich in insoluble protein and polysaccharide containing components. For example, the biomass may be washed one or more times with a polar solvent such as ethanol or water and centrifuged prior to acetylation. In some embodiments, it has been found that using washed biomass prior to acetylation gives superior thermoplastic thermal properties, as disclosed in the examples below.

Other compounds of structure 1 can be produced by a similar procedure or other procedures known in the art. In an embodiment, the covalently modified biomass is biodegradable or compostable. In a further embodiment, the biomass is biodegradable or compostable. In a particular embodiment, the biomass is compostable according to ASTM D6400-04 Standard Specification for Compostable Plastics.

In an embodiment, esterification of the biomass creates a plasticizer, which may substitute in whole or in part for added plasticizers such as those listed above. For example, the biomass may contain residual lipid, glycerol, or monoglycerides, diglycerides, and triglycerides, or a combination thereof, which, when acetylated or otherwise esterified with other molecules of structure 1, may have plasticizing activity.

Anionization

An alternate or additional modification to the microalgal biomass is anionization. Anionization is the covalent addition of anionic moieties to polysaccharides present in the biomass. For example, the polysaccharides may be covalently modified with carboxylate, sulfonate, or phosphate moieties. In the illustrative examples given below, the polysaccharide is modified with carboxymethyl groups to form $RCH_2COOH$ groups (or the corresponding anion, $RCH_2COO^-$ at an appropriate alkaline (basic) pH), where R represents a polysaccharide, linked via one or both of a hydroxyl group, or amine group (as can be the case for a polysaccharide having a glucosamine or other amino sugar monomer). The biomass may be prepared as described above, including with a step of purifying an insoluble biomass fraction, either before or after anionization. The anionized polymers so formed can be used in numerous applications including drilling muds, as a component of paper, or in an absorbant in diapers, hygienic or other personal-care product. Furthermore, the biomass can be crosslinked, either before or after anionization to make a cross-linked anionized polymeric material. In a specific embodiment, the cross-linked anionized polymeric material is plasticized and formed into a structural material, such as a biodegradable flower pot.

Anionization may be performed using methods known in the art for anionization of polysaccharides, including starch and cellulose. Microalgal biomass is prepared as for the esterification reactions described above. In an embodiment, the microalgal biomass is washed with a polar solvent such as water or ethanol, leaving an insoluble fraction. Carboxymethylation may then be performed on the biomass, and in some embodiments, cross-linking. For example, the biomass may be reacted with chloroacetic acid in the presence of a base such as sodium hydroxide, as is performed in the art for carboxymethylation of starch. The biomass can also be reacted with a halogen derivative of a dibasic hydroxy-acid (e.g., as taught in U.S. Pat. No. 4,000,127).

In one embodiment, carboxymethylation is performed with high consistency according to the teachings of U.S. Pat. No. 7,932,378 and/or U.S. Pat. No. 7,662,953.

Chemically modified biomass may be further processed to facilitate formulation, incorporation, or blending with other materials to produce a paper, absorbent, or thermoplastic composition. Processing steps such as drying and milling may alter the particle size, particle morphology, surface area, or other property of the chemically modified biomass in a manner that enables or improves its use with materials to produce a paper, absorbent, or thermoplastic composition. Processing steps such as drying and milling may alter the particle size, particle morphology, surface area, or other property of the chemically modified biomass in a manner that improves the mechanical or physical performance of a paper, absorbent, or thermoplastic composition produced with the processed, chemically modified biomass. For example, carboxymethylated, crosslinked microalgal biomass may be dried though freeze drying methods to produce an absorbent composition with improved water and saline absorbency capacity as the same carboxymethylated, crosslinked microalgal biomass dried through vacuum oven drying methods. See Examples 20 and 22.

General Use of Microalgal Biomass in Thermoplastics and in Thermosets

Biomass or covalently modified biomass may be compounded with other plasticizing materials to produce a readily moldable thermoplastic material. For example, the biomass or covalently modified biomass may be compounded with one of more of glycerol, sorbitol, triacetin, triethyl citrate, acetyl triethyl citrate, tributyl citrate, acetyl tributyl citrate, trioctyl citrate, acetyl trioctyl citrate, trihexyl citrate, butyryl trihexyl citrate, trimethyl citrate, alkyl sulphonic acid phenyl ester, or 1,2-cyclohexane dicarboxylic acid diisononyl ester. Optionally, plasticizers are biodegradable.

Furthermore, the biomass or covalently modified biomass may be blended with an additional thermoplastic polymer material, optionally a biodegradable or compostable polymer. For example, the polymeric material may be a polyester such as polylactic acid (PLA) and its copolymers, polycaprolactone, polybutylene succinate, polybutylene succinate-adipate, a compostable or non-compostable aliphatic-aromatic polyester, polyesteramide, polyethylene, polypropylene, polyethylene terephthalate, polycarbonate, or a polyhydroxyalkanoate (including polyhydroxybutyrate and polyhydroxybutyrate-co-valerate), an aliphatic polyester-based polyurethane, polyvinyl alcohol, polyvinyl chloride, poly(ethylene) vinyl acetate, polystyrene, a starch or cellulose ester (including acetates, acetate-butyrates, and acetate-proprionates), or a combination of any of the above. See U.S. Pat. No. 5,939,467. In some embodiments, the thermoplastic polymer material is grafted with maleic anhydride. Such materials include maleic anhydride grafted polylactic acid, maleic anhydride grafted polyethylene, and maleic anhydride grafted polypropylene. The additional thermoplastic material can be present in any useful amount, including the range of 10 to 90%, 20 to 70%, 30 to 60%, 40-50%, 10-20%, or 20-30% by mass.

Aliphatic-aromatic copolyesters may be employed in the composition such as those generated through any known technique including the condensation polymerization of a polyol in conjunction with aliphatic and aromatic dicarboxylic acids, esters, or anhydrides thereof. The polyols may be substituted or unsubstituted, linear or branched. The aromatic dicarboxylic acids may be substituted or unsubstituted, linear or branched. In a particular embodiment, blending with PLA or PLA copolymers may increase the useful temperature range of a melt-processed product made from the blend. For example, a composition comprising PLA and acetylated microalgal biomass may be used as an internal liner of a paper hot-beverage cup.

Chemically modified oleaginous microbes, preferably chemically modified microalgae may also increase the ductility, elongation at break under tensile stress, or deformation temperature of PLA in a blend. For example, a composition comprising PLA and acetylated microalgal biomass may be useful in lining of cables, cords, or tubing.

Different grades of PLA are suitable for different applications or processing conditions. Non-limiting examples of PLA grades suitable for use with the microalgal biomass of this invention include NatureWorks 2002D, 2003D, 3001D, 3051D, 3052D, 3251D, 3801X, 4032D, 4042D, 4043D, 4050D, 4060D, 6060D, 6201D, 6201D, 6204D, 6251D, 6252D, 6302D, 6350D, 6400D, 6752D, 7000D, 7001D, 7032D, 8052D, 8251D, and 8302D.

In an embodiment, the biomass or covalently modified biomass is compounded with both a plasticizer and a second polymer or a plasticized second polymer.

The strength of thermoplastic compositions made with biomass or covalently modified biomass (alone or compounded/blended) may be further increased by the addition of fibers. Fibers may optionally be biodegradable such as may be obtained from cellulosic or woody plant materials. Rigidity (modulus) may also be improved by addition natural silicate fibers or of talc or other mineral fillers. In an embodiment, the fibers used, fiber content and processing temperature are chosen to obtain a Young's modulus of 680-6100 MPa and tensile strength of 8-46 MPa.

In an embodiment, the fibers are present in the biomass from which the covalently modified biomass is derived. The fibers may be from plant polymers used as a press-aid for the extraction of lipid or other valuable material from the cells. For example, WO2010/120939 teaches a device and method for pressing of oil from microalgae using a press-aid (also referred to therein as a "bulking agent"). The addition of fibrous pressing aids such as soy hulls helps extract lipid. These pressing aids then remain mixed with the biomass and may be further homogenized to break the pressing aids into smaller fibrous entities which when processed into a thermoplastic as previously described, will impart additional properties to the thermoplastic article formed. In an embodiment, the press-aid is present in the biomass or covalently modified biomass at a concentration of 0.1 to 30% by weight. In the case of acetylation treatment, this procedure may also acetylate fibers of the press-aid, further improving internal plasticization.

The microbial biomass, covalently modified biomass, or blended compositions may also further be blended with a cross-linking agent and/or inert fillers (e.g., calcium or zirconium salts, lignine, silicate, or aluminate). Non-limiting examples of crosslinking agents include acrylates, amides, imides, anhydrides, isocyanates, silanes, titanates, maleic anhydride, peroxides, epichlorohydrin, triallyl isocyanurate, epoxy functional products such as supplied by BASF under the trade name Joncryl®, as well as ionic crosslink agents including Surlyn® provided by DuPont. Crosslinking may optionally be achieved through exposure to ultraviolet wavelengths.

The microbial biomass, covalently modified biomass, or blended compositions may also further be blended with surfactants. As described here a surfactant is a compound such as a detergent or wetting agent that affects the surface tension of a fluid. Non-limiting examples of surfactants suitable for use with embodiments of this invention include glyceryl monostearate, ethoxylated dimethylsiloxane, polyoxyethylene, propylene oxide, organic sulfates, organic sulfonates, alkyl polyglycosides, and polyolefin glycols.

The microbial biomass, covalently modified biomass, or blended compositions may also further be blended with antioxidants. Non-limiting examples of antioxidants suitable for use with embodiments of this invention are those such as supplied by Chemtura under the trade names ANOX®, ULTRANOX®, ALKNOX®, and NAUGARD® as well as those supplied by BASF under the trade name Iragfos®. In an embodiment, addition of one or more antioxidant to a thermoplastic blend comprising microbial biomass may increase the operating temperature of the composition. In a further embodiment, addition of one or more antioxidant to a thermoplastic blend comprising microbial biomass may decrease darkening of the thermoplastic composition.

The microbial biomass, covalently modified biomass, or blended compositions may also further be blended with an elastomer.

In an embodiment, the specific gravity of a thermoplastic composition prepared through blending one or more thermoplastic polymers with microbial biomass or covalently modified biomass does not increase or does not significantly increase. Low or no increases in specific gravity is a desirable benefit for applications requiring light weight component parts, such as automobile components and casings for electronic equipment. In some embodiments the specific gravity of a thermoplastic or thermoset composition increases by less than 10%, less than 5%, less than 2%, or less than 1% when as much as 5%, 10%, 15%, 20%, 25%, 30%, 35%, 40%, 45%, or 50% by weight of a thermoplastic polymer is replaced with single-celled oleaginous microbial biomass, such as microalgal biomass, to form a blend.

Articles may be melt processed using the thermoplastic compositions. For example, articles may be injection molded, compression molded, blow molded, thermoformed, coated onto paper, rotomolded, fused molded, or made by cast-film or blown-film methods. Articles may be used in laminating or in baked-on coating. Articles may be spun such as by melt spinning, rotary jet spinning, electrospinning, ring spinning or through other methods known in the art.

The biomass and the compositions or articles made with the biomass may be biodegradable or compostable in accordance with one or more of the following standards: ASTM D6400-04, ASTM D7071-05, ASTM D5988-03, ASTM D5511-11, ASTM D6954-04, ASTM 7475-11, ISO 1485502; 2007, ISO 14853:2005, ISO 14855-1:2005.

Thermal properties. The glass transition temperature of the acetylated biomass or blends thereof may be above 50° C., above 60° C., above 75° C. above 100° C., or above 140° C. (especially for acetylated washed biomass). The degradation temperature at 10% loss of weight may be above 230° C., preferably above 250° C., and preferably above 300° C. In the case of acetylated washed algae the degradation temperature may be about 290° C., about 305° C., or about 315° C.

The resulting plastic material may have one or more of the following properties:

(a) a Young's modulus of 300-3000 MPa, 200-3500 MPa, 2500-3000 MPa, or 300-2800 MPa;
(b) a tensile strength of 5-70 MPa, 5-90 MPa, 10-85 MPa, or 20-60 MPa;
(c) a tensile strength at maximum load of 5 to 100 MPa, 5-50 MPa, 10-90 MPa, or 20-90 MPa;
(d) ultimate elongation of 1-400%, 1-300%, or 2-250%;
(e) a tear strength of film of 2-10 N/mm more typically 2-8N/mm;
(f) a specific gravity of 0.8 to 1.5 g/cm$^3$, 0.9 to 1.35 g/cm$^3$, or 0.95 to 1.25 5 g/cm$^3$;
(g) a notched izod impact of 10-530 J/m, 10-400 J/m, 15-350 J/M, or 16-300 J/m; and/or
(h) an un-notched izod impact of 1-30 (ft-lb)/in, 1.5-10 (ft-lb)/in, or 3-20 (ft-lb)/in.

In an embodiment, heterotrophic oleaginous microalgae are cultivated, then pressed with press aids to remove oil and the resulting biomass containing press aid fibers is compounded with one or more of a plasticizer, a surfactant, a flame retardant, an antioxidant, a compatibilizer, an elastomer, and a second polymer to produce a thermoplastic. In a further embodiment, heterotrophic oleaginous microalgae are cultivated, pressed with press aids to remove oil, the resulting biomass containing press aid fibers is covalently modified, and the covalently modified biomass is compounded with one or more of a plasticizer, a surfactant, a flame retardant, an antioxidant, an elastomer, a compatibilizer, and a second polymer to produce a thermoplastic.

More generally, an embodiment of the present invention features cultivating oleaginous microalgae, obtaining oil from the microalgae optionally using a press aid, homogenizing the biomass and producing a plastic from the biomass. The plastic production step may use techniques disclosed here or those known in the art.

Use of Triglyceride Containing Microalgal Biomass

In an additional embodiment of the invention, the biomass includes a certain percentage of triglyceride. The optional triglyceride recovery step in the biomass processing method is not performed, or it is partially performed. Where it is partially performed, the recovered triglyceride amounts to less than 2.5% of the biomass dry cell weight. In certain cases, the recovered triglyceride amounts to less than 0.25%, 0.5%, 1%, 5%, 10%, 15%, 20%, 25%, 30%, 35%, 40%, 45%, 50%, 60%, 70%, 80%, or 90% of the dry cell weight.

The triglyceride containing biomass may then be compounded with other plasticizing materials (examples listed above) to produce a thermoplastic material. As with the acetylated biomass, the triglyceride containing biomass may be blended with one or more additional thermoplastic polymer materials, optionally a biodegradable or compostable polymer. The strength of the esterified biomass (alone or compounded/blended) may be further increased by the addition of fibers, optionally biodegradable such as may be obtained from cellulosic or woody plant materials.

Combination of Biomass with Plant Polymers

In another embodiment of the invention, the biomass is combined with at least one type of plant polymer to provide a blend. The blend may then be compounded with other plasticizing materials to produce a readily moldable thermoplastic material.

Plant polymers used in the blend are renewable polymeric materials, such as proteins or starches. The plant polymer is typically present in the blend in a weight percentage ranging from approximately 10 weight percent to 50 weight percent. Such polymers typically include at least 50 percent protein. Protein-based plant polymers include, without limitation, water insoluble fractions from: corn, gluten, wheat gluten, zein, canola, sunflower, sorghum, soybean, and combinations thereof. Starch-based plant polymers include, without limitation, fractions from: corn, waxy corn, wheat, sorghum, rice, waxy rice, potatoes, tapioca, sweet potato, arrowroot, pith of sago palm, and combinations thereof. In various embodiments, the one or more plant polymers is from the group consisting of switchgrass, rice straw, sugar beet pulp, corn starch, potato starch, cassava starch, sugar cane bagasse, soybean hulls, dry rosemary, cellulose, corn stover, dilapidated cake from soybean, canola, cottonseed, sunflower, jatropha seeds, paper pulp, and waste paper.

Examples of plasticizing materials with which the blend may be compounded include one of more of glycerol, sorbitol, triacetin, triethyl citrate, acetyl triethyl citrate, tributyl citrate, acetyl tributyl citrate, trioctyl citrate, acetyl trioctyl citrate, trihexyl citrate, butyryl trihexyl citrate, trimethyl citrate, alkyl sulphonic acid phenyl ester, or 1,2-cyclohexane dicarboxylic acid diisononyl ester. Plasticizers may be biodegradable.

The blend and plasticizer composition may be further blended with thermoplastic polymer materials, optionally biodegradable or compostable polymers. For example, the polymeric material may be a polyester such as polylactic acid (PLA) and its copolymers, polycaprolactone, polybutylene succinate, polybutylene succinate-adipate, a compostable or non-compostable aliphatic-aromatic polyester, polyesteramide, polyethylene, very low density polyethylene, low density polyethylene, linear low density polyethylene, medium density polyethylene, high density polyethylene, ultra high molecular weight polyethylene, polypropylene, polyethylene terephthalate, polycarbonate, or a polyhydroxyalkanoate (including polyhydroxybutyrate and polyhydroxybutyrate-covalerate), an aliphatic polyester-based polyurethane, polyvinyl alcohol, polyvinyl chloride, a starch or cellulose ester (including acetates, acetate-butyrates, and acetate-proprionates), or a combination of any of the above. See U.S. Pat. No. 5,939,467. The additional thermoplastic material can be present in any useful amount, including the range of 10 to 90%, 20 to 70%, 30 to 60%, 40-50%, 10-20%, or 20-30% by mass. In a particular embodiment, blending with PLA may increase the useful temperature range of a melt-processed product made from the blend. For example, a film comprising PLA, the blend and plasticizer may be used as an internal liner of a paper hot-beverage cup. The blend and plasticizer composition may also increase the ductility, elongation at break under tensile stress, or deformation temperature of PLA in a blend.

Thermoplastic polymers traditionally derived from petroleum-based feedstocks may optionally be synthesized using component molecules obtained through renewable methods. For example, "green" polyethylene may be derived from microbial conversion of sugars. Similarly, other co-polymers may comprise butene obtained by the dehydration of a bio-based butanol produced through the fermentation of sugars. Gasification of biomass can also produce polyethylene or polypropylene.

In an additional embodiment, blending microalgal biomass with high density polyethylene (HDPE) may increase the useful temperature range of a melt-processed product made from the blend. For example, a molded composition comprising HDPE and microalgal biomass may be used as plastic fuel tank or other chemically-resistant container. The modified or unmodified microalgal biomass can be present in any useful amount, including the range of 2 to 60%, 5 to 40%, 10 to 39%, 40-49%, 10-20%, or 20-30% by mass.

In an embodiment, the biomass and plant polymer blend is compounded with both a plasticizer and a second polymer or a plasticized second polymer. The strength of the blend, as with the esterified biomass, may be increased by the addition of fibers, optionally biodegradable such as may be obtained from cellulosic or woody plant materials. The blended compositions may also be combined with a cross-linking agent and/or inert fillers (e.g., calcium or zirconium salts, lignine, silicate, or aluminate).

As described below microalgal biomass has been shown to possess useful thermoplastic properties and may be advantageously incorporated into useful objects including biodegradable or compostable objects, such as packing materials, bottles and containers, films, labels, adhesive labels, bags, coatings, tableware, toys, handles for items such as razors, scissors, cooking utensils, and tools, components of shoes, luggage, and backpacks, frames for glasses and sunglasses, jacket casings for cables and wires, housing elements for electronics such as computers, phones, cameras, printers, photocopiers, stereos, and clocks, as well as automobile, airplane, and rail parts including objects for passenger vehicle interiors.

Anionization of Algae.

An alternate or additional modification to the microalgal biomass is anionization. Anionization is the covalent addition of anionic moieties to polysaccharides present in the biomass. For example, the polysaccharides may be covalently modified with carboxylate, sulfonate, or phosphate moieties. In the illustrative examples given below, the polysaccharide is modified with carboxymethyl groups to form $RCH_2COOH$ groups (or the corresponding anion, $RCH_2COO^-$ at an appropriate alkaline (basic) pH), where R represents a polysaccharide, linked via one or both of a hydroxyl group, or amine group (as can be the case for a polysaccharide having a glucosamine or other amino sugar monomer). The biomass may be prepared as described above, including with a step of purifying an insoluble biomass fraction, either before or after anionization. The anionized polymers so formed can be used in numerous applications including drilling muds, as a component of paper, or in an absorbant in diapers, hygienic or other personal-care product. Furthermore, the biomass can be crosslinked, either before or after anionization to make a cross-linked anionized polymeric material. In a specific embodiment, the cross-linked anionized polymeric material is plasticized and formed into a structural material, such as a biodegradable flower pot.

Anionization may be performed using methods known in the art for anionization of polysaccharides, including starch and cellulose. Microalgal biomass is prepared as for the esterification reactions described above. In an embodiment, the microalgal biomass is washed with a polar solvent such as water or ethanol, leaving an insoluble fraction. Carboxymethylation may then be performed on the biomass, and in some embodiments, cross-linking. For example, the biomass may be reacted with chloroacetic acid in the presence of a base such as sodium hydroxide, as is performed in the art for carboxymethylation of starch. The biomass can also be reacted with a halogen derivative of a dibasic hydroxy-acid (e.g., as taught in U.S. Pat. No. 4,000,127).

In one embodiment, carboxymethylation is performed with high consistency according to the teachings of U.S. Pat. No. 7,932,378 and/or U.S. Pat. No. 7,662,953.

In an embodiment the degree of carboxymethylation is 0.5 to 3.0, 0.5 to 2.0, 0.5 to 1.5, or 0.25 to 3. As a result, the material may have a favorable propensity to absorb water. For example, the degree of absorbency may be 100 to 4000%, 100-3000%, 100-2000%, 500-3000%, or 500-2000% by weight. In various embodiments, the absorbant compositions can absorb at least 5 times, e.g., at least 10 times, at least 20 times, at least 50 times, at least 100 times, at least 200 times, or more, of its weight in liquid. The carboxymethylated microalgal biomass may then be used in various applications, including use in oil-field drilling fluids.

Anionized microalgal biomass may be plasticized and formed into objects. For example, the anionized biomass may be formulated with water and/or glycerol as a plasticizer followed by heating and shaping. The anionized and plasticized biomass may be compression or injection molded.

Optionally, the biomass is crosslinked, either before, after, or contemporaneously with the carboxymethylation step. One method for crosslinking is reaction with glyoxal.

Suitable crosslinking agents for use in embodiments of the invention include aldehydes, C2-C8 dialdehydes, glyoxal, C2-C9 polycarboxylic acids, maleic anhydride, epichlorhydrin, divinyl sulphone, ethylenediamine, cystamine dihydrochloride, acrylic acid, sorbitan monolaurate, polyethylene glycol, sodium zirconium lactate, sodium borate, genipin, and sodium stearate. Crosslinking may be achieved through other methods known in the art including exposure to ultraviolet wavelengths. Also see U.S. Pat. Nos. 2,639,239; 3,723,413; 3,345,358; 4,689,408, 6,765,042, and 7,485,719, which disclose methods for anionizing and/or cross-linking.

Crosslinked, anionized microalgal biomass may be plasticized and formed into objects. For example, the crosslinked, anionized biomass may be formulated with water and/or glycerol as a plasticizer followed by heating and shaping. The crosslinked, anionized and plasticized biomass may be compression or injection molded.

Biomass prepared with or without additional plant polymers and optionally unmodified, crosslinked, and/or covalently modified may optionally be combined with one or more additional absorbent polymers, such as polyacrylate, polyacrylamide, polyvinyl alcohol, starch, starch-g-polyacrylonitrile, cellulose, carboxymethyl cellulose, and hydroxyethyl cellulose to produce an absorbent composition. Covalently modified microbial biomass may be useful in an absorbent application for the absorbance, retention, or removal of liquids such as water, saline, oil, urine, or blood or any combination thereof.

As described below, microalgal biomass has been shown to possess useful absorbent properties and may be advantageously incorporated into useful objects including biodegradable or compostable objects, such as diapers, wipes, hygienic products, filters, berms, and packaging materials.

Use of Cationic Retention Aids with Algae.

The use of cationic retention aids involves the addition of one or more cationic retention aids (e.g., polyacrylamides) to the biomass. The use of cationic retention aids which causes the agglomeration of suspended particles through a bridging mechanism is used to increase the retention of the microalgal biomass when manufacturing paper products. This is especially useful in the production of tissue products, where the microalgal biomass, which is optionally flocculated, and the cationic retention aid is combined with conventional papermaking fibers in a typical tissue production method.

Examples of cationic retention aids that may be combined with the microalgal biomass include one or more of: polydiallyldimethylammonium chlorides, branched polyacrylamides, polyamines having a molar mass of more than 50,000, modified polyamines grafted with ethylenimine, crosslinked polyetheramides, polyvinylimidazoles, polyvinylpyrrolidines, polyvinylimidazolines, polyvinyltetrahydropyrines, poly(dialkylaminoalkylvinylethers), poly(diakylaminoalkyl (meth)acrylates) in protonated or quaternized form, polyamidoamines obtained from a dicarboxylic acid, polyalkylenepolymines grafted with ethylenimine and crosslinked with polyethylene glycol dichlorohydrin ether, polyamidoamines reacted with epichlorohydrin to give water-soluble condensates, cationic starches, alum, polyaluminum chloride, and combinations thereof.

Where the microalgal biomass is flocculated, the flocculating agents may be selected from starches, modified starches (e.g., cationic or amphoteric starch), cellulose ethers (e.g., carboxyemethyl cellulose (CMC) and derivatives thereof, alginates, cellulose esters, ketene dimers, succinic acid or anhydride polymers, natural gums and resins (especially mannogalactans, e.g., guar gum or locust bean gum) and the corresponding modified (e.g., cationic or amphoteric) natural gums and resins (e.g., modified guar gum), proteins (e.g., cationic proteins) such as soybean protein, poly(vinyl alcohol), poly(vinyl acetate) such as partially hydrolyzed poly(vinyl acetate).

One technique that may be employed for making the tissue product involves a wet-end stock system. See, U.S. Pat. No. 6,027,611. A cationic flocculating agent (e.g., 1 to 5 weight percent) is typically used to flocculate the microalgae in such a system. The retention aid is added at any point between the wet-end stock system chest and headbox, typically at a level of 0.1 to 1.5 pounds per metric ton of dry fiber.

Hydrothermal Carbonization ("HTC") of Algae.

Another use for the microalgal biomass or fraction thereof is carbonization to produce a carbonized material. The carbonized material may be useful as an adsorbant. First, a micoalgal biomass starting material is prepared according to one the procedures mentioned above. Optionally, an insoluble fraction of the microalgal biomass is isolated by washing the microalgal biomass with a polar solvent such as water or alcohol. In an embodiment, the starting material includes an acidic carbonization catalyst such as citric acid or acrylic acid. When included, these materials act as a carbonization catalyst and can provide carboxyl groups to the final carbonized material, which, among other benefits, can increase the propensity of the carbonized material to bind metals.

The starting material is then hydrothermally carbonized by heating in the presence of water, and optionally, an acidic catalyst to between about 180-350° C. for any sufficient period of time, and optionally between 180-300° C. for between 60 to 180 minutes, to effect carbonization. Carbonization of microalgal biomass can produce highly structured materials with large surface areas.

In an embodiment, the acidic additive is added in the range of 0.01 to 0.6 grams and optionally 0.03 to 0.4 g per gram of microalgal biomass (by dry weight).

Material produced in this way may be useful as an adsorbent material for the purification of air, water, chemicals, or other substances, as a fuel, or as biochar to improve agricultural fertility. Adsorbents purify substances including organic molecules, and metals or metal ions by adsorbing contaminants from the substance to be purified into the matrix of the carbonized microalgal biomass. For example, a waste solvent (e.g., water) stream containing heavy metal contaminants, such as palladium, cadmium, mercury, lead or any other metal contaminants can be purified by contacting the waste water with the carbonized microalgal biomass of the invention. The metal cations of the waste water are adsorbed into the carbonized microalgal biomass and the concentrations of the metal cations are reduced in the waste water. Similarly, any other cations, for example, $NH_4^+$, $Fe^{(+2, +3, or +4)}$, $Cu^{(+2 or +3)}$, $As^{+3}$ or any other cation can be decontaminated with carbonized microalgal biomass. The decontaminated water can be recycled or discharged into the sewer system.

The microalgae may contain nitrogen (N), phosphorous (P) and/or potassium (K) which are vital elements in fertilizers. The recovery of these elements from the aqueous phase could further improve the economy of the process. Elemental analysis of hydrothermal carbonization filtrates showed that phosphorous and potassium from the microalgae were almost entirely enriched in the aqueous phase whereas significant amount of nitrogen remained in the solid or gas phase. In an embodiment, the carbonized material is collected and nutrients in the aqueous or gas phases of the reaction are reclaimed. The nutrients can be added to culture medium to produce more microalgae and/or can be used as agricultural fertilizer, including to fertilize sugar-producing crops from which sugar is then obtained and used to feed the microalgae. In either case, the process of producing microalgae and high value products from the microalgae can require much lower levels of nutrients; phosphorous and potassium in particular. Thus, these elements may be viewed as catalytic in the conversion of sugar feedstock into microalgal products such as lipids. The water and gas phases remaining after carbonization have been found to be a rich source of available nutrients.

In an embodiment, microalgal triglyceride is extracted from microalgae in a manner that leaves residual triglyceride in the biomass (e.g., by mechanical pressing of the algae). The residual biomass in then carbonized by HTC under conditions in which the triglycerides remain intact or are hydrolyzed to fatty acids. The fatty acids or triglyceride are then recovered. For example, fatty acids or triglyceride can be extracted with hexane, diethyl ether, dioxan, isopropyl ether, tetrahydrofuran, ethanol, methanol, chloroform, diochloromethane, or a mixture of solvents.

General Use of Microalgal Biomass in Paper.

In addition to being useful for producing tissue products, the microalgal biomass or fraction thereof may be generally used as a fibrous or filling material in the production of paper. The use of the microalgal biomass can replace more expensive pulp and may have salutary effects on the resulting paper, such as increased wet-strength.

Microalgal biomass, prepared with or without a bulking agent may be added to or replace more other papermaking fibers. Papermaking fibers may contain any natural or synthetic cellulosic fibers including but not limited to nonwoody fibers, such as cotton, bamboo, abaca, kenaf, sabai grass, flax, esparto grass, straw, hemp, jute hemp, bagasse, milkweed floss fibers, and pineapple leaf and woody or pulp fibers such as those obtained from deciduous and coniferous trees, including softwood fibers, such as northern and southern softwood kraft fibers; and hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. Papermaking fibers may be synthetic fibers such as rayon, polyolefin fibers, polyester fibers, bicomponent sheath-core fibers, or multi-component binder fibers. Other papermaking fibers may include paper broke or recycled fibers and high yield fibers. Papermaking fibers may include without limitation those produced by pulping processes such as bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps.

As described below, microalgal biomass has been shown to possess useful properties when incorporated into paper applications and may be advantageously utilized into paper compositions including biodegradable or compostable paper products such as tissue paper, toilet paper, paper towels, napkins, wrapping paper, cardboard, carton packaging, butcher paper, waxpaper, newspaper, bulk paper, writing paper, envelopes, and tubing.

EXAMPLES

Example 1

Wet Fractionation of Microalgal Biomass

For wet fractionation, dry, lysed, *Prototheca moriformis* microalgal biomass (5.4 kg) from which oil had been extracted was suspended in distilled water at a concentration of about 3% and warmed up to 50° C. in a steel tank. Treatment time was 2 hours while occasionally stirring. Thereafter the solution was fed (180-200 L/h) to a centrifuge (Alfa Laval) for separation of the insoluble and soluble fractions. The insoluble fraction (27.5 kg wet weight) was further spray dried to a final dry yield of 2.6 kg (48% of algal dry biomass). The soluble fraction (about 100 liters) was concentrated with a Millipore ultrafiltration unit having a membrane cut-off of 5 kDa and a total surface area of 4 m$^2$. The retentate (polymeric fraction, about 24 L) and part of the permeate (low MW components) were collected.

Example 2

Acetylation of *Prototheca moriformis* Microalgal Biomass

The acetylation of *Prototheca moriformis* biomass was performed as described in U.S. Pat. No. 3,795,670. Acetylation was performed for unwashed biomass and for the insoluble fraction obtained in Example 1. Lysed and dilapidated microalgal biomass was suspended in a mixture of acetic acid and several equivalents of acetic anhydride. Aqueous sodium hydroxide was added as a catalyst. The mixture was heated for several hours at 130-140° C. The purification was performed by pouring the cooled reaction mixture into water and separation of the precipitate. The precipitate is further washed with water until neutral. The product was air dried. The acetyl content before and after modification was evaluated by cleavage of the acetyl groups and quantification of the released acetic acid by titration. Because the microalgae biomass is a heterogeneous mixture of polysaccharides, protein and small molecular components, the degree of acetylation was evaluated according to the acetyl content (%-m) of the material instead of DS. Three batches of acetylated algae were prepared (Table 4). A higher degree of acetylation could be reached when 'washed' algae without small molecular water soluble material was used instead of unwashed algae. In both cases, the algae feedstock contains lipid residues (as determined by stained fluorescent microscopy).

TABLE 4

| Batch | Starting Material | Amount of feedstock (g) | Yield of Product (g) | Acetyl content %-m |
|---|---|---|---|---|
| Control (no treatment) | Unmodified biomass | — | — | 10 |
| 1 | Unmodified biomass | 50 | 51 | 38 |
| 2 | Washed biomass insoluble fraction of Example 1 | 100 | About 100 | 45 |
| 3 | Washed biomass insoluble fraction of Example 1 | 600 | 785 | 42 |

Example 3

Thermal Properties of Acetylated Biomass

Differential Scanning calorimetry (DSC) measurements of various acetylated samples of Example 2 and control samples was performed. No clear glass transition temperature could be found for the algae or 'washed' algae feedstocks of Example 2 due to the several overlapping thermal transitions of the algae components (lipids, proteins, polysaccharides). In acetylated algae, the $T_g$ was about 60° C. A higher $T_g$ of 140° C. was found for the acetylated 'washed' algae. For acetylated 'washed' algae the glass transition temperature was clearly higher compared to PLA, and blending of acetylated algae with PLA thus increases the temperature range of PLA products. Due to PLA's relatively low glass transition temperature, for example the PLA cups cannot hold hot liquids, and much research is focused on development of heat resistant PLA.

Thermal stability of the algae increases with acetylation, and can be further increased by the removal of small molecular components by washing of algae before acetylation. $T_{deg}$ is the temperature at which there is 10% loss of weight of the material at the indicated temperature.

TABLE 5

| Sample | $T_g$ (° C.) | $T_{deg}$ (° C. at 10% loss of weight) |
|---|---|---|
| Microalgal biomass | Not resolved | 225 |
| Acetylated microalgal biomass | About 60 (not highly resolved) | 260 |
| Washed microalgal biomass (insoluble fraction) | Not resolved | 260 |
| Acetylated washed microalgal biomass | 140 | 315 |

Example 4

Processing and Strength Properties of Acetylated Microalgal Biomass

Acetylated algae was first compounded with triethylcitrate (TEC), used as an external plasticizer, to form homogeneous and thermoplastic material. In addition, acetylated algae was blended with polylactic acid (PLA) and TEC. The compounding was performed at 190° C. prior to injection molding with a two screw compounder. For evaluation of mechanical properties, tensile test bars were prepared by injection molding at 180° C. The tensile strength properties were tested according to the ISO 527 standard.

TABLE 6

Tensile strength properties of algae based composite materials.

| | Blending proportions, % | | | Young's modulus, MPa | Tensile stress at max load, MPa | Tensile strain at max load, % |
|---|---|---|---|---|---|---|
| | Acetylated-Algae | TEC | PLA | | | |
| PLA ref | — | — | 100 | 2 600 | 85.6 | 3.9 |
| Acetylated algae | 83 | 17 | — | — | 0.2 | 0.2 |
| Acetylated algae + PLA | 33 | 17 | 50 | — | 6.5 | 132.7 |
| Acetylated 'washed' algae + PLA (small scale) | 23 | 17 | 60 | 830 | 18.8 | 3.3 |
| Acetylated 'washed' algae + PLA (large scale for Demo material) | 27 | 13 | 60 | 1 600 | 13.5 | 3.1 |

Acetylated algae was thermoplastic and easily moldable, forming a homogeneous and well dispersed material system with TEC (Table 6). Acetylated algae blends with PLA had better strength properties than acetylated algae alone.

Better strength properties were reached when acetylation was performed for washed algae without small molecular, easily soluble material. A lower TEC content of 13% was found to increase the modulus and strength. The Young's modulus, which is a measure of the stiffness of an elastic material, was highest in this case. The test bar could not be broken in tensile testing (interrupted when 60% axial strain was reached).

Example 5

Hydrothermalization of Microalgal Biomass

TABLE 7

Process conditions in the hydrothermal carbonization of the algae

| Experiment | Temp (° C.) | Time (min) | Consistency (g/100 ml) | Additive |
|---|---|---|---|---|
| SOL-101 | 180 | 60 | 20 | CA |
| SOL-102 | 180 | 60 | 20 | AA |
| SOL-103 | 180 | 180 | 20 | CA |
| SOL-104 | 180 | 180 | 20 | AA |
| SOL-105 | 180 | 180 | 10 | CA |
| SOL-106 | 180 | 180 | 10 | AA |
| SOL-107 | 200 | 60 | 20 | CA |
| SOL-108 | 200 | 60 | 20 | AA |
| SOL-109 | 200 | 180 | 20 | CA |
| SOL-110 | 200 | 180 | 20 | AA |
| SOL-111 | 200 | 180 | 10 | CA |
| SOL-112 | 200 | 180 | 10 | AA |
| SOL-113 | 300 | 180 | 20 | CA (½) |
| SOL-114 | 300 | 180 | 20 | — |
| SOL-115 | 220 | 180 | 20 | — |

(*CA = citric acid, AA = acrylic acid)

The experiments from SOL-101 to SOL-112 were performed in a rotating reactor with six separate sealable steel reactors of 500 ml in volume. Prior to heating, the dry algae feedstock was vigorously stirred in 100 ml of water and added in the reactor. The reactor was then heated to target temperature in which it was kept for the scheduled time. After the reaction, the sample was cooled and filtered and the aqueous phase was collected for further analyses. The solid carbonaceous fraction was washed with technical ethanol and water followed by drying at 105° C. for overnight.

The produced carbons were imaged with electron microscopy and the yield, adsorption properties and oxygen:carbon (O:C) ratio were determined. In addition, the nitrogen (N), phosphorous (P) and potassium (K) content of the aqueous phase was determined to calculate the recovery of these nutrients in the liquid phase. The overall results on the HTC carbonization are summarized in the table below.

content of these components, the carbon content of the alga feedstock was approximated to 45%. The yield of the carbon product was 16-33% on dry algae, and since HTC carbon has typically ca. 85% of carbon the carbon yield of the process was 30-60%.

The applicability of the carbon product as an adsorbent was determined by using methylene blue (MB) adsorption test. This is a well-established model substance to evaluate the adsorption capacity of activated carbons. The MB adsorption capacities of the produced carbons were up to 15 mg/g.

The presence of functional groups was determined using Fourier transform infrared (FTIR) spectroscopy for selected samples. The technique is especially sensitive to polar (e.g. C=O) bonds, and hence carbonyl and carboxylic acid functionalities can be readily detected. The FTIR spectra of

TABLE 8

Summary of the results from HTC carbonization.

| | Mass yield, % on algae[1] | Carbon yield, % on carbon in the feedstock[2] | MB adsorption, mg/g[3] | Recovery of elements in aqueous phase, % | | | O/C[4] |
|---|---|---|---|---|---|---|---|
| | | | | N | K | P | |
| SOL-101 | 18 | 33 | 7.7 | 17.6 | 87.5 | 86.1 | 0.09 |
| SOL-102 | 16 | 30 | 9.1 | — | — | — | 0.11 |
| SOL-103 | 31 | 57 | 15.3 | 29.7 | 92.2 | 90.2 | 0.14 |
| SOL-104 | 29 | 54 | 8.3 | 39.9 | 93.8 | 86.1 | 0.14 |
| SOL-105 | 22 | 41 | 6.1 | 41.9 | 90.6 | 82.0 | 0.16 |
| SOL-106 | 19 | 35 | 11.1 | — | — | — | 0.12 |
| SOL-107 | 27 | 50 | 4.8 | 37.2 | 95.3 | 90.2 | 0.14 |
| SOL-108 | 28 | 52 | 5.6 | — | — | — | 0.15 |
| SOL-109 | 33 | 61 | 9.9 | 31.8 | 98.4 | 90.2 | 0.12 |
| SOL-110 | 31 | 57 | 9.0 | — | — | — | 0.11 |
| SOL-111 | 29 | 54 | 10.1 | — | — | — | 0.09 |
| SOL-112 | 27 | 50 | 8.2 | — | — | — | 0.11 |
| SOL-113 | 21 | 39 | 0.1 | — | — | — | 0.04 |
| SOL-114 | 19 | 35 | 1.7 | — | — | — | 0.02 |
| SOL-115 | 30 | 55 | 7.1 | — | — | — | 0.04 |

Figure 2:
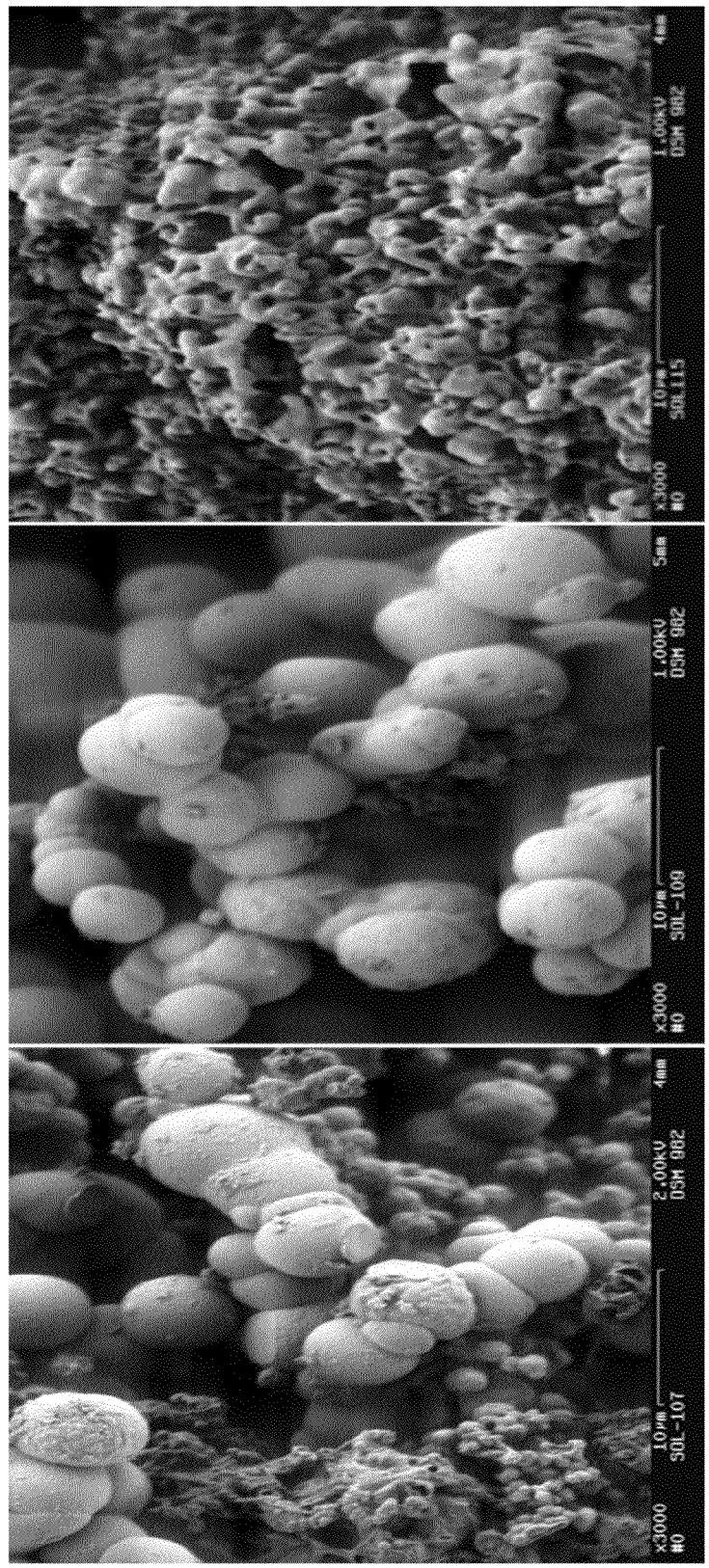
FIG. 2 shows scanning electron microscopy (SEM) morphology of selected hydrothermal treated microalgal samples made with an embodiment of the compositions as illustrated in Example 5.

[1]The maximum theoretical yield was ca. 65 w % on microalgae feedstock.
[2]The content of carbon was approximated to 46% and 85% in the feedstock and carbon product, respectively.
[3]The reference value for commercial activated carbon was 135 mg/g.
[4]Mass ratio based on EDS measurements The hydrothermal treatment of algae resulted in the formation of granular carbonised material and its color varied from brown to black. High carbonization resulted in darker product, indicating a more complete carbonization which was also supported by the O:C analysis (above table). Scanning electron microscopy (SEM) images of the carbons were obtained. In most samples, spherical particles of a few micrometers in diameter were formed. FIG. 2 presents SEM images of carbon samples SOL-107 (left), SOL-109 (middle) and SOL-115 (right). The scale bar in all images is 10 μm.

In addition to spherical particles, the carbonized algae contained also other types of morphological regions and certain samples did not contain any spherical particles (sample SOL-115).

Figure 3:
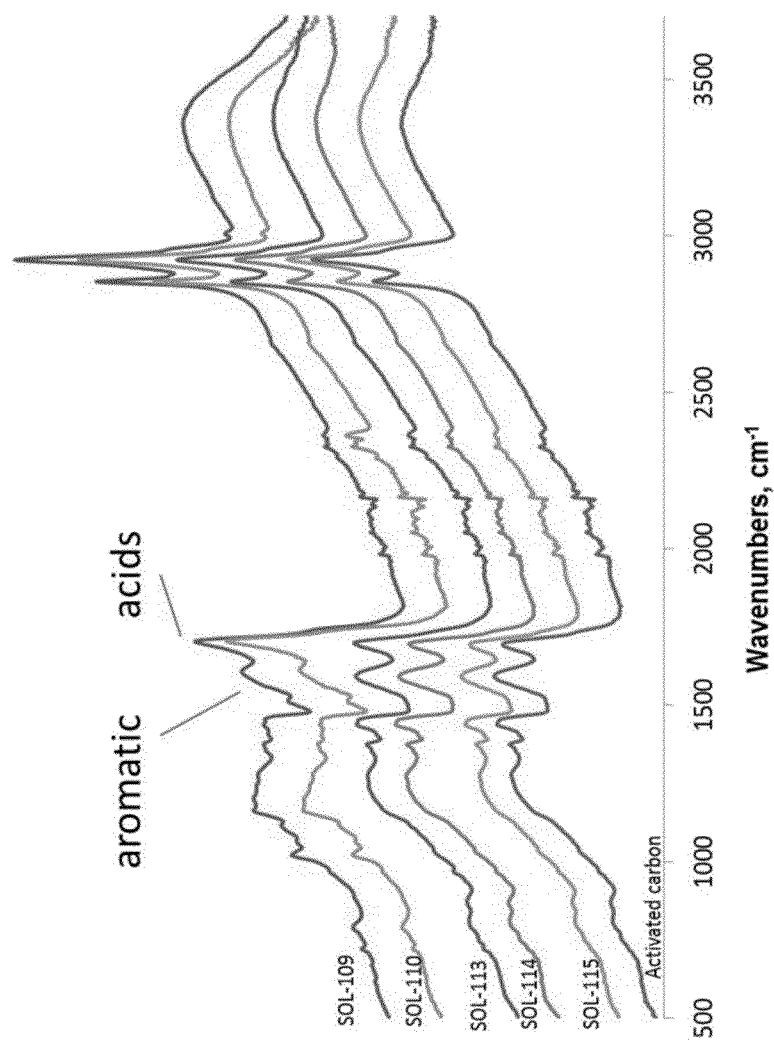
FIG. 3 shows Fourier transform infrared (FTIR) spectra of selected carbon samples made with an embodiment of the compositions as illustrated in Example 5.

During carbonization, the carbon in the feedstock is retained in the solid phase while oxygen content is dramatically reduced. The algae feedstock consisted of carbohydrates (~60%), proteins (6-9%), residual oil (8-12%) and inorganics (6%), and based on general knowledge of carbon selected HTC carbons in the figure below illustrate that the samples carbonized at elevated temperatures with or without the acid catalyst (SOL-113, SOL-114 and SOL-115) were similar to conventional activated carbon. Interestingly, the samples carbonized at 200° C. with the presence of acid catalyst, either citric or acrylic acid, possessed remarkably higher number of carboxylic acid groups compared to other samples or the commercial activated carbon. Acrylic acid produced even higher amount of these groups than citric acid. The presence of carboxylic acid groups enlarges the applicability of these carbon particles in novel applications, such as metal adsorbent. It is believed that these functionalities enhance the water dispersibility of the particles, and they are capable of adsorbing certain metal ions, such as Pd, Cd, Hg, or Pb. FIG. 3 shows FTIR spectra of selected carbon samples compared to commercial activated carbon. The spectra were offset for illustrative purposes.

The algae feedstock contains some nitrogen (N), phosphorous (P) and potassium (K) which are vital elements in fertilizers. The recovery of these elements from the aqueous phase could further improve the economy of the HTC process. The elemental analysis of the filtrates illustrated that phosphorous and potassium of algae were almost entirely enriched in the aqueous phase whereas significant amount of nitrogen remained in the solid (or gas) phase. The nearly quantitative detection of phosphorous and potassium in the aqueous phase make their recovery attractive.

Example 6

Production of Paper Using Microalgal Biomass

Replacement of pulp with less expensive algae in paper applications was tested and effects on some basic paper technical properties (strength, brightness, bulk, absorption) were evaluated. In aqueous conditions of papermaking the partial solubility of the algae can be a critical factor affecting the applicability of algae. Therefore, the technical potential of using the water insoluble and water soluble polymeric fractions produced as described above was also investigated. Results obtained are shown in the table below.

In the first trials, 5% of algae as such was used in thin handsheets of 30 g/m2 prepared from bleached eucalyptus Kraft pulp to simulate the tissue paper as a potential final product. With relatively low 5% replacement of pulp with algae, no significant effect on paper technical properties was detected. Some reduction in brightness and water absorption (based on capillary rise) was observed, but the strength properties remained at the same level. No retention aids ("RA") were used in this case.

To better evaluate the effect of algae on strength properties, a higher algae charge of 20% was tested using 60 g/m$^2$ handsheets. In this case, a 0.02% PAM based retention aid (Percol, BASF) was added. Also the effect of water insoluble and soluble polymeric algae components on paper technical properties was evaluated.

Besides the reduced brightness and absorption (as capillary rise), no deterioration of paper technical properties were detected with 20% replacement of eucalyptus pulp with algae. Actually, slight improvement of wet strength was observed. The improvement was consistent in all the studied fractions. For tissue paper this would be an important property. Brightness of the paper was not reduced when the soluble fraction was used.

Example 7

Anionization of Microbial Biomass

Anionisation was performed on *Prototheca moriformis* biomass from which the majority of triglyceride had been extracted. Anions were introduced by carboxymethylation (CM) of microalgal biomass at high consistency (up to 92%). After anionisation the reaction product was washed in ethanol/water, and the degree of substitution (DS) and the charge density was determined.

Anionization of starch and cellulose is usually carried out up to a DS of 1. In this work, the target DS was set to lower and higher level than 1 (DS<1, DS>1) assuming ~60% polysaccharide content in the algae feedstock. The anionic groups introduced by carboxymethylation into the algae polysaccharides were determined by a potentiometric titration according to Hong et al, Zellst. Pap (1978). The 'DS' values given for CM-algae are based on the assumption that the polysaccharide content of algae would be 100%. This is not the case, and the DS values reported are rather to indicate the differences in the modification levels of distinct samples than true DS of polysaccharides.

TABLE 9

Effect of algae on paper technical properties of bleached eucalyptus Kraft pulp.

| | Euca Ref | 5% Algae | Euca Ref | Euca Ref + RA | 20% algae + RA | 20% soluble polymeric fr. + RA | 20% Insoluble fraction + RA |
|---|---|---|---|---|---|---|---|
| Grammage, g/m$^2$ | 33.1 | 32.3 | 63.3 | 63 | 63.8 | 63.4 | 62.9 |
| Bulking thickness, μm | 52.9 | 51.1 | 93.2 | 94.0 | 92.6 | 94.0 | 88.9 |
| Apparent bulk-density, kg/m$^3$ | 625 | 633 | 680 | 670 | 689 | 674 | 708 |
| Bulk, cm$^3$/g | 1.60 | 1.58 | 1.47 | 1.49 | 1.45 | 1.48 | 1.41 |
| ISO-brightness, % | 86.3 | 80.9 | 87.3 | 86.5 | 69.0 | 87.1 | 68.7 |
| Tensile strength, kN/m | 1.63 | 1.69 | 3.5 | 3.55 | 3.61 | 3.47 | 3.6 |
| Tensile index, Nm/g | 49.4 | 52.2 | 55.3 | 56.3 | 56.6 | 54.7 | 57.2 |
| Stretch, % | 2.7 | 2.9 | 3.2 | 3.2 | 3.3 | 3.1 | 3.5 |
| Tensile energy absorption, J/m$^2$ | 31.5 | 34.8 | 81.2 | 82.0 | 86.8 | 78.7 | 89.9 |
| TEA index, J/g | 0.953 | 1.08 | 1.28 | 1.3 | 1.36 | 1.24 | 1.43 |
| Tensile stiffness, kN/m | 198 | 195 | 409 | 401 | 400 | 407 | 383 |
| Tensile stiffness index, kNm/g | 5.99 | 6.04 | 6.46 | 6.37 | 6.27 | 6.42 | 6.09 |
| Modulus of elasticity, N/mm$^2$ (of bulking thickn.) | 3743 | 3824 | 4389 | 4269 | 4321 | 4332 | 4309 |
| Tensile strength after immersion in water, kN/m | 0.055 | 0.057 | 0.117 | 0.120 | 0.142 | 0.128 | 0.134 |
| Water absorption as capillary rise - Klemm method, mm | 61 | 31 | 48 | 41 | 23 | 29 | 22 |

Ref = 30 and 60 g/m$^2$ handsheets from refined Eucalyptus kraft pulp, RA = 0.02% PAM based retention aid (Percol).

TABLE 10

Information on performed anionisations and the reached degree of substitution (DS.)

| Starting | Route 1 | | Route 2 | | Route 3 | |
| --- | --- | --- | --- | --- | --- | --- |
| | | | Cross-linked | Cross-linked | 'Washed | 'Washed |
| Material | Algae | Algae | algae 5% | algae 10% | algae' | algae' |
| Target DS | <1 | >1 | <1 | <1 | <1 | >1 |
| Reached DS* | 0.5 | 1.3 | n.d. | n.d. | 0.5 | 0.8 |
| Charge density, | −2.8 | −5.7 | −1.0 | −0.4 | −2.8 | −3.9 |
| Code | CM algae DS 0.5 | CM– algae DS 1.3 | 5% Gly, CM DS 0.6 | 10% Gly, CM DS 0.6 | Anionised 'washed' | Anionised 'washed' | n.d. = not determined.

The CM modification was successful as shown by the charge density levels obtained. Comparison of the original microalgae and the 'washed' high molecular weight insoluble fraction show that the anionic charge of the algae originates largely from the small molecular easily soluble material. For 'washed algae' the same degree of anionisation was reached (at lower target DS level), but the anionic charge is probably distributed more efficiently also into the insoluble high molecular weight polymers. The anionisation to higher DS level was less efficient when the 'washed' algae was used.

Figure 4:
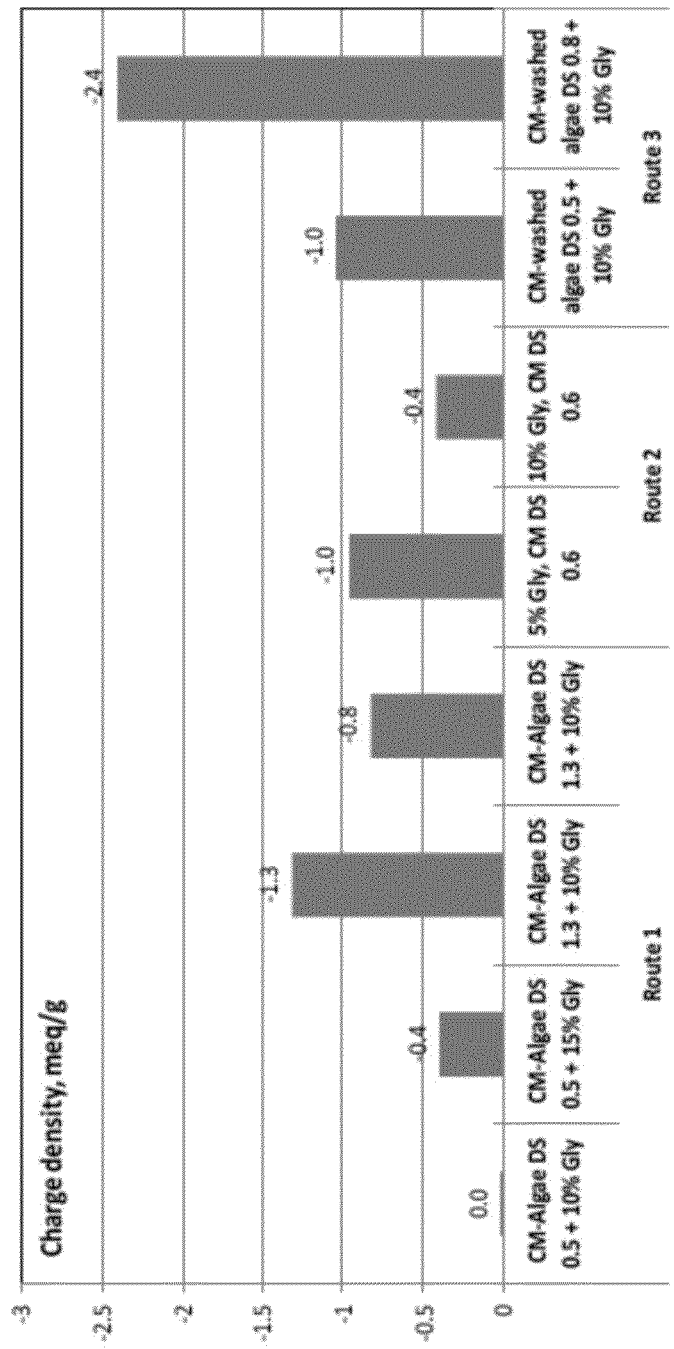
FIG. 4 shows a graph of charge densities of the crosslinked, anionized biomass made with an embodiment of the compositions as illustrated in Example 7.
Figure 5A:
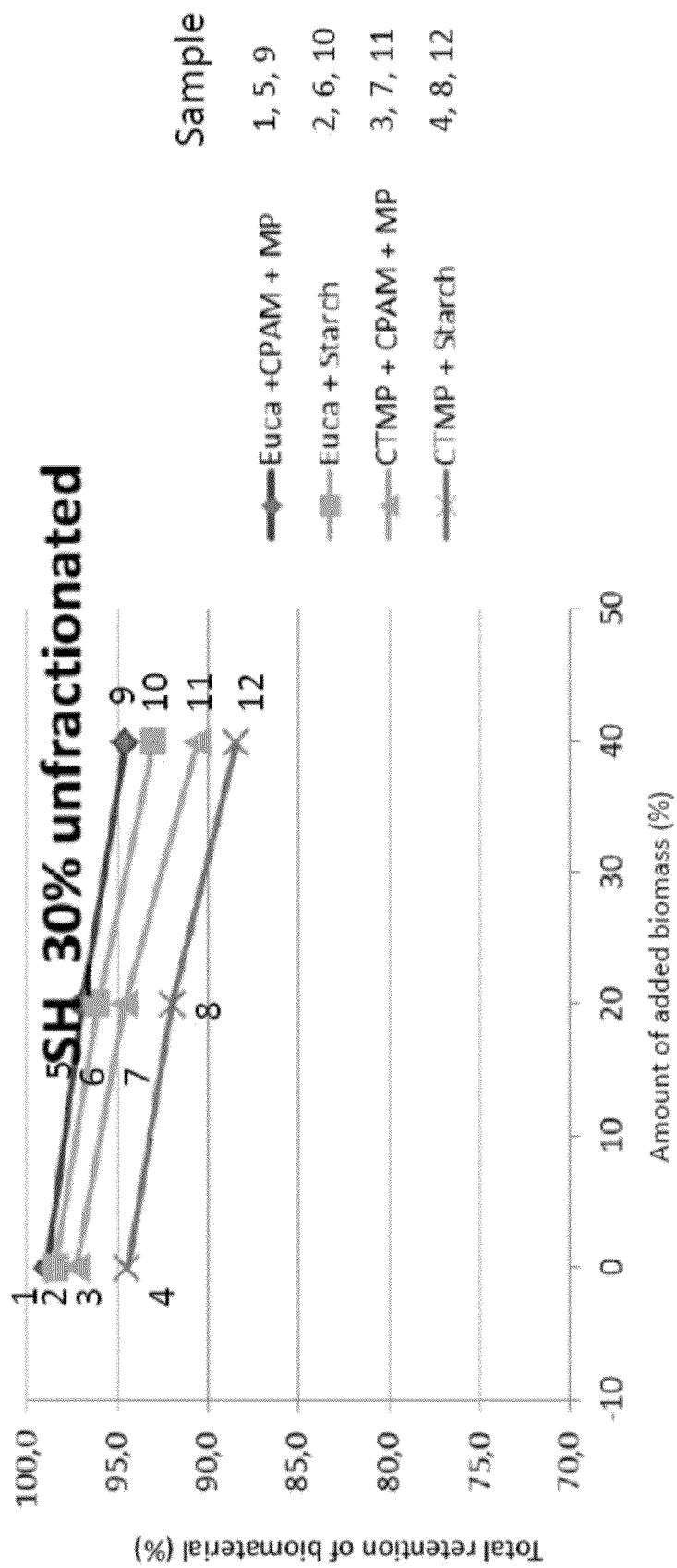
FIG. 5A-B show the retention results of filtration studies conducted on paper preparations made with biomass in an embodiment of the compositions as illustrated in Example 12.
Figure 5B:
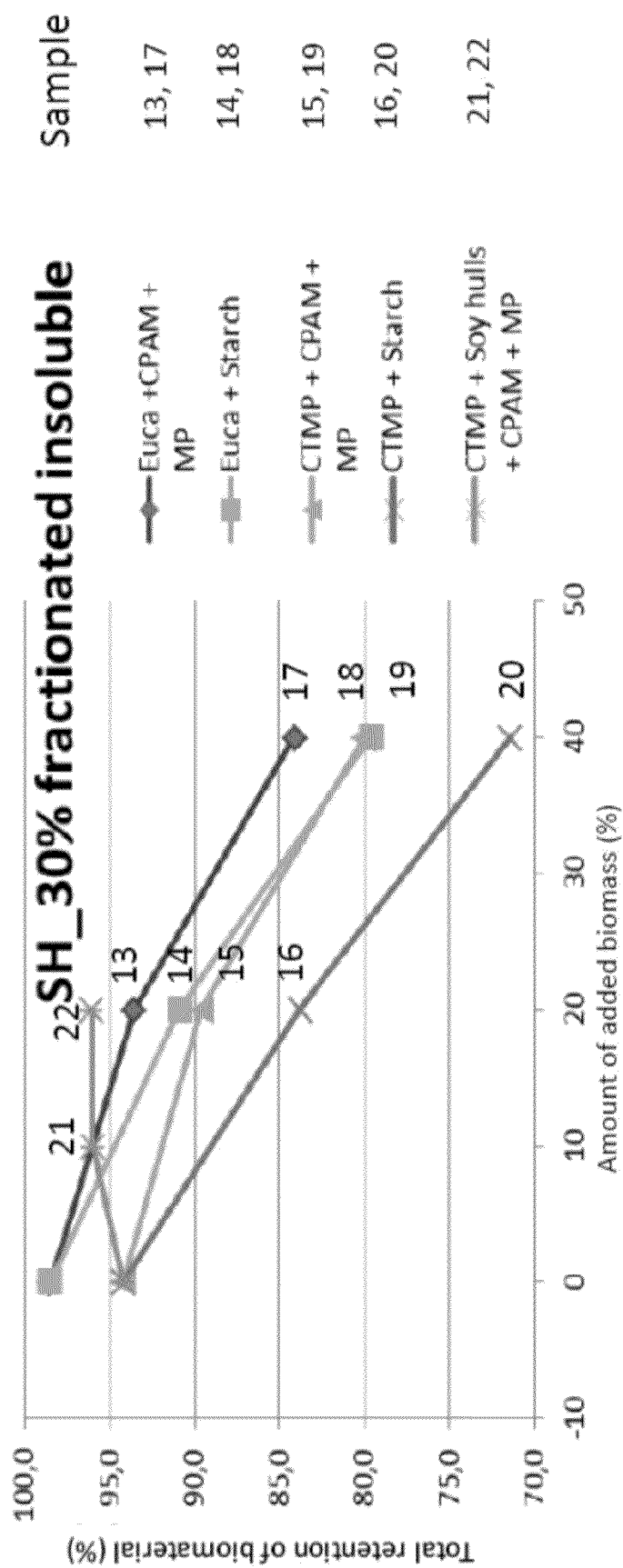

The charge density of the material after both anionisation and crosslinking stages is shown in FIG. 4. Charge density of the final products was recorded in meq/g. Measured using a Mutek titration with poly-DADMAC.

The water absorption capacity of the obtained materials was measured as weight gain by soaking the material in water and weighting the wet material before and after drying. The absorbance was calculated as ((wet weight−dry weight)/dry weight)×100%. When crosslinking was followed by anionization for washed or unwashed microalgae, a water absorption of about 1400% was obtained, with absorption occurring over about 4 hours. Too high a level of crosslinking level reduced water absorption in all cases.

Example 8

Use of Triglyceride Containing Biomass

Heterotrophically cultivated microalgae, where less than 50% of the triglyceride has been removed, is extruded using 10-50% glycerin as a plasticizer and optionally a surfactant, e.g., Excel P40S. An extruder, for example, a Thermo Prism™ USLAB 16 twin screw extruder (Thermo Electron Corporation, Stone, England) is used to complete the processing. The Thermo Prism™ USLAB 16 twin screw extruder has eleven zones: zone 0 is a feeding zone where the materials from a feeder (e.g., feeders available from K-Tron North America, Pitman, N.J.) are accepted and conveyed to the zone 1, 2, etc., until zone 9. The zones are kneading sections of the twin screws, and zone 10 is a die located at the end of the extruder. Along zones 1 thorough 9, the temperature is systematically increased. In one temperature setup, the temperature setup is 80, 90, 115, 125, 125, 125, 122, 120 and 115° C. from zones 1 to 9. The die temperature is 110° C. The screw rotational speed is 150 rpm. The biomass, after being mixed with 2% Excel P-40S, is fed at 1.6 lb/hr. Glycerin is pumped into zone 1 using a gear pump (Bodine Electric Company, Grand Island, N.Y.). When a strand is formed, it is cooled down through a conveyer belt (Bondie Electric Company, Chicago, Ill.).

Example 9

Combination of Biomass with Plant Polymers

In this example, native corn starch is co-processed with *Prototheca moriformis* or *Chlorella protothecoides*. Thermoplastic processing conditions are performed using a Thermo Prism™ USLAB 16 twin screw extruder (Thermo Electron Corporation, Stone, England). One K-Tron feeder (K-Tron North America, Pitman, N.J.) is used to feed a mixture of biomass, corn starch and surfactant (ratios ranging from 69/29/2 to 29/69/2) into the extruder zone 0, and glycerin is pumped into zone 1 at 28% of the mixture using the gear pump (Bodine Electric Company, Grand Island, N.Y.). Strands from the die are cut to form pellets and stored in plastic bags.

A mixture of the pellets above and 90% PP SV954 is dry blended with 5% trans pearl lavender for making injection molded articles. The processing temperature profile for heating bands 1 to 3 is 145° C., 148° C., and 150° C. respectively. The nozzle temperature is 153° C., and the mold temperature is set at 80° F. The injection molding cycle begins when the mold is closed. At this point, the screw moves forward and injects the mixture of resins through the nozzle and into the sprue. The material fills the mold (runners, gates and cavities). During the packing phase, additional material is packed into the cavities while a holding temperature is maintained to compensate for material shrinkage. The material is cooled and solidified in the mold while the screw rotates counterclockwise backward, melting the plastic for the next shot. The mold opens and the parts are ejected with a cycle time of 40 seconds. The next cycle begins when the mold closes again.

Example 10

Anionization of Microbial Biomass

A blend of conventional papermaking fibers and microalgal biomass is prepared. Eucalyptus hardwood fibers commercially available from Fibria, Sao Paulo, Brazil are used. A single ply, three-layered, uncreped through-dried tissue basesheet is made generally in accordance with U.S. Pat. No. 5,607,551 to Farrington.

65 pounds (oven dry basis) of eucalyptus hardwood kraft fiber is dispersed in a pulper for 25 minutes at a consistency of 3 percent before being transferred in equal parts to two machine chests and diluted to a consistency of 1 percent. Microalgal biomass is added as a dry powder over a period of 5 minutes to avoid clumping and allowed to disperse for 5 additional minutes in the machine chest before adding starch.

Redibond 2038A, available as a 30 percent actives aqueous solution from National Starch and Chemical is used. The appropriate amount of starch to add is determined from the amount of Eucalyptus in each machine chest. The appropriate amount of starch is weighed out and diluted to a 1 percent actives solution with water before being added to the machine chest. The starch is added after the microalgal biomass. The fiber slurry is allowed to mix for 5 minutes before the stock solution is sent to the headbox.

40 pounds (oven dry basis) of northern softwood kraft fiber is dispersed in a pulper for 25 minutes at a consistency of 3 percent before being transferred to a second machine chest and diluted to 1 percent consistency. The softwood fibers may be refined after pulping and before transfer to the machine chest.

Prior to forming, each stock is further diluted to approximately 0.1 percent consistency and transferred to a 3-layer headbox in such a manner as to provide a layered sheet comprising 65 percent Eucalyptus and 35 percent NSWK, where the outer layers comprise the Eucalyptus/microalgal biomass blend and the inner layer comprises the NSWK fibers. A solution of a medium molecular weight cationic retention aid, Praestol 120L, available from Ashland Chemical is prepared by adding 80 grams of Praestol 120L to 80 liters of water under high shear agitation. The dilute solution is added in-line at the outlet side of the fan pump of each Eucalyptus pulp stream as the dilute pulp suspension travels to the head box at a rate of from about 0.035 to 0.040 percent by weight of fiber.

The formed web is non-compressively dewatered and rush-transferred to a transfer fabric traveling at a speed about 25 percent slower than the forming fabric. The web is then transferred to a through drying fabric, dried and calendered. Basis weights of the inner and outer layers are determined individually to ensure a 32.5/35/32.5 layer split is maintained.

Example 11

Thermoplastic Composition Prepared with Oleaginous Microalgal Biomass and Soy Hulls This example describes the use of covalently modified microalgal biomass to produce a thermoplastic composition with improved elongation properties. *Prototheca moriformis* (UTEX 1435), cultured under heterotrophic conditions such as those described in WO2008/151149, WO2010/063032, and WO2011/150411 was dried then mechanically pressed to extract oil with 30% soybean hulls added by dry weight as a press aid. The resulting microalgal biomass with soybean hull plant polymers retained 9% residual oil. This biomass was milled then acetylated as in Example 2 and as described in U.S. Pat. No. 3,795,670. The DS of acetylation was 2.5. Aceytylated microalgal biomass with soybean hull polymers, triethyl citrate (TEC), and PLA were dry mixed at the weight percentages shown in Table 11. Following dry mixing, compounding and extrusion of the blends were performed with a Brabender Plastic-Corder PL 2100-6 melt mixer. Thermoplastic granules were prepared with a knife mill grinder. For evaluation of mechanical properties, tensile test bars were prepared by injection molding. Tensile strength properties were tested according to the ISO 527 standard. Data from these tests are shown in Table 11.

TABLE 11

Tensile strength properties of microalgae based thermoplastic materials

| Sample | Microalgal biomass with soybean hull polymers (weight %) | TEC (weight %) | PLA grade | PLA (weight %) | Max strength MPa | Max elong. % |
|---|---|---|---|---|---|---|
| 1 | 55 | 5 | 3051D | 40 | 2.8 | 150 |
| 2 | 33 | 7 | 3051D | 60 | 6 | 180 |
| 3 | 43 | 7 | 3051D | 50 | 10 | 55 |
| 4 | 37 | 13 | 2002D | 50 | 5 | 65 |
| 5 | 27 | 13 | 2002D | 60 | 5.5 | 200 |
| 6 | 27 | 13 | 3051D | 60 | 6 | 220 |
| 7 | 37 | 13 | 3051D | 50 | 4.5 | 60 |
| 8 | 0 | 0 | 3051D | 100 | 85.6 | 3.9 |

Acetylated microalgal biomass with soybean hull polymers was thermoplastic and easily pressable. Thermoplastic compositions were prepared with as great as 55% biomass content. As shown in Table 11, PLA blends made with acetylated biomass showed improved elongation properties. The elongation of the sample in response to a tensile load was increased from 3.9% for a pure PLA to as high as 220% in samples comprising acetylated microalgal biomass (see Sample 8 vs 6).

Example 12

Retention of Microalgal Biomass in Paper Preparations

Various blends of papermaking fibers, retention aids, microalgal biomass prepared by mechanical pressing of *Prototheca moriformis* (UTEX 1435) with soybean hull bulking agents, and soybean hull polymers were combined and processed in a paper application as described in Example 6. Total retention of biomaterial was tested for three types of inputs: 1) Soybean hull polymers alone, 2) the biomass described in Example 11 that was unfractionated microalgal biomass prepared with 30% soybean hulls added by dry weight, and 3) the insoluble fraction remaining after solvent based fractionation of microalgal biomass prepared with 30% soybean hulls added by dry weight. In the case of the latter biomass, the insoluble fraction was prepared according to the processing steps described in Example 1. 10%, 20%, or 40% of the indicated pulp was substituted with the indicated microalgal biomass or soybean hull polymers.

The weight percentage of input material combined with the various papermaking fibers and retention aids for each sample is shown in Table 12. The total retention of biomaterial, indicated in percent, was evaluated by filtration studies. These results are presented in FIG. 4, wherein individual data points are identified with a sample number that corresponds to the listing in Table 12. The retention values of the various pulps and retention aids prepared without microalgal biomass or soybean hull polymers are also shown in FIG. 4. CPAM refers to cationic polyacrylamide polymer retention aid. MP refers to modified polyamine retention aid.

TABLE 12

Samples evaluated in filtration studies of paper preparations.

| Paper Fiber | Retention Aid | No added microalgal biomass, no added soybean hull polymer | Soybean hull polymers | | Microalgal biomass with 30% by dry weight soybean hull polymers | | | |
|---|---|---|---|---|---|---|---|---|
| | | | | | Unfractionated | | Insoluble Fraction | |
| | | | 10% | 20% | 20% | 40% | 20% | 40% |
| Eucalyptus kraft pulp | CPAM + MP | Sample 1 | | | Sample 5 | Sample 9 | Sample 13 | Sample 17 |
| Eucalyptus kraft pulp | starch | Sample 2 | | | Sample 6 | Sample 10 | Sample 14 | Sample 18 |
| Chemithermomechanical pulp | CPAM + MP | Sample 3 | Sample 21 | Sample 22 | Sample 7 | Sample 11 | Sample 15 | Sample 19 |
| Chemithermomechanical pulp | starch | Sample 4 | | | Sample 8 | Sample 12 | Sample 16 | Sample 20 |

As shown in FIG. 4, the total retention of biomaterial for the paper applications prepared without microalgal biomass and without soybean hull polymer was between about 94% and about 99% according to the specific combinations of pulp and retention aids. The samples prepared with 20% unfractionated microalgal biomass containing soybean hull polymers were characterized by retention values of about 91% to about 97%, while samples prepared with 40% unfractionated microalgal biomass containing soybean hull polymers were characterized by retention values of about 87% to about 94%. Samples prepared with the insoluble fraction of microalgal biomass containing soybean hull polymers were characterized by slightly reduced retention values of from about 84% to about 94% at 20% incorporation and from about 71% to about 84% at 40% incorporation. CPAM provided better retention than starch, and retention on eucalyptus kraft pulp was better than on CTMP. Samples 21 and 22, prepared with chemithermomechanical pulp, CPAM, MP, and soybean hulls showed high retention values of about 96% at both 10% and 20% incorporation.

Example 13

Thermoplastic Compositions Prepared with Oleaginous Microalgal Biomass and Different Polymers This example describes the use of microalgal biomass to produce thermoplastic blends with different thermoplastic polymers. *Prototheca moriformis* (UTEX 1435) was cultured under heterotrophic conditions such as those described in WO2008/151149, WO2010/063032, and WO2011/150411, dried, then mechanically pressed or exposed to hexane solvent to extract oil. Four different microalgal biomass preparations (A-D), listed in Table 13, were obtained through alterations in processing and extraction conditions. Where noted, 15% soybean hulls added by dry weight were used a press aid. Microalgal biomass preparation D was the insoluble fraction obtained from wet fractionation of preparation B as described in Example 1.

TABLE 13

Microalgal Biomass Preparations used in compounding thermoplastic compositions

| Microalgal Biomass Preparation | Oil Content | Extraction Method | Soy Hull % addition | Fractionation |
|---|---|---|---|---|
| A | <2% | hexane | 0 | unfractionated |
| B | 7.2% | mechanical | 15 | unfractionated |
| C | <2% | mechanical, hexane | 15 | unfractionated |
| D | <5% | mechanical | 15 | insoluble |

Microalgal biomass preparations A-D were dry mixed with indicated polylactic acid, linear low density polyethylene, or high density polyethylene polymers at the weight percentages shown in Table 14. Following dry mixing, compounding and extrusion of the blends were performed with a 26 mm co-rotating twin screw extruder. Thermoplastic granules were prepared with a knife mill grinder. For evaluation of mechanical and thermal properties, test bars were prepared by injection molding. Room temperature tensile properties were tested according to the ISO 527 and ASTM D638 standards. Compositions 13-1 through 13-8 and 13-17 through 13-24 were all tested at a standard speed of 0.20 inches per minute. Compositions 13-9 through 13-16 were tested with a speed of 2.0 inches per minute. Elongation was measured with an extensometer. Izod impact testing was performed according to ISO 180 and ASTM D256 (notched izod) and ASTM D4812 (unnotched izod) at room temperature. Pendulum weight used is given in pounds (lbs). Room temperature flexural testing was performed according to ASTM D790 and ISO 178 standards. Specific gravity of thermoplastic compositions was measured according to ASTM D792, ASTM D4883, ASTM D1505, and ISO 1183. Differential scanning calorimetry was performed on the thermoplastic compositions to discern glass transition (Tg) and melting temperatures (Tm). Standard deviations, abbreviated 'SD' are indicated where evaluated. Color analysis of thermoplastic compositions and of microalgal biomass preparations were made with spectrophotometer using a LAB three dimensional color scale. Data from these tests are shown in Tables 15, 16, 17, 18, 19, and 20.

TABLE 14

Thermoplastic compositions comprising microalgae and different polymers

| Thermoplastic Composition | Micro algal Biomass Preparation | Microalgal Biomass % weight | Polymer | Grade/ Source | Polymer % weight |
|---|---|---|---|---|---|
| 13-1 | A | 20 | PLA | 2003D/ NatureWorks | 80 |
| 13-2 | B | 20 | | | 80 |
| 13-3 | C | 20 | | | 80 |
| 13-4 | D | 20 | | | 80 |
| 13-5 | A | 40 | | | 60 |
| 13-6 | B | 40 | | | 60 |
| 13-7 | C | 40 | | | 60 |
| 13-8 | D | 40 | | | 60 |
| 13-9 | A | 20 | LLDPE | 1001.59/ Exxon Chemical | 80 |
| 13-10 | B | 20 | | | 80 |
| 13-11 | C | 20 | | | 80 |
| 13-12 | D | 20 | | | 80 |
| 13-13 | A | 40 | | | 60 |
| 13-14 | B | 40 | | | 60 |
| 13-15 | C | 40 | | | 60 |
| 13-16 | D | 40 | | | 60 |
| 13-17 | A | 20 | HDPE | 6007/ Chevron Phillips Chemical | 80 |
| 13-18 | B | 20 | | | 80 |
| 13-19 | C | 20 | | | 80 |
| 13-20 | D | 20 | | | 80 |
| 13-21 | A | 40 | | | 60 |
| 13-22 | B | 40 | | | 60 |
| 13-23 | C | 40 | | | 60 |
| 13-24 | D | 40 | | | 60 |

TABLE 15

Flexural strength and flexural modulus of thermoplastic compositions comprising microalgae and different polymers

| Thermoplastic Composition | Flexural Strength (psi) | Standard Deviation | Flexural Modulus (psi) | Standard Deviation |
|---|---|---|---|---|
| 13-1 | 10800 | 200 | 500000 | 4970 |
| 13-2 | 9570 | 131 | 497000 | 3700 |
| 13-3 | 11300 | 206 | 536000 | 15500 |
| 13-4 | 10300 | 118 | 513000 | 11100 |
| 13-5 | 7180 | 134 | 494000 | 9440 |
| 13-6 | 6490 | 178 | 498000 | 7980 |
| 13-7 | 7830 | 163 | 639000 | 5380 |
| 13-8 | 7750 | 62 | 567000 | 4500 |
| 13-9 | 1600 | 21 | 51500 | 1280 |
| 13-10 | 1410 | 9 | 42300 | 1530 |
| 13-11 | 1500 | 21 | 46200 | 1340 |
| 13-12 | 1470 | 14 | 44600 | 1490 |
| 13-13 | 1620 | 21 | 86000 | 2080 |
| 13-14 | 1370 | 9 | 53200 | 2270 |
| 13-15 | 1550 | 21 | 71100 | 3450 |
| 13-16 | 1420 | 19 | 60100 | 3340 |
| 13-17 | 4640 | 46 | 204000 | 2260 |
| 13-18 | 4300 | 114 | 191000 | 7100 |
| 13-19 | 4730 | 23 | 214000 | 5490 |
| 13-20 | 4350 | 88 | 189000 | 5870 |
| 13-21 | 3930 | 26 | 273000 | 6210 |
| 13-22 | 3640 | 33 | 220000 | 2520 |
| 13-23 | 4210 | 29 | 270000 | 1960 |
| 13-24 | 4060 | 80 | 242000 | 4910 |

TABLE 16

Tensile strength, elongation, and tensile modulus of thermoplastic compositions comprising microalgae and different polymers

| Thermoplastic Composition | Tensile Strength (psi) | Standard Deviation | Elongation (%) | Standard Deviation | Tensile Modulus (psi) | Standard Deviation |
|---|---|---|---|---|---|---|
| 13-1 | 5120 | 107 | 1.43 | 0.07 | 545000 | 10000 |
| 13-2 | 4310 | 111 | 1.27 | 0.03 | 577000 | 27400 |
| 13-3 | 5360 | 122 | 1.63 | 0.11 | 580000 | 14300 |
| 13-4 | 4640 | 74 | 1.51 | 0.05 | 548000 | 12900 |
| 13-5 | 3020 | 61 | 1.07 | 0.05 | 601000 | 20100 |
| 13-6 | 2540 | 40 | 1.25 | 0.07 | 561000 | 39000 |
| 13-7 | 3620 | 441 | 1.14 | 0.15 | 677000 | 40000 |
| 13-8 | 3390 | 44 | 1.18 | 0.04 | 627000 | 18100 |
| 13-9 | 1290 | 5 | 55.78 | 7.72 | 59000 | 5450 |
| 13-10 | 1230 | 8 | 65.25 | 2.42 | 48900 | 6520 |
| 13-11 | 1260 | 13 | 56.92 | 8.46 | 59100 | 13300 |
| 13-12 | 1270 | 11 | 40.62 | 7.23 | 59000 | 7030 |
| 13-13 | 974 | 42 | 34.73 | 11.33 | 100000 | 17100 |
| 13-14 | 989 | 14 | 39.17 | 5.95 | 53300 | 14000 |
| 13-15 | 1010 | 14 | 35.8 | 5.1 | 74000 | 168000 |
| 13-16 | 987 | 10 | 33.12 | 3.54 | 69200 | 3720 |
| 13-17 | 2800 | 20 | 10.93 | 0.94 | 236000 | 7260 |
| 13-18 | 2650 | 15 | 12.22 | 0.86 | 194000 | 2080 |
| 13-19 | 2790 | 34 | 10.12 | 1.54 | 217000 | 8360 |
| 13-20 | 2750 | 11 | 11.12 | 0.13 | 221000 | 4810 |
| 13-21 | 2040 | 10 | 9.5 | 1.32 | 294000 | 6140 |
| 13-22 | 2080 | 15 | 12.07 | 0.86 | 229000 | 7680 |
| 13-23 | 2170 | 13 | 9.53 | 0.27 | 295000 | 16900 |
| 13-24 | 2100 | 13 | 10.36 | 1.45 | 253000 | 12800 |

TABLE 17

Notched izod impact measurements of thermoplastic compositions comprising microalgae and different polymers

| Thermoplastic Composition | complete break | | | hinged break | | | partial break | | | non-break | | |
|---|---|---|---|---|---|---|---|---|---|---|---|---|
| | ft-lb)/in | SD | weight | ft-lb)/in | SD | weight | ft-lb)/in | SD | weight | ft-lb)/in | SD | weight |
| 13-1 | 0.55 | 0.03 | 5 | | | | | | | | | |
| 13-2 | 0.44 | 0 | 5 | | | | | | | | | |
| 13-3 | 0.45 | 0.02 | 5 | | | | | | | | | |
| 13-4 | 0.5 | 0.3 | 5 | | | | | | | | | |
| 13-5 | 0.53 | 0.04 | 5 | | | | | | | | | |
| 13-6 | 0.53 | 0.02 | 5 | | | | | | | | | |
| 13-7 | 0.5 | 0.06 | 5 | | | | | | | | | |
| 13-8 | 0.51 | 0.04 | 5 | | | | | | | | | |
| 13-9 | | | | | | | | | | 7.48 | 0.28 | 30 |
| 13-10 | | | | | | | 5.66 | 0.49 | 30 | 5.72 | n.a. | 30 |
| 13-11 | | | | | | | 5.94 | 0.47 | 30 | | | |
| 13-12 | | | | 4.68 | n.a. | 10 | 6.01 | 0.28 | 10 | | | |
| 13-13 | | | | | | | 5.41 | 0.2 | 30 | | | |
| 13-14 | | | | | | | 4.34 | 0.33 | 30 | | | |
| 13-15 | | | | | | | 4.56 | 0.19 | 30 | | | |
| 13-16 | | | | 3.93 | 0.45 | 10 | | | | | | |
| 13-17 | | | | 1.52 | 0.04 | 5 | | | | | | |
| 13-18 | | | | 1.91 | 0.06 | 5 | | | | | | |
| 13-19 | | | | 1.6 | 0.06 | 5 | | | | | | |
| 13-20 | | | | 1.82 | 0.06 | 10 | | | | | | |
| 13-21 | | | | 1.09 | 0.03 | 5 | | | | | | |
| 13-22 | | | | 1.39 | 0.09 | 5 | | | | | | |
| 13-23 | | | | 1.09 | 0.06 | 5 | | | | | | |
| 13-24 | | | | 1.28 | 0.08 | 10 | | | | | | |

TABLE 18

Un-Notched Izod impact measurements of thermoplastic compositions comprising microalgae and different polymers

| Thermoplastic Composition | complete break | | | hinged break | | | partial break | | | non-break | | |
|---|---|---|---|---|---|---|---|---|---|---|---|---|
| | (ft-lb)/in | SD | weight | (ft-lb)/in | SD | weight | (ft-lb)/in | SD | weight | (ft-lb)/in | SD | weight |
| 13-1 | 2.97 | 0.50 | 10 | | | | | | | | | |
| 13-2 | 2.37 | 0.16 | 10 | | | | | | | | | |
| 13-3 | 1.83 | 0.45 | 10 | | | | | | | | | |
| 13-4 | 2.65 | 0.17 | 10 | | | | | | | | | |
| 13-5 | 2.86 | 0.74 | 10 | | | | | | | | | |
| 13-6 | 1.73 | 0.15 | 10 | | | | | | | | | |
| 13-7 | 1.40 | 0.21 | 10 | | | | | | | | | |
| 13-8 | 1.49 | 0.11 | 10 | | | | | | | | | |
| 13-9 | | | | | | | | | | 8.76 | 0.56 | 30 |
| 13-10 | | | | | | | | | | 7.59 | 0.60 | 30 |
| 13-11 | | | | | | | | | | 10.57 | 1.23 | 30 |
| 13-12 | | | | | | | | | | 9.66 | 0.56 | 30 |
| 13-13 | | | | | | | | | | 10.51 | 0.69 | 30 |
| 13-14 | | | | | | | | | | 7.46 | 0.77 | 30 |
| 13-15 | | | | | | | | | | 9.98 | 1.05 | 30 |
| 13-16 | | | | 9.95 | n.a | 30 | 9.41 | 1.00 | 30 | | | |
| 13-17 | | | | | | | 21.32 | 1.29 | 30 | 20.08 | 4.87 | 30 |
| 13-18 | | | | | | | 13.29 | 0.89 | 30 | | | |
| 13-19 | | | | | | | 9.75 | 1.53 | 30 | | | |
| 13-20 | | | | 8.33 | 1.66 | 10 | | | | | | |
| 13-21 | | | | | | | 6.08 | 1.06 | 30 | | | |
| 13-22 | | | | | | | 5.85 | 0.95 | 30 | | | |
| 13-23 | | | | | | | 3.95 | 0.56 | 30 | | | |
| 13-24 | | | | 2.85 | 0.73 | 10 | | | | | | |

TABLE 19

Specific gravity, glass transition temperature, and melting temperature of thermoplastic compositions comprising microalgae and different polymers

| g/cm³ | Standard Deviation | Tg ° C. | Tm ° C. |
|---|---|---|---|
| 1.29 | 0.01 | 59.8 | 155.50 |
| 1.27 | 0.00 | 59 | 151.10 |
| 1.29 | 0.00 | 59 | 151.10 |
| 1.28 | 0.01 | 57.8 | 153.40 |
| 1.30 | 0.00 | 56.3 | 153.20 |
| 1.31 | 0.00 | 59 | 152.30 |
| 1.32 | 0.00 | 57.7 | 150.50 |
| 1.31 | 0.00 | 58.4 | 153.60 |
| 0.98 | 0.00 |  | 137.50 |
| 0.99 | 0.00 |  | 123.80 |
| 0.99 | 0.00 |  | 124.40 |
| 0.99 | 0.00 |  | 125.30 |
| 1.06 | 0.01 |  | 124.00 |
| 1.06 | 0.01 |  | n.a |
| 1.06 | 0.00 |  | 123.90 |
| 1.05 | 0.01 |  | 125.00 |
| 1.02 | 0.00 |  | 139.70 |
| 1.02 | 0.00 |  | 137.90 |
| 1.02 | 0.00 |  | 136.80 |
| 1.02 | 0.00 |  | 127.30 |
| 1.10 | 0.00 |  | 136.30 |
| 1.08 | 0.00 |  | 137.60 |
| 1.10 | 0.00 |  | 138.70 |
| 1.09 | 0.00 |  | 138.20 |

TABLE 20

Color scale results of microalgal biomass preparations and thermoplastic compositions comprising microalgae and different polymers

| Sample | Lightness to darkness scale (0 = black, 100 = white) | Red/magenta and green scale. (Negative values indicate green while positive values indicate magenta.) | Yellow and blue scale. (Negative values indicate blue and positive values indicate yellow.) |
|---|---|---|---|
| 13-1 | 29.02 | 7.61 | 13.00 |
| 13-2 | 25.96 | 7.73 | 12.19 |
| 13-3 | 30.51 | 8.91 | 15.36 |
| 13-4 | 33.81 | 9.15 | 16.28 |
| 13-5 | 28.33 | 8.23 | 14.36 |
| 13-6 | 27.08 | 8.63 | 14.48 |
| 13-7 | 31.65 | 9.38 | 17.88 |
| 13-8 | 34.84 | 9.74 | 18.61 |
| 13-9 | 35.07 | 6.65 | 13.55 |
| 13-10 | 33.64 | 7.96 | 14.23 |
| 13-11 | 33.49 | 6.70 | 12.04 |
| 13-12 | 37.04 | 7.78 | 14.27 |
| 13-13 | 31.94 | 8.42 | 15.23 |
| 13-14 | 29.12 | 8.07 | 13.69 |
| 13-15 | 26.47 | 7.37 | 11.81 |
| 13-16 | 35.50 | 8.66 | 16.34 |
| 13-17 | 37.61 | 6.64 | 12.48 |
| 13-18 | 40.37 | 8.49 | 15.99 |
| 13-19 | 38.33 | 7.28 | 13.24 |
| 13-20 | 45.21 | 7.33 | 14.09 |
| 13-21 | 32.55 | 8.35 | 13.84 |
| 13-22 | 37.70 | 9.03 | 17.11 |
| 13-23 | 33.98 | 8.85 | 16.30 |
| 13-24 | 38.55 | 9.28 | 18.95 |
| B | 47.23 | 11.96 | 29.97 |
| A | 91.50 | −0.50 | 12.30 |
| C | 62.86 | 7.26 | 21.88 |
| D | 42.58 | 9.92 | 24.17 |

Example 14

Microalgal Biomass

Microalgal biomass in Table 21 were prepared according to the methods of Examples 1 and 13 and were further milled to reduce particle size according to the indicated method.

TABLE 21

Microalgal biomass

| Sample | % Oil | Extraction Method | Milling | Soy Hull weight % | Fractionation |
|---|---|---|---|---|---|
| 21A | 8 | mechanical | Jet | 0 | unfractionated |
| 21B | 8 | mechanical | Jet | 0 | soluble |
| 21C | 8 | mechanical | Jet | 0 | insoluble |
| 21D | 9.2 | mechanical | Jet | 30 | unfractionated |
| 21E | 9.2 | mechanical | Jet | 30 | insoluble |
| 21F | 9.2 | mechanical | Bead | 30 | soluble |
| 21G | <2 | hexane | Bead | 0 | unfractionated |
| 21H | 7.2 | mechanical | Hammer | 15 | unfractionated |
| 21I | 7.2 | mechanical | Hammer | 15 | insoluble |
| 21J | 7.2 | mechanical | Hammer | 15 | soluble |
| 21K | <2 | mechanical, hexane | Hammer | 15 | unfractionated |
| 21M | <5 | mechanical | Hammer | 15 | insoluble |

Example 15

Thermoplastic Compositions Prepared with Oleaginous Microalgal Biomass and Linear Low Density Polyethylene Thermoplastic compositions were prepared by compounding microalgal biomass from Example 14 with linear low density polyethylene grafted with maleic anhydride (MAPE) and with linear low density polyethylene derived from sugar cane and were tested according to Example 13. Extruded neat pellets or extruded pellets containing biomass were subject to either injection molding or film cast extrusion, each procedure using a single screw extruder. Properties of the thermoplastic compositions are shown in Tables 22-28.

TABLE 22

Mechanical properties of injection molded thermoplastic composition prepared by compounding biomass with LLDPE or MAPE (LLDPE grafted with maleic anhydride polyethylene)

| Sample | % Biomass | Tensile Strength (psi) | SD | Elongation (%) | SD | Tensile Modulus (psi) | SD |
|---|---|---|---|---|---|---|---|
| neat | 0 | 1060 | 10 | 19.05 | 0.95 | 28400 | 1840 |
| 21G | 10 | 1020 | 15 | 16.70 | 1.46 | 40300 | 1560 |
| 21G | 20 | 946 | 10 | 17.03 | 1.88 | 55300 | 4740 |
| 21G | 40 | 784 | 9 | 8.58 | 1.07 | 96200 | 5890 |
| 21G | 5 | 1040 | 4 | 17.68 | 2.529 | 33600 | 1960 |
| 21G | 10 | 1010 | 29 | 16.37 | 1.77 | 41100 | 2080 |
| 21G | 20 | 975 | 9 | 14.41 | 1.98 | 63100 | 5870 |
| 21G-5% MAPE | 5 | 1150 | 7 | 15.426 | 1.578 | 40200 | 1770 |
| 21G-5% MAPE | 10 | 1170 | 16 | 15.8 | 2.11 | 43900 | 1690 |
| 21G-5% MAPE | 20 | 1180 | 17 | 13.64 | 1.84 | 60500 | 3140 |

SD = standard deviation

TABLE 23

Un-Notched Izod impact measurements of injection molded thermoplastic composition prepared by compounding biomass with LLDPE or MAPE (LLDPE grafted with maleic anhydride polyethylene)

| Sample | % Biomass | Un-Notched Izod Average (ft-lb)/in | SD (ft-lb)/in |
|---|---|---|---|
| neat | 0 | 7.096 | 0.97854177 |
| 21G | 10 | 8.4384 | 0.43170453 |
| 21G | 20 | 10.017 | 1.66312176 |
| 21G | 40 | 9.6526 | 0.34175693 |
| 21G | 5 | 7.722 | 0.85165427 |
| 21G | 10 | 9.1138 | 1.16461526 |
| 21G | 20 | 10.5128 | 1.44671272 |
| 21G-5% MAPE | 5 | 10.7414 | 1.95894814 |
| 21G-5% MAPE | 10 | 10.3316 | 1.3426259 |
| 21G-5% MAPE | 20 | 9.8782 | 0.20163755 |

TABLE 24

Specific gravity of injection molded thermoplastic composition prepared by compounding biomass with LLDPE or MAPE (LLDPE grafted with maleic anhydride polyethylene)

| Sample | % Biomass | Specific Gravity | SD |
|---|---|---|---|
| neat | 0 | 0.91542322 | 0.00095123 |
| 21G | 10 | 0.94520858 | 0.00284078 |
| 21G | 20 | 0.97728974 | 0.00389216 |
| 21G | 40 | 1.05576018 | 0.00294048 |
| 21G | 5 | 0.93938658 | 0.00102364 |
| 21G | 10 | 0.9446832 | 0.00255672 |
| 21G | 20 | 0.98280905 | 0.00099968 |
| 21G-5% MAPE | 5 | 0.93511599 | 0.00055696 |
| 21G-5% MAPE | 10 | 0.95060032 | 0.00068594 |
| 21G-5% MAPE | 20 | 0.98264282 | 0.00119576 |

TABLE 25

Water absorption properties of injection molded thermoplastic composition prepared by compounding biomass with LLDPE or MAPE (LLDPE grafted with maleic anhydride polyethylene)

| Sample | % Biomass | % Weight Change at 24 hrs | % Weight Change at 48 hrs | % Weight Change at 72 hrs | % Weight Change at 144 hrs | % Weight Change at 168 hrs |
|---|---|---|---|---|---|---|
| neat | 0 | 0.06273037 | 0.09410663 | | | 0.31364629 |
| 21G | 10 | 0.28006394 | 0.32551847 | | | 0.95381097 |
| 21G | 20 | 0.59580141 | −0.6804024 | | | 1.78157869 |
| 21G | 40 | 4.41792046 | 6.15454301 | | | 11.8731583 |
| 21G | 5 | 0.17654166 | 0.25329353 | 0.26097755 | 0.58336719 | 0.47591812 |
| 21G | 10 | 0.22627196 | 0.39979783 | 0.54311674 | 0.95024803 | 0.82215527 |
| 21G | 20 | 0.42061027 | 0.60193859 | 0.72528172 | 1.45039289 | 1.39956247 |
| 21G-5% MAPE | 5 | 0.1459117 | 0.27650486 | 0.28414643 | 0.56064421 | 0.49147732 |
| 21G-5% MAPE | 10 | 0.2265981 | 0.46072226 | 0.54380669 | 1.03472218 | 0.86105293 |
| 21G-5% MAPE | 20 | 0.3419628 | 0.56023081 | 0.69118617 | 1.28070886 | 1.18605775 |

TABLE 26

Melt flow index of thermoplastic pellets prepared by compounding biomass with LLDPE or MAPE (LLDPE grafted with maleic anhydride polyethylene)

| Sample | % Biomass | MFI g/10 min | SD |
|---|---|---|---|
| neat | 0 | 2.5 | 0.2 |
| 21G | 10 | 2.6 | 0 |
| 21G | 20 | 2.4 | 0.1 |
| 21G | 40 | 2 | 0.2 |
| 21G | 5 | 2.6 | 0 |
| 21G | 10 | 2.6 | 0 |
| 21G | 20 | 2.3 | 0.1 |
| 21G-5% MAPE | 5 | 1.7 | 0 |
| 21G-5% MAPE | 10 | 1.75 | 0.1 |
| 21G-5% MAPE | 20 | 1.3 | 0 |

TABLE 27

Sample index and seal strength of thermoplastic films prepared by compounding biomass with LLDPE or MAPE (LLDPE grafted with maleic anhydride polyethylene)

| Sample | % Biomass | Sample Thickness | Seal Strength Peak Load lbf | SD |
|---|---|---|---|---|
| neat | 0 | 2 mil | 3.91 | 0.29 |
| 21G | 10 | 4 mil | 5.46 | 1.16 |
| 21G | 20 | 10 mil | 4.04 | 1.68 |
| 21G | 40 | 11 mil | 9.22 | 0.72 |
| 21G | 5 | 2 mil | 5.65 | 0.18 |
| 21G | 10 | 3.5 mil | 4.94 | 0.51 |
| 21G-5% MAPE | 5 | 2 mil | 3.7 | 0.38 |
| 21G-5% MAPE | 20 | 2 mil | 3.37 | 0.31 |

TABLE 28

Strip tensile peak load measurements of films prepared by compounding biomass with LLDPE or MAPE (LLDPE grafted with maleic anhydride polyethylene)

| Sample | % Biomass | Strip Tensile Peak Load (lb) | SD |
|---|---|---|---|
| neat | 0 | 2.65 | 0.3 |
| 21G | 10 | 4.25 | 0.11 |

TABLE 28-continued

Strip tensile peak load measurements of films prepared by compounding biomass with LLDPE or MAPE (LLDPE grafted with maleic anhydride polyethylene)

| Sample | % Biomass | Strip Tensile Peak Load (lb) | SD |
|---|---|---|---|
| 21G | 20 | 10.89 | 0.17 |
| 21G | 40 | 0.68 | 0.68 |
| 21G | 5 | 3.52 | 0.06 |
| 21G | 10 | 4.17 | 0.38 |
| 21G-5% MAPE | 5 | 2.62 | 0.06 |
| 21G-5% MAPE | 20 | 2.57 | 0.06 |

Example 16

Acetylation

A 20.8 kg of sample 21H from Table 21 of Example 14 (20.0 kg as dry matter) was placed into Lödige multipurpose reactor. 3.04 kg of NaOH 50% (w/w) was poured from upper lid while the mass was being stirred. After ca. 45 minutes pumping of acetic anhydride (62.4 kg) was started. Addition was completed in 15 minutes. Reactor lid was closed and water steam heating was started. After ca. 45 minutes the target temperature of ca. 125° C. was achieved, which caused very moderate distillation of acetic acid. Reactor was kept running at ca. 125° C. for 6 hours. Mixture was allowed to cool down <100° C. Due to sample's viscosity, about 70 L of water was put to the reactor and resulting mixture was pumped into 1000 L IBC (intermediate bulk container) container filled with 500 L of water for further clean up. Mixture was allowed to sediment overnight. Water along with floating sludge was pumped on top of the product. Washing with water was repeated twice with ca. 700 L. The semi-dry product was shoveled into Lödige reactor and dried 26 hours until the solid content had reached ca. 95%. Yield: 14.16 kg Example 17

Proximate Analysis

Proximate analysis, performed in accordance with Official Methods of ACOC International (AOAC), were conducted on samples of dried *Prototheca moriformis* (UTEX 1435) biomass. The presscake samples were prepared by mechanical pressing the microalgae with an extruder to obtain the substantially de-oiled biomass. Fractionation of the biomass between water soluble and insoluble fractions was prepared as described in Example 1. Where noted, soybean hulls added by dry weight were used a press aid. Acid hydrolysis was conducted to assess total fat content (lipid/oil). Moisture was determined gravimetrically. Ash content was determined by crucible burning and analysis of the inorganic ash. Crude protein was determined by the amount of nitrogen released from burning of each biomass sample. Carbohydrate content was calculated by difference, taking the above known values for fat, moisture, ash, and crude protein and subtracting the total from 100.

TABLE 29

Percent moisture, protein, fat, ash and carbohydrate of biomass

| Sample | Moisture | Protein | Fat | Ash | Carbohydrate | Description |
|---|---|---|---|---|---|---|
| Soy hulls | 8.77 | 10.2 | 3.09 | 4.2 | 73.71 | Soy hulls |
| 21A | 4.59 | 9.2 | 8.47 | 5.9 | 71.83 | Presscake/0% soy hulls |
| 21A | 4.56 | 9 | 10.8 | 5.7 | 70.02 | Presscake/0% soy hulls |
| 21A | 1.62 | 13.7 | 6.14 | 3.7 | 74.85 | Presscake/0% soy hulls/ water insoluble fraction |
| 21A | 4.65 | 3.84 | 7.74 | 8.8 | 75 | Presscake/0% soy hulls/ water soluble fraction |
| 21D | 5.19 | 11.8 | 12.2 | 5.3 | 65.51 | Presscake/30% soy hulls |
| 21D | 3.72 | 11.5 | 7.8 | 5.3 | 71.7 | Presscake/15% soy hulls |
| 21D | 2.44 | 12.2 | 2.48 | 5.6 | 77.3 | Presscake/15% soy hulls/ further de-oiled by hexane extraction |
| 21D | 8.21 | 10.9 | 2.65 | 5.6 | 72.69 | 0% soy hulls/drum dried and bead milled/sample was not subjected to mechanical pressing and oil was instead extracted by solvent extraction |

Example 18

Water Analysis

Injection molded thermoplastic compositions were prepared using the plastic resin indicated in Table 23 (PLA=polylactic acid, LLDPE=linear low density polyethylene, HDPE=high density polyethylene) and were submerged in water up to one week for the indicated time periods. The change in weight was determined (Table 30) and their tensile properties were measured (Table 31).

TABLE 30

Analysis of weight change after water submersion

| Resin | Resin Grade | Sample | Fraction | % Material | % Weight Change at 24 hrs | % Weight Change at 48 hrs | % Weight Change at 72 hrs | % Weight Change at 96 hrs | % Weight Change at 168 hrs |
|---|---|---|---|---|---|---|---|---|---|
| PLA | NW 2003D | 21G | whole | 20 | 1.01986719 | 1.51664824 | 1.92462287 | 2.29310261 | 3.24065833 |
| PLA | NW 2003D | 21H | whole | 20 | 1.04788643 | 1.63410997 | 1.99757398 | 2.41679226 | 3.41555468 |
| PLA | NW 2003D | 21K | whole | 20 | 4.11472004 | 6.30722313 | 7.95480863 | 9.44390822 | 12.2853439 |
| PLA | NW 2003D | 21M | insoluble | 20 | 1.01035639 | 1.53026084 | 1.77881123 | 2.09602192 | 2.88076086 |
| PLA | NW 2003D | 21G | whole | 40 | 4.37563085 | 6.59067985 | 8.15913026 | 9.57705772 | 12.0353921 |
| PLA | NW 2003D | 21H | whole | 40 | 3.69844948 | 5.7422732 | 7.4001369 | 10.0326976 | 12.3420603 |
| PLA | NW 2003D | 21K | whole | 40 | 4.46308662 | 6.89853872 | 8.79728604 | 8.8475127 | 14.5344663 |
| PLA | NW 2003D | 21M | insoluble | 40 | 2.91524575 | 4.20106825 | 5.05828632 | 6.16759827 | 8.40218801 |
| LLDPE | ExxonM 1001.59 | 21G | whole | 20 | 0.25129 | 0.37248702 | 0.43973349 | 0.58786957 | 0.59233053 |
| LLDPE | ExxonM 1001.59 | 21H | whole | 20 | 0.2975805 | 0.35965065 | 0.39072582 | 0.48424901 | 0.652853 |
| LLDPE | ExxonM 1001.59 | 21K | whole | 20 | 0.28428936 | 0.35533712 | 0.31984728 | 0.63969931 | 0.58192507 |
| LLDPE | ExxonM 1001.59 | 21M | insoluble | 20 | 0.33924673 | 0.52670611 | 0.52224501 | 0.69632588 | 0.76773452 |
| LLDPE | ExxonM 1001.59 | 21G | whole | 40 | 3.35584646 | 4.91163551 | 6.04381784 | 6.87860634 | 9.25308945 |
| LLDPE | ExxonM 1001.59 | 21H | whole | 40 | 1.25808628 | 1.5878864 | 1.92585738 | 2.35334057 | 2.98849991 |
| LLDPE | ExxonM 1001.59 | 21K | whole | 40 | 1.44914798 | 2.01727977 | 2.37845159 | 2.93427957 | 3.78669161 |
| LLDPE | ExxonM 1001.59 | 21M | insoluble | 40 | 1.15316871 | 1.5578899 | 1.73786778 | 2.15097527 | 2.5107513 |
| HDPE | Marlex 6007 | 21G | whole | 20 | 0.12650887 | 0.2224099 | 0.32714256 | 0.48416162 | 0.52777455 |
| HDPE | Marlex 6007 | 21H | whole | 20 | 0.29925647 | 0.39467545 | 0.42939038 | 0.6635612 | 0.69821628 |
| HDPE | Marlex 6007 | 21K | whole | 20 | 0.15968293 | 0.25460121 | 0.29354408 | 0.29790484 | 0.43166709 |
| HDPE | Marlex 6007 | 21M | insoluble | 20 | 0.28308334 | 0.35279793 | 0.48354952 | 0.63165537 | 0.58804411 |
| HDPE | Marlex 6007 | 21G | whole | 40 | 3.20267778 | 5.31937341 | 7.16467624 | 9.04928824 | 11.9489419 |
| HDPE | Marlex 6007 | 21H | whole | 40 | 1.64096994 | 2.86170397 | 3.94231223 | 5.25107859 | 8.46099253 |
| HDPE | Marlex 6007 | 21K | whole | 40 | 1.44982461 | 2.39143538 | 3.35274715 | 4.51099417 | 7.33190359 |
| HDPE | Marlex 6007 | 21M | insoluble | 40 | 1.33638154 | 1.95251399 | 2.44467556 | 3.18883728 | 4.90930638 |

TABLE 31

Analysis of effect of water submersion on mechanical properties

| Resin | Resin Grade | Sample | Fraction | % Material | Tensile Strength (psi) | SD | Elongation (%) | SD | Tensile Modulus (psi) | SD |
|---|---|---|---|---|---|---|---|---|---|---|
| PLA | NW 2003D | 21G | whole | 20 | 4200 | 168 | 1.71 | 0.07 | 419000 | 17700 |
| PLA | NW 2003D | 21H | whole | 20 | 3470 | 134 | 1.99 | 0.28 | 421000 | 16000 |
| PLA | NW 2003D | 21K | whole | 20 | 2730 | 1200 | 2.67 | 0.89 | 330000 | 110000 |
| PLA | NW 2003D | 21M | insoluble | 20 | 4000 | 133 | 1.54 | 0.06 | 488000 | 10800 |
| PLA | NW 2003D | 21G | whole | 40 | 2340 | 39 | 13.47 | 2.10 | 223000 | 7280 |
| PLA | NW 2003D | 21H | whole | 40 | 1810 | 32 | 7.58 | 1.20 | 221000 | 6350 |
| PLA | NW 2003D | 21K | whole | 40 | 2010 | 74 | 3.34 | 0.41 | 244000 | 4530 |
| PLA | NW 2003D | 21M | insoluble | 40 | 2460 | 48 | 2.40 | 0.31 | 440000 | 29600 |
| LLDPE | ExxonM 1001.59 | 21G | whole | 20 | 1190 | 16 | 22.22 | 3.18 | 51600 | 2370 |
| LLDPE | ExxonM 1001.59 | 21H | whole | 20 | 1120 | 18 | 26.88 | 1.64 | 43000 | 2310 |
| LLDPE | ExxonM 1001.59 | 21K | whole | 20 | 1150 | 26 | 24.33 | 8.18 | 48300 | 1990 |
| LLDPE | ExxonM 1001.59 | 21M | insoluble | 20 | 1170 | 28 | 22.28 | 5.62 | 52600 | 3650 |
| LLDPE | ExxonM 1001.59 | 21G | whole | 40 | 839 | 11 | 21.44 | 2.64 | 43300 | 3520 |
| LLDPE | ExxonM 1001.59 | 21H | whole | 40 | 937 | 18 | 21.25 | 2.77 | 52500 | 2610 |
| LLDPE | ExxonM 1001.59 | 21K | whole | 40 | 944 | 27 | 21.42 | 2.47 | 62300 | 9380 |
| LLDPE | ExxonM 1001.59 | 21M | insoluble | 40 | 876 | 18 | 16.00 | 0.41 | 59700 | 4500 |
| HDPE | Marlex 6007 | 21G | whole | 20 | 2950 | 33 | 11.40 | 1.00 | 234000 | 10500 |
| HDPE | Marlex 6007 | 21H | whole | 20 | 2860 | 51 | 12.97 | 1.95 | 224000 | 11000 |
| HDPE | Marlex 6007 | 21K | whole | 20 | 2900 | 58 | 11.20 | 2.06 | 242000 | 15300 |
| HDPE | Marlex 6007 | 21M | insoluble | 20 | 2760 | 44 | 11.49 | 0.36 | 223000 | 7630 |
| HDPE | Marlex 6007 | 21G | whole | 40 | 1830 | 19 | 17.99 | 1.07 | 86500 | 4750 |

TABLE 31-continued

Analysis of effect of water submersion on mechanical properties

| Resin | Resin Grade | Sample | Fraction | % Material | Tensile Strength (psi) | SD | Elongation (%) | SD | Tensile Modulus (psi) | SD |
|---|---|---|---|---|---|---|---|---|---|---|
| HDPE | Marlex 6007 | 21H | whole | 40 | 2030 | 16 | 15.01 | 0.68 | 136000 | 3650 |
| HDPE | Marlex 6007 | 21K | whole | 40 | 2160 | 8 | 11.14 | 0.58 | 196000 | 4560 |
| HDPE | Marlex 6007 | 21M | insoluble | 40 | 2140 | 23 | 10.18 | 0.92 | 238000 | 2640 |

Example 19

Hand Sheets Prepared with Eucalyptus Fiber and Microalgal Biomass

Eucalyptus fiber hand sheets containing microalgal biomass and different amounts of cationic polymeric retention aid were prepared by static formation. The microalgal biomass used was generated through mechanical pressing of *Prototheca moriformis* (UTEX 1435) with soybean hull bulking agents. In some paper formulations, the insoluble polymeric fraction obtained through wet fractionation of biomass as per Example 1 was used. Where used, cationic polyacrylamide (cPAM) was obtained from Ashland Inc. Physical, technical, and barrier properties of the static-formed hand sheets were evaluated according to SCAN-C or ISO standards. Data are shown in Tables 33-36. Unless indicated otherwise, values reported are means and standard deviations recorded from measurements conducted on ten distinct hand sheets per formulation.

TABLE 32

Formulations of Eucalyptus Hand Sheets

| Formulation | % Eucalyptus fiber | % Microalgal Biomass | Microalgal Biomass Fraction | Retention Aid | Retention Conc. |
|---|---|---|---|---|---|
| HS1 | 100 | 0 | | cPAM | 2 kg/tn |
| HS2 | 80 | 20 | whole | cPAM | 2 kg/tn |
| HS3 | 80 | 20 | insoluble | cPAM | 2 kg/tn |
| HS4 | 80 | 20 | insoluble | none | 0 |
| HS5 | 80 | 20 | whole | none | 0 |
| HS6 | 100 | 0 | | cPAM | 200 g/tn |
| HS7 | 80 | 20 | whole | cPAM | 200 g/tn |
| HS8 | 80 | 20 | insoluble | cPAM | 200 g/tn |

TABLE 33

Paper physical properties of eucalyptus fiber hand sheets with and without microalgal biomass.

| Formulation | Basis weight (g/m$^2$) | | Thickness (μm) | | Density (kg/m$^3$) | | Bulk (cm$^3$/g) | |
|---|---|---|---|---|---|---|---|---|
| | Mean | st. dev. | Mean | st. dev. | Mean | st. dev. | Mean | st. dev. |
| HS1 | 59.61 | 0.33 | 87.34 | 1.40 | 682.67 | 9.72 | 1.47 | 0.02 |
| HS2 | 66.92 | 0.32 | 129.16 | 1.99 | 518.20 | 7.55 | 1.93 | 0.03 |
| HS3 | 71.63 | 0.50 | 132.70 | 3.22 | 540.06 | 11.20 | 1.85 | 0.04 |
| HS4 | 59.93 | 0.43 | 125.38 | 2.97 | 478.17 | 11.02 | 2.09 | 0.05 |
| HS5 | 60.40 | 0.36 | 139.34 | 2.53 | 434.20 | 7.06 | 2.30 | 0.04 |
| HS6 | 59.81 | 0.45 | 88.22 | 0.71 | 677.63 | 5.24 | 1.48 | 0.01 |
| HS7 | 60.02 | 0.34 | 139.74 | 3.77 | 429.76 | 11.53 | 2.33 | 0.06 |
| HS8 | 60.41 | 0.30 | 122.40 | 2.29 | 493.67 | 8.38 | 2.03 | 0.03 |

TABLE 34

Paper technical properties of eucalyptus fiber hand sheets with and without microalgal biomass.

| | | HS1 | HS2 | HS3 | HS4 | HS5 | HS6 | HS7 | HS8 |
|---|---|---|---|---|---|---|---|---|---|
| Tensile Strength (N/m) | Mean | 3240 | 2800 | 3430 | 3170 | 2640 | 3820 | 2530 | 3090 |
| | Std. Dev. | 85.7 | 172 | 146 | 132 | 156 | 128 | 137 | 91.4 |
| Tensile Index (Nm/g) | Mean | 54.3 | 41.9 | 47.8 | 52.9 | 43.7 | 64 | 42.2 | 51.4 |
| | Std. Dev. | 1.44 | 2.56 | 2.03 | 2.2 | 2.59 | 2.14 | 2.29 | 1.52 |
| Energy to Break (J/m$^2$) | Mean | 85.7 | 62.1 | 89.4 | 88 | 63.1 | 108 | 55.6 | 82.9 |
| | Std. Dev. | 7.77 | 12.8 | 11.6 | 12.7 | 12.3 | 8.72 | 8.42 | 4.05 |
| Energy to Break Index (mJ/g) | Mean | 1.44 | 0.928 | 1.25 | 1.47 | 1.04 | 1.8 | 0.925 | 1.38 |
| | Std. Dev. | 0.13 | 0.191 | 0.162 | 0.213 | 0.203 | 0.146 | 0.14 | 0.067 |
| Strain at Break % | Mean | 3.79 | 3.07 | 3.64 | 3.90 | 3.36 | 4.01 | 3.06 | 3.77 |
| | Std. Dev. | 0.30 | 0.45 | 0.32 | 0.42 | 0.48 | 0.22 | 0.32 | 0.15 |
| Modulus of Elasticity E (N/mm$^2$) | Mean | 4080 | 2660 | 2850 | 2620 | 2100 | 4430 | 2100 | 2630 |
| | Std. Dev. | 160 | 70.3 | 64.4 | 90.4 | 105 | 138 | 65.4 | 112 |
| Width (mm) | | 15 | 15 | 15 | 15 | 15 | 15 | 15 | 15 |
| Breadth (mm) | | 0.087 | 0.129 | 0.133 | 0.125 | 0.139 | 0.0882 | 0.14 | 0.122 |

Bendtsen porosity measurements were performed with a defined air pressure applied to the surface of the sheet and with a defined measurement area (10 cm$^2$). Air permeance was measured from the bottom (wire facing) and top surfaces of the hand sheet. The values shown in Table 35 are the mean and standard deviation of measurements of five distinct hand sheets.

TABLE 35

Paper barrier properties of eucalyptus fiber hand sheets with and without microalgal biomass.

| Formulation | Hand Sheet Surface | Air Permeance ml/min (10 cm$^2$) | |
|---|---|---|---|
| | | Mean | Std. Dev. |
| HS1 | bottom | 874.8 | 23.97 |
| HS1 | top | 876.4 | 25.77 |
| HS2 | bottom | 674 | 27.64 |
| HS2 | top | 671.6 | 27.29 |
| HS3 | bottom | 526.2 | 11.92 |
| HS3 | top | 527 | 14.09 |
| HS4 | bottom | 191.6 | 11.91 |
| HS4 | top | 192.6 | 10.78 |
| HS5 | bottom | 498.8 | 42.35 |
| HS5 | top | 497.8 | 43.51 |
| HS6 | bottom | 398.4 | 21.70 |
| HS6 | top | 397.4 | 19.55 |
| HS7 | bottom | 561.4 | 33.21 |
| HS7 | top | 556.8 | 35.97 |
| HS8 | bottom | 324.4 | 9.10 |
| HS8 | top | 322 | 9.43 |

Bendtsen roughness was measured from both the bottom (wire facing) and top surfaces of the hand sheet. The values shown in Table 36 are the mean and standard deviation of measurements of five distinct hand sheets.

TABLE 36

Paper physical properties of eucalyptus fiber hand sheets with and without microalgal biomass.

| Formulation | Hand Sheet Surface | Compensated Roughness, ml/min | |
|---|---|---|---|
| | | Mean | Std. Dev. |
| HS1 | bottom | 146.2 | 14.99 |
| HS1 | top | 778.35 | 82.48 |
| HS2 | bottom | 351.52 | 45.86 |
| HS3 | bottom | 324.72 | 66.67 |
| HS4 | bottom | 223 | 53.31 |
| HS5 | bottom | 448.12 | 74.62 |
| HS6 | bottom | 75 | 4.61 |
| HS7 | bottom | 554.35 | 151.40 |
| HS8 | bottom | 254 | 39.49 |

Color properties, brightness, opacity, light scattering coefficients, and the light absorption coefficients were evaluated for both the bottom (wire facing) and top surfaces of the hand sheets. Presented in Table 37 are L* a* b* values, measured according to ISO 5361, for the hand sheets described in Table 32. L* is a measure of perceived lightness. The scale of L* is 0-100. a* is a measure of the hue on the red/green axis. b* is a measure of hue on the yellow/blue axis. 10° was the viewing angle used for these measurements. Table 38 provides the brightness, opacity, light scattering coefficients, and light absorption coefficients of hand sheets described in Table 32.

TABLE 37

Color Properties of Hand Sheets prepared with and without microalgal biomass

| For-mula-tion | Hand Sheet Surface | L* C/2 | | a* C/2 | | b* C/2 | |
|---|---|---|---|---|---|---|---|
| | | Mean | Std. Dev. | Mean | Std. Dev. | Mean | Std. Dev. |
| HS1 | bottom | 96.21 | 0.03 | −0.98 | 0.02 | 4.44 | 0.06 |
| HS1 | top | 96.3 | 0.02 | −0.98 | 0.03 | 4.39 | 0.06 |
| HS2 | bottom | 87.7 | 0.06 | 0.78 | 0.02 | 10.21 | 0.10 |
| HS2 | top | 87.6 | 0.06 | 0.81 | 0.02 | 10.4 | 0.12 |
| HS3 | bottom | 82.9 | 0.05 | 1.60 | 0.01 | 13.2 | 0.05 |
| HS3 | top | 83.0 | 0.06 | 1.59 | 0.03 | 13.1 | 0.06 |
| HS4 | bottom | 79.8 | 0.05 | 2.24 | 0.03 | 15.6 | 0.08 |
| HS4 | top | 81.1 | 0.08 | 2.01 | 0.04 | 13.1 | 0.12 |
| HS5 | bottom | 84.5 | 0.14 | 1.38 | 0.05 | 13.2 | 0.20 |
| HS5 | top | 84.9 | 0.13 | 1.41 | 0.04 | 12.2 | 0.19 |
| HS6 | bottom | 96.7 | 0.02 | −0.89 | 0.01 | 4.4 | 0.02 |
| HS6 | top | 96.7 | 0.01 | −0.89 | 0.01 | 4.31 | 0.02 |
| HS7 | bottom | 83.9 | 0.12 | 1.57 | 0.03 | 13.22 | 0.13 |
| HS7 | top | 84.2 | 0.14 | 1.60 | 0.03 | 12.4 | 0.16 |
| HS8 | bottom | 80.6 | 0.07 | 2.06 | 0.03 | 14.8 | 0.04 |
| HS8 | top | 81.3 | 0.08 | 1.93 | 0.03 | 13.4 | 0.12 |

TABLE 38

Properties of Hand Sheets prepared with and without microalgal biomass

| For-mula-tion | Hand Sheet Surface | Brightness | | Opacity | | Scattering coefficient | | Absorption coefficient | |
|---|---|---|---|---|---|---|---|---|---|
| | | Mean | Std. Dev. | Mean | Std. Dev. | Mean | Std. Dev. | Mean | Std. Dev. |
| HS1 | bottom | 84.42 | 0.15 | 74.81 | 0.36 | 35.86 | 0.56 | 0.18 | 0 |
| HS1 | top | 84.6 | 0.13 | 75.1 | 0.65 | 36.4 | 1.02 | 0.18 | 0.00 |
| HS2 | bottom | 59.9 | 0.23 | 89.1 | 0.31 | 35.0 | 0.57 | 1.99 | 0.03 |
| HS2 | top | 59.5 | 0.22 | 89.2 | 0.29 | 35.1 | 0.53 | 2.03 | 0.03 |
| HS3 | bottom | 48.7 | 0.12 | 93.3 | 0.22 | 31.6 | 0.44 | 3.69 | 0.05 |
| HS3 | top | 48.9 | 0.12 | 93.3 | 0.15 | 31.7 | 0.30 | 3.65 | 0.03 |
| HS4 | bottom | 41.8 | 0.12 | 90.5 | 0.11 | 27.6 | 0.16 | 4.69 | 0.03 |
| HS4 | top | 45.9 | 0.20 | 90.4 | 0.31 | 29.4 | 0.46 | 4.27 | 0.07 |
| HS5 | bottom | 51.3 | 0.41 | 88.2 | 0.32 | 31.3 | 0.46 | 2.96 | 0.04 |
| HS5 | top | 52.9 | 0.38 | 88.5 | 0.36 | 32.4 | 0.55 | 2.89 | 0.05 |
| HS6 | bottom | 85.6 | 0.03 | 74.7 | 0.37 | 36.9 | 0.59 | 0.14 | 0.00 |
| HS6 | top | 85.7 | 0.05 | 75.0 | 0.32 | 37.5 | 0.54 | 0.14 | 0.00 |
| HS7 | bottom | 50.3 | 0.29 | 88.2 | 0.13 | 30.5 | 0.18 | 3.11 | 0.02 |
| HS7 | top | 51.5 | 0.40 | 88.2 | 0.18 | 30.9 | 0.26 | 3.02 | 0.03 |
| HS8 | bottom | 43.7 | 0.11 | 91.0 | 0.24 | 29.5 | 0.37 | 4.58 | 0.06 |
| HS8 | top | 46.0 | 0.23 | 91.0 | 0.34 | 30.7 | 0.55 | 4.35 | 0.08 |

Example 20

Absorbent Materials Prepared with Microalgal Biomass

This example describes production and testing of absorbent material produced from microalgal biomass. Different preparations of *Prototheca moriformis* (UTEX 1435) microalgal biomass were subjected to anionization and crosslinking. In all cases, carboxymethylation was selected as the form of anionization and glyoxal was the crosslinker used. Crosslinking with glyoxal was performed using a Lödige reactor. Dry carboxymethylation was performed as described in Example 7. Materials were dried with an oven dryer. Variables assessed included the degree of carboxymethylation substitution, the amount of glyoxal used, and the order that the two chemistries were performed (either anionization first, followed by crosslinking or crosslinking first, followed by anionization). Additional variables included the processing conditions by which the microagal biomass was deoiled and whether the microalgal biomass was water-fractionated. The water absorption capacity and charge density of the absorbent materials were measured as described in Example 7. The saline absorption capacity was measured as weight gain by soaking the material in a 0.9% NaCl solution for the time indicated then weighting the wet material before and after drying. The absorption capacity was calculated as ((wet weight−dry weight)/dry weight)×100%.

Table 39 presents water absorption capacity and charge density of different absorbent materials prepared from *Prototheca moriformis* (UTEX 1435) microalgal biomass. The biomass used in Samples AB1-AB14 was generated through mechanical pressing without soybean hull bulking agents. N.m. indicates that values were not measured. For Table 39, "Whole" refers to the unfractionated, pressed, milled biomass. "Insoluble" refers to pressed and fractionated milled biomass that is insoluble in water.

TABLE 39

Water absorption capacity and charge density of absorbent materials prepared with microalgal biomass.

| Sample | Fraction | Crosslink order | % Crosslinker Used | CM DS | Charge Density (meq/g) | Water absorption capacity after indicated time (hrs) | | | |
|---|---|---|---|---|---|---|---|---|---|
| | | | | | | 0.17 | 1 | 4 | 24 |
| AB1 | whole | Second | 10 | 0.5 | 0 | 40 | 180 | 210 | 210 |
| AB2 | whole | Second | 15 | 0.5 | −0.4 | 20 | 120 | 200 | 205 |
| AB3 | whole | Second | 10 | 1.3 | −1.3 | 140 | 410 | 490 | 560 |
| AB4 | whole | Second | 20 | 1.3 | −0.8 | 205 | 220 | 260 | 380 |
| AB5 | insoluble | Second | 10 | 0.6 | n.m. | 410 | 980 | 820 | 810 |
| AB6 | insoluble | Second | 10 | 1.3 | n.m. | 590 | 1230 | 1380 | 1370 |
| AB7 | whole | First | 5 | 0.6 | −1 | 200 | 1235 | 1250 | 1410 |
| AB8 | whole | First | 10 | 0.6 | −2.4 | 360 | 900 | 970 | 1060 |
| AB9 | insoluble | First | 5 | 0.3 | n.m. | n.m. | n.m. | 1060 | n.m. |
| AB10 | insoluble | First | 2 | 0.3 | n.m. | n.m. | n.m. | 1310 | n.m. |
| AB11 | insoluble | First | 7 | 0.3 | n.m. | n.m. | n.m. | 1050 | n.m. |
| AB12 | insoluble | First | 5 | 0.6 | n.m. | n.m. | n.m. | 1380 | n.m. |
| AB13 | insoluble | First | 2 | 0.6 | n.m. | n.m. | n.m. | 1010 | n.m. |
| AB14 | insoluble | First | 7 | 0.6 | n.m. | n.m. | n.m. | 1410 | n.m. |

Table 40 provides the formulation details of 8 absorbent material samples prepared with microalgal biomass that was generated through mechanical pressing with soyhull fibers added at 15% by weight. As with Samples AB1-AB14, the absorbent materials AB15-AB22 were crosslinked with glyoxal and carboxymethylated. Table 41 presents the water absorption capacity of these samples. Table 42 presents the saline absorption capacity of Samples AB17, AB21, and AB22. For each sample, the measurements of three technical replicates are shown. For Table 40, "Whole" refers to the unfractionated, pressed, milled biomass. "Insoluble" refers to pressed, milled, and fractionated biomass that is insoluble in water.

TABLE 40

Formulations of absorbent materials prepared with microalgal biomass mechanically pressed with soyhull fibers

| Sample | Fraction | Crosslink order | % Crosslinker | CM DS |
|---|---|---|---|---|
| AB15 | whole | Second | 2 | 0.3 |
| AB16 | whole | Second | 5 | 0.3 |
| AB17 | insoluble | Second | 2 | 0.3 |
| AB18 | insoluble | Second | 5 | 0.3 |
| AB19 | whole | Second | 2 | 0.6 |
| AB20 | whole | Second | 5 | 0.6 |
| AB21 | insoluble | Second | 2 | 0.6 |
| AB22 | insoluble | Second | 5 | 0.6 |

TABLE 41

Water absorption capacity of Samples AB15-AB22

| Sample | Water absorption capacity after indicated time (min) | | | | | | | | |
|---|---|---|---|---|---|---|---|---|---|
| | 15 | | | 60 | | | 240 | | |
| AB15 | 604 | 606 | 767 | 836 | 907 | 845 | 804 | 967 | 939 |
| AB16 | 671 | 733 | 729 | 701 | 806 | 794 | 1201 | 1122 | 1171 |
| AB17 | 653 | 664 | 703 | 851 | 931 | 896 | 1187 | 1197 | 1261 |
| AB18 | 729 | 718 | 651 | 836 | 821 | 841 | 1204 | 1087 | 1211 |
| AB19 | 530 | 577 | 555 | 727 | 702 | 810 | 849 | 912 | 953 |
| AB20 | 590 | 684 | 617 | 772 | 851 | 795 | 1004 | 1067 | 975 |
| AB21 | 773 | 740 | 715 | 1012 | 853 | 908 | 1367 | 1329 | 1349 |
| AB22 | 607 | 701 | 720 | 1092 | 1043 | 1016 | 1258 | 1277 | 1309 |

TABLE 42

Saline absorption capacity of Samples AB15-AB22

| Sample | Saline absorption capacity after indicated time (min) | | | | | | | | |
|---|---|---|---|---|---|---|---|---|---|
| | 15 | | | 60 | | | 240 | | |
| AB17 | 516 | 488 | 504 | 635 | 607 | 680 | 771 | 795 | 754 |
| AB21 | 614 | 509 | 583 | 7.5 | 645 | 695 | 851 | 788 | 812 |
| AB22 | 468 | 475 | 484 | 628 | 733 | 592 | 801 | 774 | 788 |

Example 21

Thermoplastic Compositions Comprising Acetylated Microalgal Biomass

This example describes the use of covalently modified microalgal biomass to produce thermoplastic compositions. *Prototheca moriformis* (UTEX 1435) was cultured under heterotrophic conditions such as those described in WO2008/151149, WO2010/063032, and WO2011/150411. Upon cultivation, the microalgae was dried then mechanically pressed to extract oil with 15% soybean hulls added by dry weight as a press aid. The resulting microalgal biomass with soybean hull plant polymers retained 7.2% residual oil. This biomass was then milled to a final average particle size of 300 microns. The biomass was then split into two fractions. One fraction ("unfractionated biomass") was acetylated as in Example 2. The DS of acetylation was 2.3. The other fraction was subjected to water-based fraction as described in Example 1, then acetylated as in Example 2. The DS of acetylation was 2.1.

TABLE 43

Formulation of thermoplastic materials made with PLA and unfractionated acetylated microalgal biomass

| Sample | PLA Resin | Weight % Acetylated Biomass | Weight % PLA Resin | Weight % TEC |
|---|---|---|---|---|
| 21-1 | NatureWorks 3051D | 0 | 100 | 0 |
| 21-2 | | 35 | 60 | 5 |
| 21-3 | | 33 | 60 | 7 |
| 21-4 | | 30 | 60 | 10 |
| 21-5 | | 27 | 60 | 13 |
| 21-6 | | 20 | 80 | 0 |
| 21-7 | | 40 | 60 | 0 |
| 21-8 | | 60 | 40 | 0 |
| 21-9 | | 0 | 91.7 | 8.3 |
| 21-10 | | 0 | 88.3 | 11.7 |
| 21-11 | | 0 | 78.3 | 21.7 |
| 21-12 | | 35 | 60 | 5 |
| 21-13 | NatureWorks 3051D/MAH-g-2002D | 35 | 60 | 5 |
| 21-14 | NatureWorks 3051D | 40 | 60 | 0 |
| 21-15 | NatureWorks 3051D/MAH-g-2002D | 40 | 60 | 0 |

TABLE 44

Properties of thermoplastic materials made with PLA and unfractionated acetylated microalgal biomass

| Sample | Max tensile strength (MPA) | Max tensile strength (MPA) St. Dev. | Tensile modulus (GPA) | Tensile modulus (GPA) St. Dev. | Max elongation (%) | Max elongation St. Dev. | Impact Strength (kJ/m2) | Impact Strength (kJ/m2) St. Dev. |
|---|---|---|---|---|---|---|---|---|
| 21-1 | 60.2 | 0.8 | 3.6 | 0.2 | 4.8 | 1.2 | 15 | 1.6 |
| 21-2 | 35.0 | 0.5 | 3.8 | 0.53 | 2.1 | 0.7 | n.d. | n.d. |
| 21-3 | 33.0 | n.d. | 3.3 | 0.29 | 1.7 | 0.2 | n.d. | n.d. |
| 21-4 | 21.6 | 1.4 | 1.8 | 0.23 | 92 | n.d. | n.d. | n.d. |
| 21-5 | 9.9 | n.d. | 0.6 | n.d. | 200 | n.d. | n.d. | n.d. |
| 21-6 | 45.7 | 1.4 | 3.7 | 0.29 | 2.4 | 0.5 | n.d. | n.d. |
| 21-7 | 36.5 | 1.1 | 3.4 | 0.19 | 1.7 | 0.2 | n.d. | n.d. |
| 21-8 | n.d. | n.d. | n.d. | n.d. | n.d. | n.d. | n.d. | n.d. |
| 21-9 | 47.5 | 1.4 | 2.9 | 0.53 | 5.7 | 1.6 | n.d. | n.d. |
| 21-10 | 35.7 | 3.4 | 2.1 | 0.47 | 180 | n.d. | n.d. | n.d. |
| 21-11 | 6.2 | n.d. | 0.01 | n.d. | 180 | n.d. | n.d. | n.d. |
| 21-12 | 31.9 | 0.3 | 3.4 | 0.15 | 1.2 | 0.1 | 5.9 | 0.7 |
| 21-13 | 29.6 | 0.2 | 3.2 | 0.06 | 1.2 | 0 | 3.7 | 1.0 |
| 21-14 | 30.8 | 2.4 | 3.4 | 0.11 | 1.1 | 0.2 | 4.4 | 0.8 |
| 21-15 | 31.7 | 0.2 | 3.4 | 0.17 | 1.2 | 0.1 | 4.3 | 0.6 |

Table 43 provides weight-based formulations of thermoplastic materials prepared with acetylated unfractionated microalgal biomass containing soybean hulls. Unless otherwise indicated, NatureWorks 3051D PLA was used in these preparations. MAH-g-2002D refers to maleic anhydride grafted PLA. Triethyl citrate was included in preparation of some samples. For each sample, the indicated materials were dry mixed. Compounding and extrusion of the blends was performed with a Brabender Plastic-Corder PL 2100-6 melt mixer. Thermoplastic granules were prepared with a knife mill grinder. Tensile test bars were generated with a Haake MiniJet Injection Moulding Machine. Tensile and Charpy impact strength properties were tested according to ISO standards. Results from these tests are shown in Table 44.

Table 45 provides weight-based formulations of thermoplastic materials prepared with either unfractionated acetylated microalgal biomass containing soybean hulls or water-insoluble fractionated acetylated microalgal biomass containing soybean hulls. Unless otherwise indicated, NatureWorks 3051D PLA was used in these preparations. MAH-g-2002D refers to maleic anhydride grafted PLA. Triethyl citrate was included in preparation of some samples. For each sample, compounding and extrusion of the blends was performed with a Berstorff twin-screw extruder. Tensile test bars were generated via injection molding with an Engel moulder. Tensile, Charpy impact strength, and heat deflection properties were tested according to ISO standards. Results from these tests are shown in Table 46.

TABLE 45

Formulation of thermoplastic materials made with PLA and acetylated microalgal biomass

| Sample | PLA Resin | Algal biomass fraction | Weight % Acetylated Biomass | Weight % PLA Resin | Weight % TEC |
|---|---|---|---|---|---|
| 21-16 | NatureWorks 3051D | none | 0 | 100 | 0 |
| 21-17 | | unfractionated | 19 | 80 | 1 |
| 21-18 | | unfractionated | 38 | 60 | 2 |
| 21-19 | | unfractionated | 57 | 40 | 3 |
| 21-20 | | unfractionated | 76 | 20 | 4 |
| 21-21 | NatureWorks 3051D/ MAH-g-2002D | unfractionated | 38 | 60 | 2 |
| 21-22 | NatureWorks 3051D | unfractionated | 20 | 80 | 0 |
| 21-23 | | unfractionated | 40 | 60 | 0 |
| 21-24 | | unfractionated | 60 | 40 | 0 |
| 21-25 | NatureWorks 3051D/ MAH-g-2002D | unfractionated | 40 | 60 | 0 |
| 21-26 | NatureWorks 3051D | unfractionated | 40 | 60 | 0 |
| 21-27 | | unfractionated | 38 | 60 | 2 |
| 21-28 | | unfractionated | 38 | 60 | 2 |
| 21-29 | | water insoluble | 20 | 80 | 0 |
| 21-30 | | water insoluble | 50 | 50 | 0 |
| 21-31 | | water insoluble | 80 | 20 | 0 |
| 21-32 | | none | 0 | 100 | 0 |
| 21-33 | | unfractionated | 80 | 20 | 0 |

TABLE 46

Formulation of thermoplastic materials made with PLA and acetylated microalgal biomass

| Sample | Max tensile strength (MPA) | Max tensile strength (MPA) St. Dev. | Tensile modulus (GPA) | Tensile modulus (GPA) St. Dev. | Max elongation (%) | Max elongation St. Dev. | Impact Strength (kJ/m2) | Impact Strength (kJ/m2) St. Dev. | HDT (1.8 Mpa, °C.) |
|---|---|---|---|---|---|---|---|---|---|
| 21-16 | 60.2 | 0.8 | 3.60 | 0.20 | 4.8 | 1.2 | 15 | 1.6 | 53 |
| 21-17 | 43.0 | 0.4 | 3.50 | 0.10 | 2.6 | 0.1 | 9.4 | 1.1 | 49 |
| 21-18 | 32.0 | 1.6 | 3.40 | 0.34 | 1.3 | 0.1 | 5.9 | 0.8 | 46 |
| 21-19 | 27.1 | 0.5 | 3.50 | 0.26 | 1.0 | 0 | 4.1 | 0.7 | n.d. |
| 21-20 | 21.2 | 0.6 | 3.00 | 0.10 | 0.8 | 0 | 2.3 | 0.3 | n.d. |
| 21-21 | 33.0 | 0.3 | 3.60 | 0.16 | 1.4 | 0.1 | 5.83 | 0.71 | 46 |
| 21-22 | 42.9 | 0.3 | 3.56 | 0.01 | 2.5 | 0.2 | 9.01 | 0.97 | 50 |
| 21-23 | 33.2 | 0.5 | 3.43 | 0.15 | 1.3 | 0.1 | 5.79 | 1.06 | 49 |
| 21-24 | 28.2 | 0.6 | 3.30 | 0.10 | 1.1 | 0.1 | 3.55 | 0.81 | n.d. |
| 21-25 | 32.2 | 0.0 | 3.34 | 0.12 | 1.3 | 0.1 | 4.82 | 0.22 | 49 |
| 21-26 | 33.3 | 0.1 | 3.16 | 0.05 | 1.4 | 0.1 | 5.35 | 0.59 | n.d. |
| 21-27 | 33.7 | 0.2 | 3.21 | 0.04 | 1.5 | 0 | 6.6 | 0.06 | n.d. |
| 21-28 | 33.0 | 0.4 | 3.06 | 0.05 | 1.5 | 0.2 | 6.19 | 0.73 | n.d. |
| 21-29 | 45.5 | 0.1 | 3.42 | 0.08 | 2.0 | 1 | 9.56 | 0.88 | n.d. |
| 21-30 | 33.9 | 0.3 | 3.50 | 0.08 | 1.3 | 0 | 4.96 | 0.15 | n.d. |
| 21-31 | 21.8 | 1.0 | 3.51 | 0.05 | 0.7 | 0 | 2.57 | 0.16 | n.d. |
| 21-32 | 63.0 | 0.4 | 3.29 | 0.08 | 3.3 | 0.4 | 16.59 | 1.62 | n.d. |
| 21-33 | 20.3 | 0.6 | 3.21 | 0.09 | 0.7 | 0 | 2.04 | 0.37 | n.d. |

Example 22

Absorbent Materials Prepared with Biomass Derived from Oleaginous Microalgae

This example describes production and testing of absorbent materials produced from biomass prepared from oleaginous microalgae. *Prototheca moriformis* (UTEX 1435) was cultured under heterotrophic conditions such as those described in WO2008/151149, WO2010/063032, and WO2011/150411. Upon cultivation, microalgae was dried then mechanically pressed to extract oil with 15% soybean hulls added by dry weight as a press aid. The resulting microalgal biomass with soybean hull plant polymers retained 7.2% residual oil. This biomass was then milled to a final average particle size of 300 microns and water fractionated as described in Example 1. The insoluble fraction of the biomass was subjected to anionization and crosslinking. Crosslinking with glyoxal was performed using a Lödige reactor. Dry carboxymethylation was performed as described in Example 7. Crosslinked, carboxymethylated biomass was dried with a freeze dryer. The water absorption capacity and saline absorption capacity of the resulting absorbent materials was measured as described in Example 20. Results are presented in Tables 47 and 48.

TABLE 47

Water absorption capacity

| Fraction | Cross-link order | % Cross-linker | CM DS | Water absorption capacity after 15 minutes | Water absorption capacity after 60 minutes |
|---|---|---|---|---|---|
| insoluble | Second | 2 | 0.6 | 17.57 | 17.56 |
| insoluble | Second | 2 | 0.6 | 18.88 | 18.20 |

TABLE 48

Saline absorption capacity

| Fraction | Cross-link order | % Cross-linker | CM DS | Saline absorption capacity after 15 minutes | Saline absorption capacity after 60 minutes |
|---|---|---|---|---|---|
| insoluble | Second | 2 | 0.6 | 12.30 | 12.00 |
| insoluble | Second | 2 | 0.6 | 12.20 | 12.00 |

Example 23

Thermoplastic Compositions Prepared with *Chlorella protothecoides* Microalgal Biomass This example describes the use biomass prepared from heterotrophically cultivated *Chlorella protothecoides* to produce thermoplastic compositions. *Chlorella protothecoides* (UTEX 250) was cultured under heterotrophic conditions such as those described in WO2008/151149, WO2010/063032, and WO2011/150411. Following cultivation, the microalgae and broth were pasteurized then centrifuged to remove liquid. The microalgae were milled with a bead miller, dried with a spray dryer, then exposed to hexane to remove oil. The resulting microalgal biomass retained less than 2% residual oil. This biomass was compounded separately with the three different thermoplastic resins listed in Table 49 according to the weight-based formulations shown. The three samples were compounded on a 26 mm co-rotating twin-screw extruder with resin fed in feed throat and microalgal biomass side-stuffed downstream. Injection molded tensile and flexural test bars were generated with an Engle 85 Injection Moulding Machine. Mechanical, physical, and water absorbent properties were tested according to ASTM standards. Results from these tests are shown in Table 50.

TABLE 49

Formulations of Thermoplastic Compositions Prepared with *Chlorella protothecoides* biomass

| Sample | Resin | Resin Grade | Wt % microalgal biomass | Wt % Resin |
|---|---|---|---|---|
| 49-1 | PLA | NatureWorks 3051D | 40 | 60 |
| 49-2 | LLDPE | ExxonM 1001.59 | 40 | 60 |
| 49-3 | HDPE | Marlex 6007 | 40 | 60 |

TABLE 50

Mechanical, Physical, and Water Absorbent Properties of Thermoplastic Compositions Prepared with *Chlorella protothecoides* biomass.

| | | Sample | | |
|---|---|---|---|---|
| | | 49-1 | 49-2 | 49-3 |
| Tensile Strength (psi) | Average | 2440 | 962 | 2380 |
| | St. Dev. | 24.4 | 45 | 28.7 |
| Elongation (%) | Average | 0.94 | 14.5 | 8.35 |
| | St. Dev. | 0.04 | 9.93 | 0.31 |
| Tensile Modulus (psi) | Average | 484000 | 45000 | 222000 |
| | St. Dev. | 34000 | 4370 | 14300 |
| Flexural Strength (psi) | Average | 5680 | 1460 | 3950 |
| | St. Dev. | 80.6 | 43.2 | 80 |
| Flexural Modulus (psi) | Average | 432000 | 56600 | 187000 |
| | St. Dev. | 9600 | 7370 | 5640 |
| Notched Izod Complete Break ((ft-lb)/in) | Average | 0.5 | | |
| | St. Dev. | 0.02 | | |
| Notched Izod Hinged Break ((ft-lb)/in) | Average | | 6.03 | |
| | St. Dev. | | 0.66 | |
| Notched Izod Partial Break ((ft-lb)/in) | Average | | | 1.38 |
| | St. Dev. | | | 0.08 |
| Un-notched Izod Complete Break ((ft-lb)/in) | Average | 1.82 | | |
| | St. Dev. | 0.2 | | |
| Un-notched Izod Hinged Break ((ft-lb)/in) | Average | | 8.49 | |
| | St. Dev. | | 1.37 | |
| Un-notched Izod Non-Break ((ft-lb)/in) | Average | | | 6.16 |
| | St. Dev. | | | 0.55 |
| Specific Gravity | Average | 1.3 | 1.04 | 1.08 |
| | St. Dev. | 0 | 0.02 | 0 |
| % Weight Change at 24 hrs | Average | 3.78 | 1.7 | 2.23 |
| % Weight Change at 48 hrs | Average | 5.47 | 2.38 | 3.71 |
| % Weight Change at 72 hrs | Average | 6.72 | 3.1 | 4.98 |
| % Weight Change at 96 hrs | Average | 7.83 | 3.76 | 5.97 |
| % Weight Change at 168 hrs | Average | 10.15 | 5.23 | 8.44 |
| Color Scale L* | Average | 48.6 | 44.6 | 46.7 |
| | St. Dev. | 0.35 | 0.85 | 0.24 |
| Color Scale a* | Average | 9.67 | 7.45 | 8.13 |
| | St. Dev. | 0.07 | 0.26 | 0.05 |
| Color Scale b* | Average | 22.5 | 18.6 | 19.2 |
| | St. Dev. | 0.09 | 0.2 | 0.14 |

Example 24

Use of Biomass from Oleaginous Microalgae and Antioxidants in the Production of Thermoplastic Compositions This example describes the use of antioxidants and biomass prepared from heterotrophically cultivated *Prototheca moriformis* to produce thermoplastic compositions. *Prototheca moriformis* (UTEX 1435) was cultured under heterotrophic conditions such as those described in WO2008/151149, WO2010/063032, and WO2011/150411. Upon cultivation, the microalgae was dried then mechanically pressed to extract oil with 15% soybean hulls added by dry weight as a press aid. The resulting microalgal biomass with soybean hull plant polymers retained 7.2% residual oil. This biomass was then milled to a final average particle size of 400 microns, then compounded separately with the two different thermoplastic resins and the different antioxidants listed in Table 51 according to the weight-based formulations shown for each sample. Microalgal biomass was included in each preparation at 30% by weight. Compounds were produced using a 26 mm co-rotating twin-screw extruder heated to 180° C. with resin and antioxidant fed in the feed throat and microalgal biomass side-stuffed downstream. "NW 2003D" refers to NatureWorks 2003D PLA, "BK SLL218" refers to Braskem linear low density polyethylene SLL218.

After compounding, half of the thermoplastic compositions of each material was injection molded into test bars. Mechanical and physical testing of these samples, referred to as "Pass 1 Molds", was evaluated according to ASTM standards. Results are presented in Table 52. The remaining half of the compounds from the first extrusion was processed through the twin-screw extruder a second time. For this second extrusion, the extruder was heated to 210° C. Compounds from this second extrusion were injection molded into test bars, referred to as "Pass 2 Molds". Mechanical and physical testing of these samples was evaluated according to ASTM standards. Results are presented in Table 53.

TABLE 51

Formulations of Thermoplastic Compositions Prepared with microalgal biomass

| | | | | Wt % Antioxidant | | | |
| --- | --- | --- | --- | --- | --- | --- | --- |
| Sample | Resin | Resin Grade | Wt % Resin | Irganox 1010 | Irganox 1098 | Irgafos 168 | Ultranox |
| 51-1 | PLA | NW 2003D | 70 | 0 | 0 | 0 | 0 |
| 51-2 | PLA | NW 2003D | 69.5 | 0.5 | 0 | 0 | 0 |
| 51-3 | PLA | NW 2003D | 69.5 | 0 | 0.5 | 0 | 0 |
| 51-4 | PLA | NW 2003D | 69.5 | 0 | 0 | 0.5 | 0 |
| 51-5 | PLA | NW 2003D | 69.5 | 0 | 0 | 0 | 0.5 |
| 51-6 | PLA | NW 2003D | 69.5 | 0.25 | 0 | 0.25 | 0 |
| 51-7 | PLA | NW 2003D | 69.5 | | 0.25 | 0.25 | 0 |
| 51-8 | PLA | NW 2003D | 69.5 | 0.25 | 0 | 0 | 0.25 |
| 51-9 | PLA | NW 2003D | 69.5 | 0 | 0.25 | 0 | 0.25 |
| 51-10 | LLDPE | BK SLL218 | 70 | 0 | 0 | 0 | 0 |
| 51-11 | LLDPE | BK SLL218 | 69.5 | 0.5 | 0 | 0 | 0 |
| 51-12 | LLDPE | BK SLL218 | 69.5 | 0 | 0.5 | 0 | 0 |
| 51-13 | LLDPE | BK SLL218 | 69.5 | 0 | 0 | 0.5 | 0 |
| 51-14 | LLDPE | BK SLL218 | 69.5 | 0 | 0 | 0 | 0.5 |
| 51-15 | LLDPE | BK SLL218 | 69.5 | 0.25 | 0 | 0.25 | 0 |
| 51-16 | LLDPE | BK SLL218 | 69.5 | 0 | 0.25 | 0.25 | 0 |
| 51-17 | LLDPE | BK SLL218 | 69.5 | 0.25 | 0 | 0 | 0.25 |
| 51-18 | LLDPE | BK SLL218 | 69.5 | 0 | 0.25 | 0 | 0.25 |

TABLE 52

Mechanical and Physical Properties of Pass 1 Molds

| | Tensile Strength (psi) | | Elongation (%) | | Tensile Modulus (psi) | | | | |
| --- | --- | --- | --- | --- | --- | --- | --- | --- | --- |
| Sample | Average | St. Dev. | Average | St. Dev. | Average | St. Dev. | L* | a* | b* |
| 51-1 | 3080 | 38 | 1.26 | 0.2 | 573000 | 15600 | 39.73 | 10.69 | 22.27 |
| 51-2 | 3020 | 40 | 1.2 | 0.03 | 558000 | 21500 | 37.22 | 11.05 | 21.55 |
| 51-3 | 2910 | 18 | 1.16 | 0.08 | 553000 | 11500 | 37.23 | 11.38 | 22.08 |
| 51-4 | 2900 | 35 | 1.35 | 0.12 | 563000 | 12500 | 38.67 | 10.92 | 22.62 |
| 51-5 | 3080 | 32 | 1.41 | 0.21 | 556000 | 19200 | 36.86 | 11.12 | 21.9 |
| 51-6 | 3140 | 27 | 1.31 | 0.08 | 539000 | 17800 | 37.11 | 11.1 | 22.05 |
| 51-7 | 3090 | 26 | 1.35 | 0.13 | 553000 | 7920 | 38.29 | 11.09 | 22.37 |
| 51-8 | 3130 | 15 | 1.36 | 0.09 | 544000 | 7380 | 37.07 | 11.33 | 22.13 |
| 51-9 | 3060 | 60 | 1.32 | 0.06 | 557000 | 21000 | 38.99 | 11.1 | 22.3 |
| 51-10 | 975 | 17 | 23.06 | 2.71 | 50000 | 4640 | 36.38 | 8.91 | 16.03 |
| 51-11 | 979 | 18 | 24.51 | 3.49 | 44900 | 5970 | 35.66 | 9.17 | 16.08 |
| 51-12 | 967 | 11 | 24.2 | 2.43 | 54200 | 3840 | 37.99 | 9 | 16.16 |
| 51-13 | 943 | 9 | 29.21 | 6.3 | 51400 | 5840 | 36.49 | 9.14 | 16.58 |
| 51-14 | 953 | 17 | 26.18 | 1.37 | 48000 | 4110 | 36.78 | 9.22 | 16.43 |
| 51-15 | 1010 | 9 | 28.5 | 5.82 | 48800 | 4890 | 36.05 | 9.16 | 16.33 |
| 51-16 | 1020 | 5 | 26.58 | 5.01 | 52900 | 3860 | 36.37 | 9.32 | 16.61 |
| 51-17 | 1010 | 15 | 26.57 | 5.16 | 46400 | 5050 | 35.59 | 9.05 | 15.94 |
| 51-18 | 990 | 12 | 27.84 | 4.02 | 52300 | 6310 | 35.82 | 9.31 | 16.45 |

TABLE 53

Mechanical and Physical Properties of Pass 2 Molds

| Sample | Tensile Strength (psi) Average | St. Dev. | Elongation (%) Average | St. Dev. | Tensile Modulus (psi) Average | St. Dev. | L* | a* | b* |
|---|---|---|---|---|---|---|---|---|---|
| 51-1  | 3030 | 71 | 1.21  | 0.09 | 542000 | 12400 | 26.84 | 7.89 | 13.04 |
| 51-2  | 2870 | 85 | 1.19  | 0.15 | 522000 | 27200 | 20.52 | 4.47 | 6.49 |
| 51-3  | 3130 | 22 | 1.33  | 0.08 | 547000 | 13000 | 27.16 | 7.68 | 12.66 |
| 51-4  | 3040 | 11 | 2.93  | 0.6  | 560000 | 14200 | 29.48 | 8.97 | 15.67 |
| 51-5  | 3060 | 23 | 1.89  | 0.41 | 559000 | 18400 | 30.21 | 9.08 | 15.75 |
| 51-6  | 3140 | 24 | 1.34  | 0.27 | 555000 | 14000 | 29.74 | 9.19 | 15.4 |
| 51-7  | 3030 | 32 | 2.05  | 0.42 | 562000 | 32400 | 28.84 | 8.96 | 14.57 |
| 51-8  | 3130 | 14 | 1.6   | 0.66 | 545000 | 14200 | 28.89 | 9.06 | 14.34 |
| 51-9  | 3040 | 8  | 2.15  | 0.22 | 537000 | 12100 | 29.21 | 8.83 | 14.14 |
| 51-10 | 1000 | 8  | 28.86 | 6.29 | 48400  | 4640  | 25.62 | 5.34 | 7.57 |
| 51-11 | 970  | 22 | 26.83 | 4.96 | 36900  | 3310  | 26.28 | 5.17 | 7.55 |
| 51-12 | 966  | 10 | 24.39 | 4.4  | 41600  | 7490  | 26.41 | 5.44 | 7.74 |
| 51-13 | 961  | 12 | 32.97 | 9.27 | 52500  | 5160  | 26.97 | 5.65 | 8.42 |
| 51-14 | 978  | 13 | 19.93 | 3.41 | 42200  | 6790  | 26.97 | 6.11 | 8.73 |
| 51-15 | 975  | 16 | 25.01 | 5.02 | 41000  | 5590  | 25.69 | 6.05 | 8.54 |
| 51-16 | 969  | 11 | 26.16 | 5.56 | 47500  | 6540  | 25.75 | 6.12 | 8.77 |
| 51-17 | 955  | 9  | 27.82 | 5.08 | 39100  | 2520  | 25.99 | 6.12 | 8.78 |
| 51-18 | 952  | 27 | 25.96 | 6.03 | 45000  | 4660  | 24.95 | 6.34 | 8.71 |

Example 25

Thermoplastic Compositions Prepared with Covalently Modified Biomass from Oleaginous Microalgae This example describes the use of covalently modified microalgal biomass to produce thermoplastic compositions with improved properties. *Prototheca moriformis* (UTEX 1435) was cultured under heterotrophic conditions such as those described in WO2008/151149, WO2010/063032, and WO2011/150411. Upon cultivation, microalgae were dried then mechanically pressed with soybean hull as a press aid, added at 15% by dry weight, to extract oil. The microalgal biomass produced through this process was then either used directly in compounding thermoplastic compositions (biomass 54A) or acetylated according to the procedure described in Example 16 (biomass 54-B) then used in compounding thermoplastic compositions. The DS of acetylation was 2.3. Four samples (54A-1, 54A-2, 54B-1, 54B-2) were compounded with the different thermoplastic resins listed in Table 54 according to the weight-based formulations shown. Compounding was conducted with on a 26 mm co-rotating twin-screw extruder with resin fed in the feed throat and microalgal biomass side-stuffed downstream. Injection molded tensile and flexural test bars were generated with an Engle 85 Injection Moulding Machine. Mechanical, physical, and water absorbent properties were tested according to ASTM standards. Results from these tests are shown in Table 55.

TABLE 54

Formulations of Thermoplastic Compositions Prepared with *Prototheca moriformis* (UTEX 1435) microaglal biomass

| Microalgal Biomass | Sample | Resin | Resin Grade | Wt % microalgal biomass | Wt % Resin |
|---|---|---|---|---|---|
| 54A | 54A-1 | LLDPE | ExxonM 1001.59 | 40 | 60 |
| 54A | 54A-2 | HDPE  | Marlex 6007 | 40 | 60 |
| 54B | 54B-1 | LLDPE | ExxonM 1001.59 | 40 | 60 |
| 54B | 54B-2 | HDPE  | Marlex 6007 | 40 | 60 |

TABLE 55

Mechanical, Physical, and Water Absorbent Properties of Thermoplastic Compositions Prepared with microalgal biomass.

| Property | | 54A-1 | 54A-2 | 54B-1 | 54B-2 |
|---|---|---|---|---|---|
| Tensile Strength (psi) | Average | 989 | 2080 | 880 | 1990 |
|                        | St. Dev. | 14 | 15 | 13 | 64 |
| Elongation (%) | Average | 39.17 | 12.07 | 94.36 | 6.72 |
|                | St. Dev. | 5.95 | 0.86 | 6.38 | 0.77 |
| Tensile Modulus (psi) | Average | 53300 | 229000 | 84100 | 273000 |
|                       | St. Dev. | 14000 | 7680 | 5730 | 12200 |
| Flexural Strength (psi) | Average | 1370 | 3640 | 1580 | 4150 |
|                         | St. Dev. | 19 | 33 | 16 | 221 |
| Flexural Modulus (psi) | Average | 53200 | 220000 | 79900 | 220000 |
|                        | St. Dev. | 2270 | 2520 | 2760 | 13700 |
| Notched Izod Hinged Break ((ft-lb)/in) | Average | | 1.39 | 3.72 | 0.80 |
|  | St. Dev. | | 0.09 | 0.61 | 0.03 |

TABLE 55-continued

Mechanical, Physical, and Water Absorbent Properties of Thermoplastic Compositions Prepared with microalgal biomass.

| Property | | Sample | | | |
|---|---|---|---|---|---|
| | | 54A-1 | 54A-2 | 54B-1 | 54B-2 |
| Notched Izod Partial Break ((ft-lb)/in) | Average St. Dev. | 4.34 0.33 | | 2.95 | |
| Un-notched Izod Complete Break ((ft-lb)/in) | Average St. Dev. | | | | 2.35 0.42 |
| Un-notched Izod Hinged Break ((ft-lb)/in) | Average St. Dev. | | | | 1.76 0.00 |
| Un-notched Izod Partial Break ((ft-lb)/in) | Average St. Dev. | | | 5.85 0.95 | 9.68 1.81 |
| Un-notched Izod Non-Break ((ft-lb)/in) | Average St. Dev. | 7.46 0.77 | | 11.22 1.44 | |
| Specific Gravity | Average St. Dev. | 1.06 0.01 | 1.08 0.00 | 1.03 0.00 | 1.06 0.00 |
| % Weight Change at 24 hrs | Average | 1.26 | 1.64 | 0.70 | 0.50 |
| % Weight Change at 48 hrs | Average | 1.59 | 2.86 | 0.92 | 0.46 |
| % Weight Change at 72 hrs | Average | 1.93 | 3.94 | 1.15 | 0.51 |
| % Weight Change at 96 hrs | Average | 2.35 | 5.25 | 1.37 | 0.71 |
| % Weight Change at 168 hrs | Average | 2.99 | 8.46 | 1.66 | 0.80 |
| Color Scale L* | Average St. Dev. | 29.12 | 37.7 | 29.49 0.48 | 25.58 0.28 |
| Color Scale a* | Average St. Dev. | 8.07 | 9.03 | 4.07 0.05 | 3.7 0.02 |
| Color Scale b* | Average St. Dev. | 13.69 | 17.11 | 8.45 0.1 | 6.21 0.05 |

As shown in Table 55, the impact of preparing thermoplastic compositions comprising acetylated microalgae is a decrease in specific gravity and a decrease in water uptake relative to thermoplastic compositions comprising unmodified microalgal biomass. After 24 hours in water submersion, water uptake decreased by nearly 45% in the LLDPE-acetylated biomass composition and by nearly 70% in the HDPE-acetylated biomass composition. After 168 hours in water submersion, water uptake decreased by nearly 45% in the LLDPE-acetylated biomass composition and by nearly 90% in the HDPE-acetylated biomass composition. For materials comprising LLDPE the impact of preparing thermoplastic compositions with acetylated microalgal biomass is an improvement in elongation, tensile modulus, flexural strength, and flexural modulus but decreased tensile and impact strength relative thermoplastic compositions prepared with unmodified microalgal biomass. For materials comprising HDPE, the impact of preparing thermoplastic compositions with acetylated microalgal biomass is an improvement in tensile modulus and flexural strength but decreased tensile strength, impact strength, and elongation relative to thermoplastic compositions prepared with unmodified microalgal biomass.

This example demonstrates the successful use of acetylated microalgal biomass to improve specific mechanical and physical properties of thermoplastic compositions prepared with microalgal biomass.

Example 26

Thermoplastic Compositions Comprising Microalgal Biomass with Improved Impact Strength This example describes the use of biomass prepared from oleaginous microalgae to produce thermoplastic compositions with improved impact strength. *Prototheca moriformis* (UTEX 1435) was cultivated under heterotrophic conditions such as those described in WO2008/151149, WO2010/063032, and WO2011/150411, dried, then mechanically pressed to extract oil. Three different microalgal biomass preparations (56A, 56B, and 56C) were obtained through alterations in processing, extraction, and milling conditions. Soybean hulls, used as a press aid in the extraction process, were added at the dry weight percentages indicated in Table 56. Additional characteristics of the algal biomass samples are listed in Table 56. These biomass preparations were milled to different final average particle sizes, then compounded with polypropylene copolymer (ExxonMobil PP7033N), maleic anhydride grafted polypropylene, antioxidant, and elastomer according to the weight-based formulations for each sample shown in Table 57. Compounding was conducted with on a 26 mm co-rotating twin-screw extruder with resin fed in the feed throat and microalgal biomass side-stuffed downstream. Injection molded tensile and flexural test bars were generated with an Engle 85 Injection Moulding Machine. Mechanical and physical properties of the compositions were tested according to ASTM standards. Results from these tests are shown in Table 58.

TABLE 56

Microalgal Biomass Preparations used in compounding thermoplastic compositions

| Microalgal Biomass Preparation | % Residual Oil Content | Wt Soy Hull % addition | Milling Method | Average Particle Size (micron) |
|---|---|---|---|---|
| 56A | 9 | 15 | Hammer | 300 |
| 56B | 7.2 | 15 | Hammer, jet | 5 |
| 56C | 9 | 30 | Jet | 40 |

TABLE 57

Formulations for Thermoplastic Compositions Comprising Microalgal Biomass Preparations

| Sample | Microalgal Biomass Preparation | Wt % Microalgal Biomass | Wt % ExxonMobil PP7033N | Wt % MAPP | Wt % Anox 20 | Wt % Engage 8003 |
|---|---|---|---|---|---|---|
| 57-1 | 56A | 15 | 72.75 | 2 | 0.25 | 10 |
| 57-2 | 56A | 25 | 62.75 | 2 | 0.25 | 10 |
| 57-3 | 56B | 15 | 72.75 | 2 | 0.25 | 10 |
| 57-4 | 56B | 20 | 67.75 | 2 | 0.25 | 10 |

TABLE 57-continued

Formulations for Thermoplastic Compositions Comprising Microalgal Biomass Preparations

| Sample | Microalgal Biomass Preparation | Wt % Microalgal Biomass | Wt % ExxonMobil PP7033N | Wt % MAPP | Wt % Anox 20 | Wt % Engage 8003 |
|---|---|---|---|---|---|---|
| 57-5 | 56B | 25 | 62.75 | 2 | 0.25 | 10 |
| 57-6 | 56B | 30 | 57.75 | 2 | 0.25 | 10 |
| 57-7 | 56C | 15 | 72.75 | 2 | 0.25 | 10 |
| 57-8 | 56C | 20 | 67.75 | 2 | 0.25 | 10 |
| 57-9 | 56C | 25 | 62.75 | 2 | 0.25 | 10 |
| 57-10 | 56C | 30 | 57.75 | 2 | 0.25 | 10 |

TABLE 58

Mechanical and Physical Properties of Thermoplastic Compositions Comprising Microalgal Biomass

| | | Microalgal Biomass Preparation | | | | | | | | | |
|---|---|---|---|---|---|---|---|---|---|---|---|
| | | 56A | | 56B | | | | 56C | | | |
| | | Sample | | | | | | | | | |
| Property | | 57-1 | 57-2 | 57-3 | 57-4 | 57-5 | 57-6 | 57-7 | 57-8 | 57-9 | 57-10 |
| Tensile Strength (psi) | Average | 2180 | 2020 | 2310 | 2330 | 2180 | 2150 | 2140 | 2060 | 1800 | 1810 |
| | St. Dev. | 28 | 14 | 33 | 19 | 38 | 31 | 20 | 24 | 12 | 15 |
| Elongation (%) | Average | 8.12 | 7.1 | 7.45 | 7.09 | 6.55 | 5.84 | 8.29 | 8.43 | 5.73 | 6.98 |
| | St. Dev. | 0.83 | 0.36 | 0.5 | 0.75 | 0.79 | 0.8 | 1.03 | 1.22 | 0.18 | 0.8 |
| Tensile Modulus (psi) | Average | 157000 | 171000 | 163000 | 176000 | 177000 | 186000 | 156000 | 160000 | 173000 | 168000 |
| | St. Dev. | 2150 | 2250 | 6010 | 3060 | 2340 | 3990 | 3510 | 6930 | 1880 | 3640 |
| Flexural Strength (psi) | Average | 4130 | 4130 | 4190 | 4220 | 4190 | 4170 | 4000 | 4020 | 3840 | 3770 |
| | St. Dev. | 64 | 34 | 113 | 73 | 80 | 96 | 157 | 61 | 58 | 64 |
| Flexural Modulus (psi) | Average | 147000 | 169000 | 145000 | 153000 | 161000 | 166000 | 140000 | 154000 | 176000 | 166000 |
| | St. Dev. | 3600 | 4760 | 6690 | 5180 | 3810 | 6700 | 13400 | 4440 | 1740 | 6590 |
| Notched Izod Hinged Break ((ft-lb)/in) | Average | 2.58 | 1.51 | 1.88 | 1.57 | 1.27 | 1.15 | 2.86 | 2.66 | 2.24 | 2.45 |
| | St. Dev. | 0.21 | 0.08 | 0.18 | 0.15 | 0.08 | 0.06 | 0.28 | 0.41 | 0.27 | 0.24 |
| Un-notched Izod Complete Break ((ft-lb)/in) | Average | | | | | | 4.28 | | | | |
| | St. Dev. | | | | | | 0.47 | | | | |
| Un-notched Izod Hinged Break ((ft-lb)/in) | Average | 9.97 | 6.34 | 10.57 | 8.85 | 6.61 | 5.49 | 11.42 | 10.56 | 6.79 | 7.32 |
| | St. Dev. | 0.83 | 0.69 | 2.26 | 1.06 | 0.76 | 0.22 | 1.38 | 1.23 | 1.36 | 0.97 |
| Specific Gravity | Average | 0.93 | 0.95 | 0.94 | 0.96 | 0.97 | 0.99 | 0.92 | 0.93 | 0.95 | 0.95 |
| | St. Dev. | 0 | 0 | 0.01 | 0 | 0 | 0 | 0 | 0 | 0 | 0 |

As shown in Table 58, different microalgal biomass preparations are associated with different thermoplastic composition mechanical properties. Inclusion of preparation 56C in thermoplastic compositions led to improved impact strength relative to preparations comprising either 56A or 56B. Across all compositions, there is a trend for decreased impact strength with greater weight percent inclusion of microalgal biomass. Of the three preparations evaluated, 56C led to least decrease in impact strength with an increase in microalgal biomass added to the thermoplastic compositions.

The various embodiments and aspects set forth in the application may be combined with each other. The described embodiments and aspects are intended to be merely exemplary and numerous variations and modifications will be apparent to those skilled in the art. All such variations and modifications are intended to be within the scope of the present invention.

All references cited herein, including patents, patent applications, and publications are hereby incorporated by reference in their entireties, whether previously specifically incorporated or not. The publications mentioned herein are cited for the purpose of describing and disclosing reagents, methodologies and concepts that may be used in connection with the present invention. Nothing herein is to be construed as an admission that these references are prior art in relation to the inventions described herein.

What is claimed is:

1. A thermoplastic composition comprising a covalently modified microalgal biomass from a heterotrophically cultivated microalgae, the composition further comprising soybean hulls.

2. The composition according to claim 1, wherein the microalgae has been lysed.

3. The composition according to claim 1, wherein the covalently modified microalgal biomass has been covalently modified with a hydrophobic group or an anionic group.

4. The composition of claim 3, wherein the microalgal biomass has been modified by acetylation.

5. The composition of claim 3, wherein polysaccharide of the microalgal biomass is covalently modified.

6. The composition according to claim 3, wherein the covalently modified algal biomass is characterized by a DS value of 1 to 3.

7. The composition according to claim 1, wherein the microalgal biomass is unbleached.

8. The composition according to claim 1, wherein the microalgal biomass is not colored due to the presence of chlorophyll.

9. The composition according to claim 1, wherein the biomass is of microalgae that are heterotrophs, and optionally obligate heterotrophs.

10. The composition according to claim 1, wherein the microalgae are of the genus *Chlorella* or the genus *Prototheca*.

11. The composition according to claim 10, wherein the microalgae are *Prototheca moriformis*.

12. The composition according to claim 1, wherein the thermoplastic composition further comprises a plasticizer.

13. The composition according to claim 12, wherein the plasticizer is selected from a group consisting of one or more of: glycerol, sorbitol, triacetin, triethyl citrate, acetyl triethyl citrate, tributyl cirtate, acetyl tributyl citrate, trioctyl citrate, acetyl trioctyl citrate, trihexyl citrate, butyryl trihexyl citrate, trimethyl citrate, alkyl sulphonic acid phenyl ester, and 1,2-cyclohexane dicarboxylic acid diisononyl ester.

14. The composition according to claim 1, wherein the thermoplastic composition has one or more of the following characteristics: (a) a Young's modulus of 300-3000 MPa; (b) a tensile strength of 5-70 MPa; (c) a tensile strength at maximum load of 5-50 MPa; or (d) an ultimate elongation of 1-400%.

15. The composition according to claim 1, wherein the microalgal biomass is a fraction that is insoluble in an aqueous solvent, said insoluble fraction produced by removing components soluble in an aqueous solvent from microalgal biomass.

16. The composition according to claim 1, wherein the composition has been formed through extruding, molding, or blowing.

17. The thermoplastic composition according to claim 1, wherein the composition is a film.

* * * * *